(12) United States Patent
Blackburn

(10) Patent No.: US 6,875,619 B2
(45) Date of Patent: Apr. 5, 2005

(54) MICROFLUIDIC DEVICES COMPRISING BIOCHANNELS

(75) Inventor: Gary Blackburn, Glendora, CA (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/861,171

(22) Filed: May 17, 2001

(65) Prior Publication Data

US 2003/0190608 A1 Oct. 9, 2003

(51) Int. Cl.$^7$ .............................................. G01N 33/558
(52) U.S. Cl. ......................... 436/514; 435/6; 435/7.1; 435/287.1; 435/287.2; 436/518; 436/524; 436/527; 436/531; 436/805
(58) Field of Search ................. 436/518, 514, 436/524, 527, 531, 805; 435/6, 7.1, 287.1, 287.2

(56) References Cited

U.S. PATENT DOCUMENTS

| | | |
|---|---|---|
| 4,415,732 A | 11/1983 | Caruthers |
| 4,683,195 A | 7/1987 | Mullis et al. |
| 4,713,347 A | 12/1987 | Mitchell et al. |
| 4,755,458 A | 7/1988 | Rabbani |
| 4,840,893 A | 6/1989 | Hill et al. |
| 4,920,047 A | 4/1990 | Giaever et al. |
| 5,015,569 A | 5/1991 | Pontius |
| 5,064,618 A | 11/1991 | Baker et al. |
| 5,066,372 A | 11/1991 | Weetall |
| 5,071,531 A | 12/1991 | Soane |
| 5,126,022 A | 6/1992 | Soane et al. |
| 5,130,238 A | 7/1992 | Malek et al. |
| 5,135,627 A | 8/1992 | Soane |
| 5,147,607 A * | 9/1992 | Mochida .................. 422/57 |
| 5,192,507 A | 3/1993 | Taylor et al. |
| 5,296,375 A | 3/1994 | Kricka et al. |
| 5,304,487 A * | 4/1994 | Wilding et al. ............ 422/55 |

(Continued)

FOREIGN PATENT DOCUMENTS

| | | | |
|---|---|---|---|
| EP | 0 527 905 | * | 8/1991 |
| EP | 0478319 A1 | | 1/1992 |
| EP | 0478319 B1 | | 1/1992 |
| EP | 0 969 083 | * | 1/2000 |

(Continued)

OTHER PUBLICATIONS

Lofas et al, Chemical Communications, 1990, pp. 1526–1528.*
Cantor, C.R. et al., "Report on the Sequencing by Hybridization Workshop," *Genomics*, 13:1378–1383 (1992).
Commerce Business Daily Issue of Sep. 26, 1996 PSA#1688.

(Continued)

Primary Examiner—Christopher L. Chin
(74) Attorney, Agent, or Firm—Robin M. Silva, Esq.; Renee M. Kosslak, Esq.; Dorsey & Whitney LLP

(57) ABSTRACT

The present invention is directed to a variety of microfluidic devices with configurations including the use of biochannels or microchannels comprising arrays of capture binding ligands to capture target analytes in samples. The invention provides microfluidic cassettes or devices that can be used to effect a number of manipulations on a sample to ultimately result in target analyte detection or quantification.

25 Claims, 38 Drawing Sheets

U.S. PATENT DOCUMENTS

| | | |
|---|---|---|
| 5,455,166 A | 10/1995 | Walker |
| 5,486,335 A | 1/1996 | Wilding et al. |
| 5,494,810 A | 2/1996 | Barany et al. |
| 5,498,392 A | 3/1996 | Wilding et al. |
| 5,505,321 A | 4/1996 | Caron et al. |
| 5,519,635 A | 5/1996 | Miyake et al. |
| 5,552,270 A | 9/1996 | Khraako et al. |
| 5,569,364 A | 10/1996 | Hooper et al. |
| 5,585,069 A | 12/1996 | Zanzucchi et al. |
| 5,587,128 A | 12/1996 | Wilding |
| 5,593,838 A | 1/1997 | Zanzucchi et al. |
| 5,595,908 A | 1/1997 | Fawcett et al. |
| 5,603,351 A | 2/1997 | Cherukuri |
| 5,605,662 A | 2/1997 | Heller et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,643,738 A | 7/1997 | Zanzucchi et al. |
| 5,653,939 A * | 8/1997 | Hollis et al. .................. 422/50 |
| 5,681,484 A | 10/1997 | Zanzucchi et al. |
| 5,705,346 A | 1/1998 | Okamoto et al. |
| 5,716,825 A * | 2/1998 | Hancock et al. ......... 435/286.5 |
| 5,726,026 A * | 3/1998 | Wilding et al. ............ 435/7.21 |
| 5,727,548 A | 3/1998 | Hill et al. |
| 5,728,532 A | 3/1998 | Ackley |
| 5,741,462 A | 4/1998 | Nova et al. |
| 5,747,169 A | 5/1998 | Fan et al. |
| 5,750,015 A | 5/1998 | Soane |
| 5,755,942 A | 5/1998 | Zanzucchi et al. |
| 5,756,050 A | 5/1998 | Ershov et al. |
| 5,759,866 A * | 6/1998 | Machida et al. ............ 436/518 |
| 5,770,029 A | 6/1998 | Nelson et al. |
| 5,837,859 A | 11/1998 | Teoule et al. |
| 5,849,486 A | 12/1998 | Heller et al. |
| 5,863,502 A * | 1/1999 | Southgate et al. ............ 422/58 |
| 5,866,345 A | 2/1999 | Wilding et al. |
| 5,942,443 A * | 8/1999 | Parce et al. .................. 436/514 |
| 5,976,802 A | 11/1999 | Ansorge |
| 6,063,589 A * | 5/2000 | Kellogg et al. ................. 435/4 |
| 6,096,825 A | 8/2000 | Garnier |
| 6,100,045 A | 8/2000 | Van Es |
| 6,100,099 A | 8/2000 | Gordon et al. |
| 6,114,122 A | 9/2000 | Besemer et al. |
| 6,150,119 A * | 11/2000 | Kopf-Sill et al. ............ 435/7.1 |
| 6,150,180 A * | 11/2000 | Parce et al. .................. 436/514 |
| 6,197,595 B1 * | 3/2001 | Anderson et al. ........... 436/180 |
| 6,203,758 B1 | 3/2001 | Marks et al. |
| 6,207,369 B1 | 3/2001 | Wohlstadter et al. |
| 6,221,677 B1 * | 4/2001 | Wu et al. .................... 436/518 |
| 6,258,593 B1 | 7/2001 | Schembi et al. |
| 6,300,141 B1 | 10/2001 | Segal et al. |
| 6,306,590 B1 * | 10/2001 | Mehta et al. ................... 435/6 |
| 6,326,211 B1 | 12/2001 | Anderson et al. |
| 6,368,871 B1 * | 4/2002 | Christel et al. ............. 436/180 |
| 2002/0006643 A1 | 1/2002 | Kayyem et al. |

FOREIGN PATENT DOCUMENTS

| | | |
|---|---|---|
| WO | WO 98/05424 | 2/1985 |
| WO | WO 86/05815 | 3/1985 |
| WO | 93/22053 * | 11/1993 |
| WO | WO 96/15576 | 5/1996 |
| WO | WO 96/39260 | 12/1996 |
| WO | WO 96/15450 | 5/1997 |
| WO | WO 97/16561 | 5/1997 |
| WO | WO 97/16835 | 5/1997 |
| WO | WO 97/27324 | 7/1997 |
| WO | WO 97/27329 | 7/1997 |
| WO | WO 97/31256 | 8/1997 |
| WO | WO 97/37755 | 10/1997 |
| WO | WO 97/43629 | 11/1997 |
| WO | WO 98/04740 | 2/1998 |
| WO | WO 98/12539 | 3/1998 |
| WO | WO 98/13683 | 4/1998 |
| WO | 98/32018 * | 7/1998 |
| WO | 98/49344 * | 11/1998 |
| WO | WO 98/51823 | 11/1998 |
| WO | WO 99/29711 | 6/1999 |
| WO | WO 99/33559 | 7/1999 |
| WO | WO 99/37819 | 7/1999 |
| WO | WO 00/62931 | 10/2000 |
| WO | WO 0106016 | 1/2001 |
| WO | WO 02/43864 | 6/2002 |
| WO | WO 0177135 | 11/2002 |

OTHER PUBLICATIONS

Dontha et al., "Generation of Biotin/Avidin/Enzyme Nanostructures with Maskless Photolithography," Anal. Chem. 69:2619–2625 (1997).

Drobyshev, A. et al., "Sequence Analysis by Hybridization with Oligonucleotide Microchip: Identification of β–thalassemia Mutations," Gene, 188:45–52 (1997).

Dubiley, S. et al., "Fractionation, phosphorylation and Ligation on Oligonucleotide Microchips to Enhance Sequencing by Hybridization," Nucleic Acids Research, 25(12):2259–2265 (1997).

Griffin et al., ""Single–nucleotide polymorphism analysis by MALDI–TOF mass spectrometry,"" Trends in Biotechnology, 14(10):77–84 (2000).

Guschin, D. et al., "Oligonucleotide Microchips as Genosensors for Determinative and Environmental Studies in Microbiology," 63(6):2397–2402 (1997).

Hegner, et al., "Immobilizing DNA on gold via thiol modification for atomic force microscopy imaging in buffer solutions," FEBS 336(3):452–456 (1993).

Lee, et al., "Direct Measurement of the Forces Between Complementary Strands of DNA," Science, 266:771–773 (1994).

Liu et al., "Passive mxing in a three dimensional serpentine microchannel," J. Micorelectromechanical Systems 9(2):190–196 (2000).

Maskos, et al., "Oligonucleotide hybridisations on glass supports: a novel linker for oligonucleotide synthesis and hybridisation properties of oligonucleotides synthesised in situ," Nucleic Acids Research, 20(7):1679–1684 (1992).

Mirkin et al., "A DNA–based Method for Ratioally Assembling Nonoparticles into Macroscopic Materials," Nature, 382:607–609 (1996).

Mirzabekov, A. et al., "Dna Sequencing by Hybridization—a Megasequencing Method and a Diagnostic Tool," Tibtech, 12:27–32 (1994).

Mrksich et al., "Enhanced Sequence specific recognition in the minor groove of DNA by covalent peptide Dimers: Bis(pyridine–2–carboxamidonetropsin)(CH2) 3–6," J. Am. Chem. Soc. 1993, 115:9892–9899 (1993).

O'Donnell–Maloney et al., ""The development of microfabricated arrays for DNA sequencing and analysis,"" Trends in Biotechnology, 14(10):401–407 (1996.

Southern, et al., "Arrays of complementary oligonucleotides for analysing the hybridisation behaviour of nucleic acids," Nucleic Acids Research, 22(8):1368–1373 (1994.

Storhoff et al., "One–Pot Colorimetric Differentiation of Polynucleotides with Single Base Imperfections Using Gold Nanoparticles Probes," J. Am. Chem. Soc., 120:1959–1964 (1998).

Su, et al., "Interfacial Nucleic Acid Hybridization Studied by Random Primer $^{32}$P Labelling and Liquid–Phase Acoustic Network Analysis," *Analytical Chemistry*, 66(6):769–777 (1994).

Uto, Y. et al., "Electrochemical Analysis of DNA amplified by the Polymerase Chain Reaction with a Ferrocenylated Oligonucleotide," Anal. Chem. 250: 122–124 (1997).

Van Ness, J., et al., "A Versatile Solid Support System for Oligodeoxynucleotide Probe–Based Hybridization Assays," *Nucleic Acids Research*, 19(12):3345–3350 (1991).

Williams, et al., "Studies of oligonucleotide interactions by hybridisation to arrays: the influence of dangling ends on duplex yield," *Nucleic Acids Research*, 22(8):1365–1367 (1994).

* cited by examiner

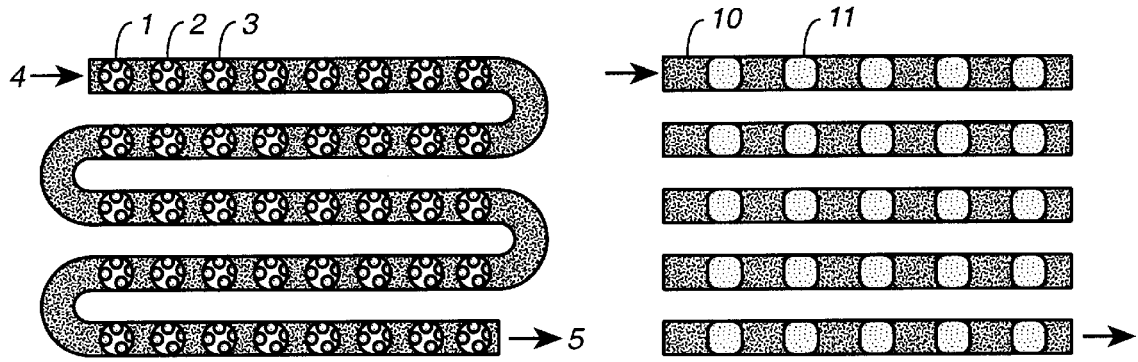
FIG._1  FIG._2
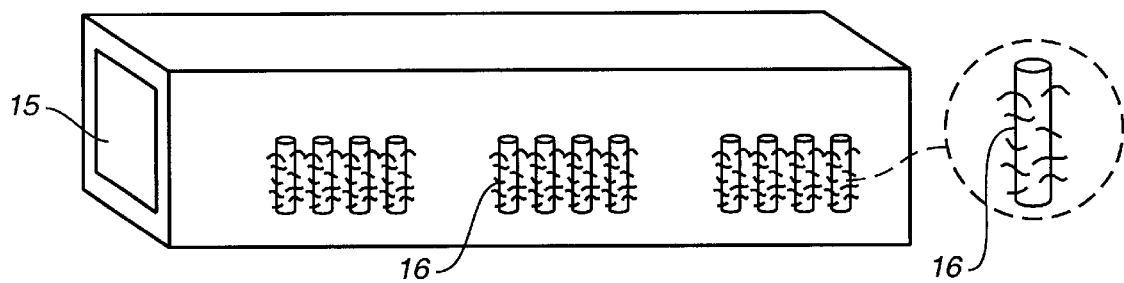
FIG._3a
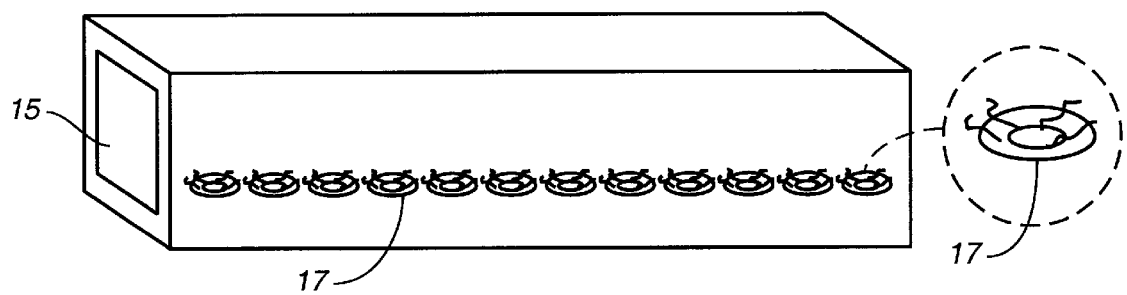
FIG._3b

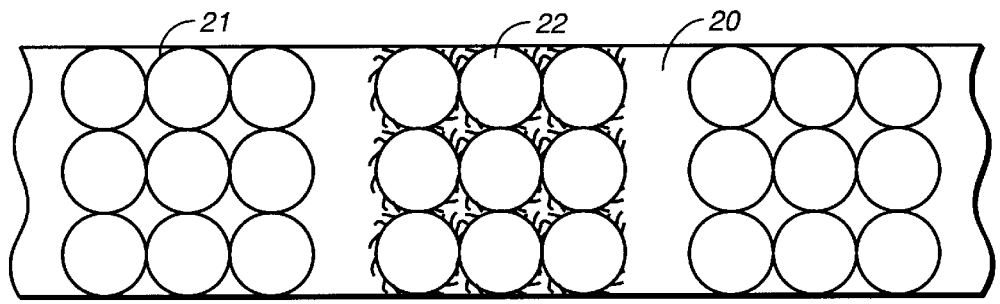
FIG._4
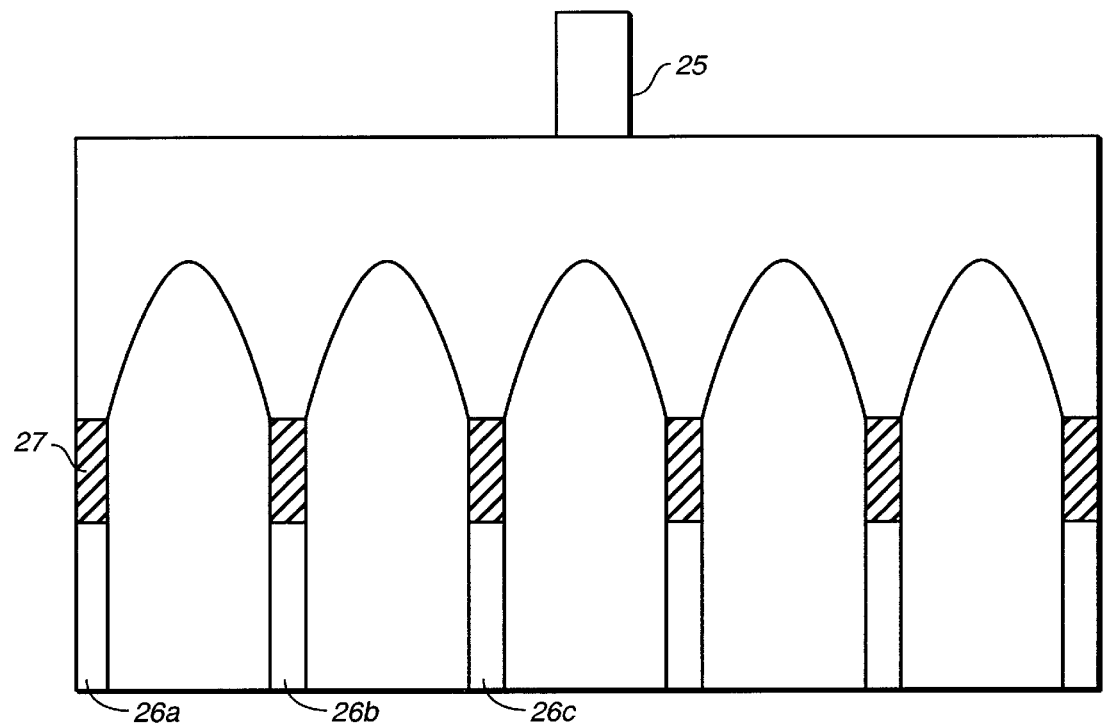
FIG._5

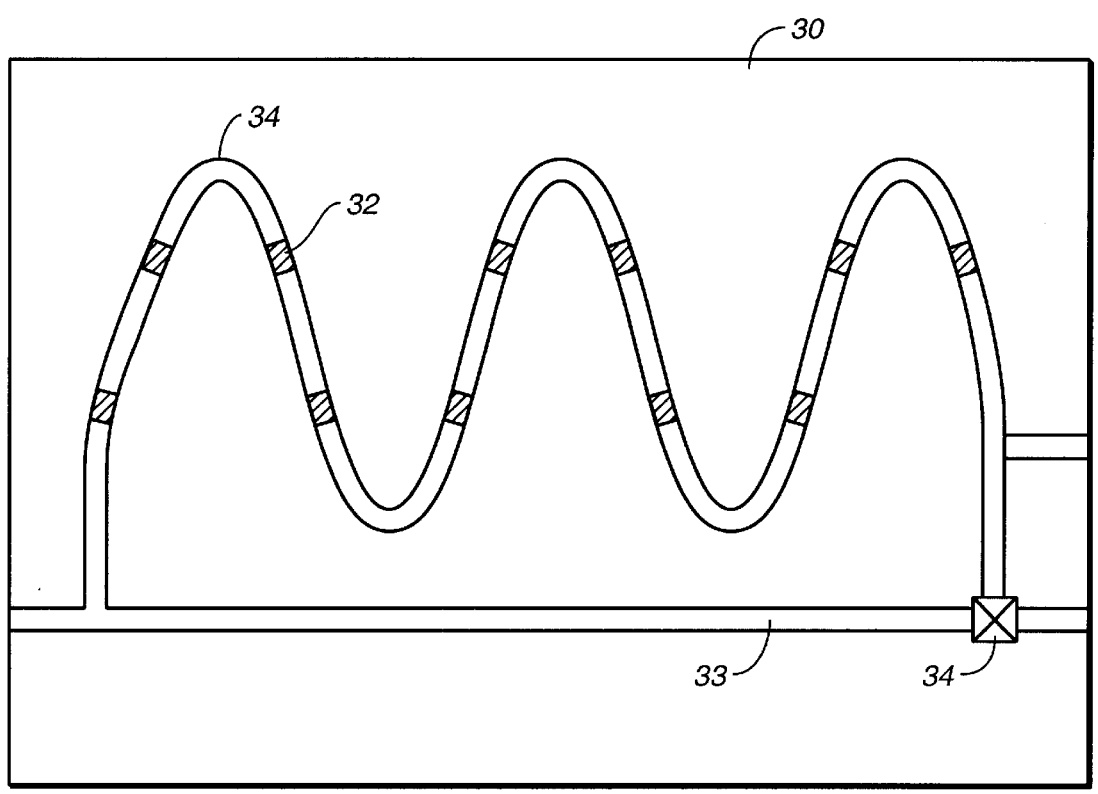
FIG._6

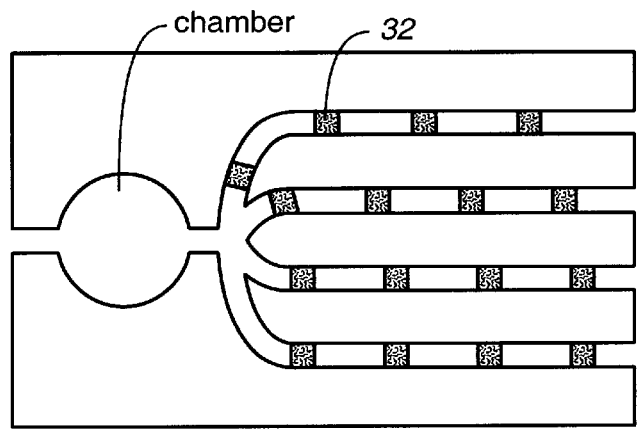
FIG._7A
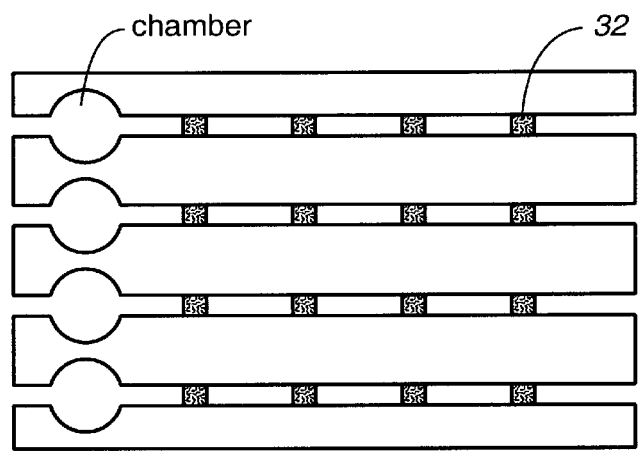
FIG._7B
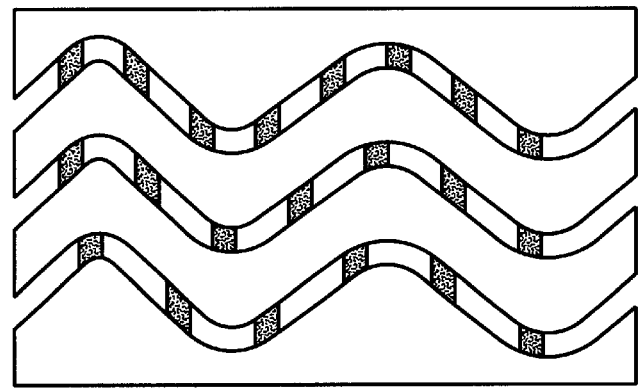
FIG._7C

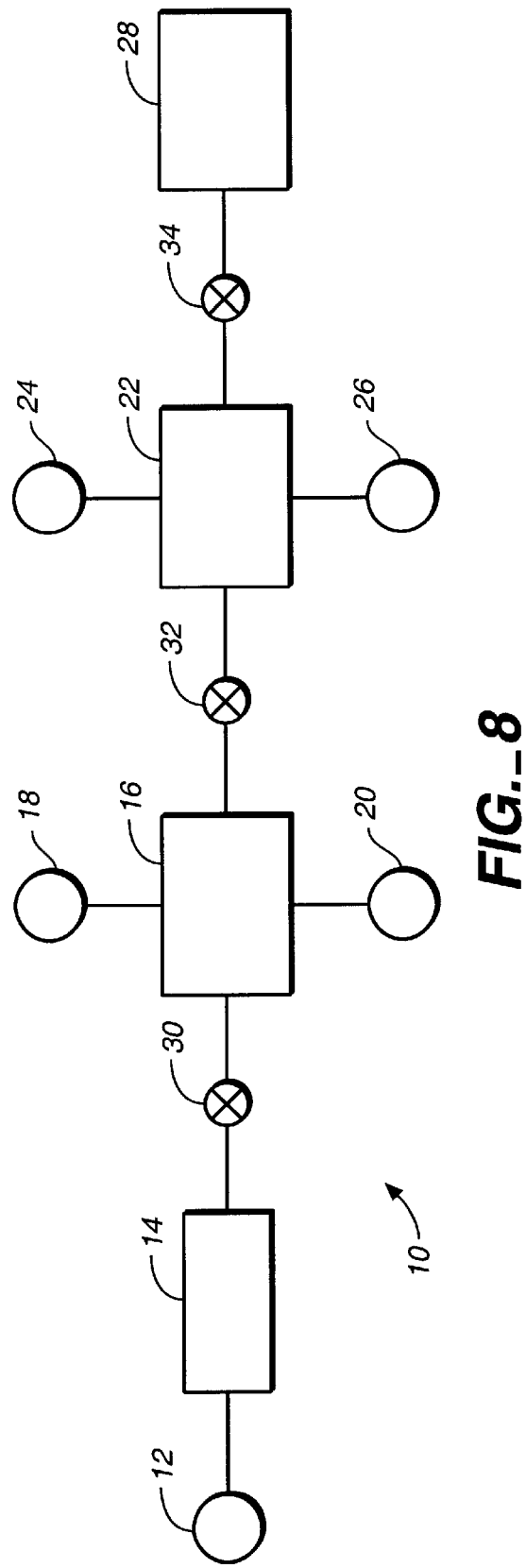
FIG._8

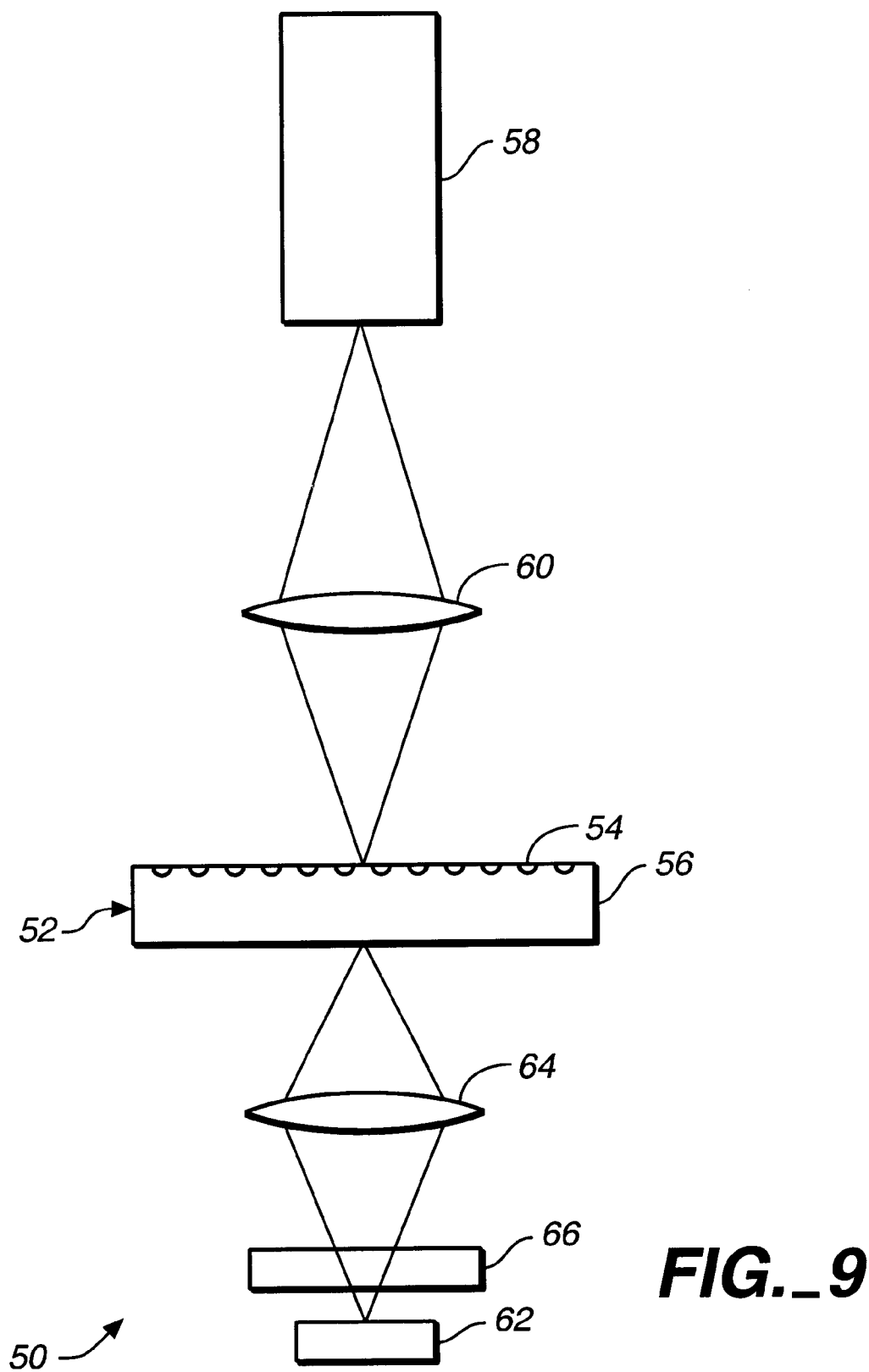
FIG._9

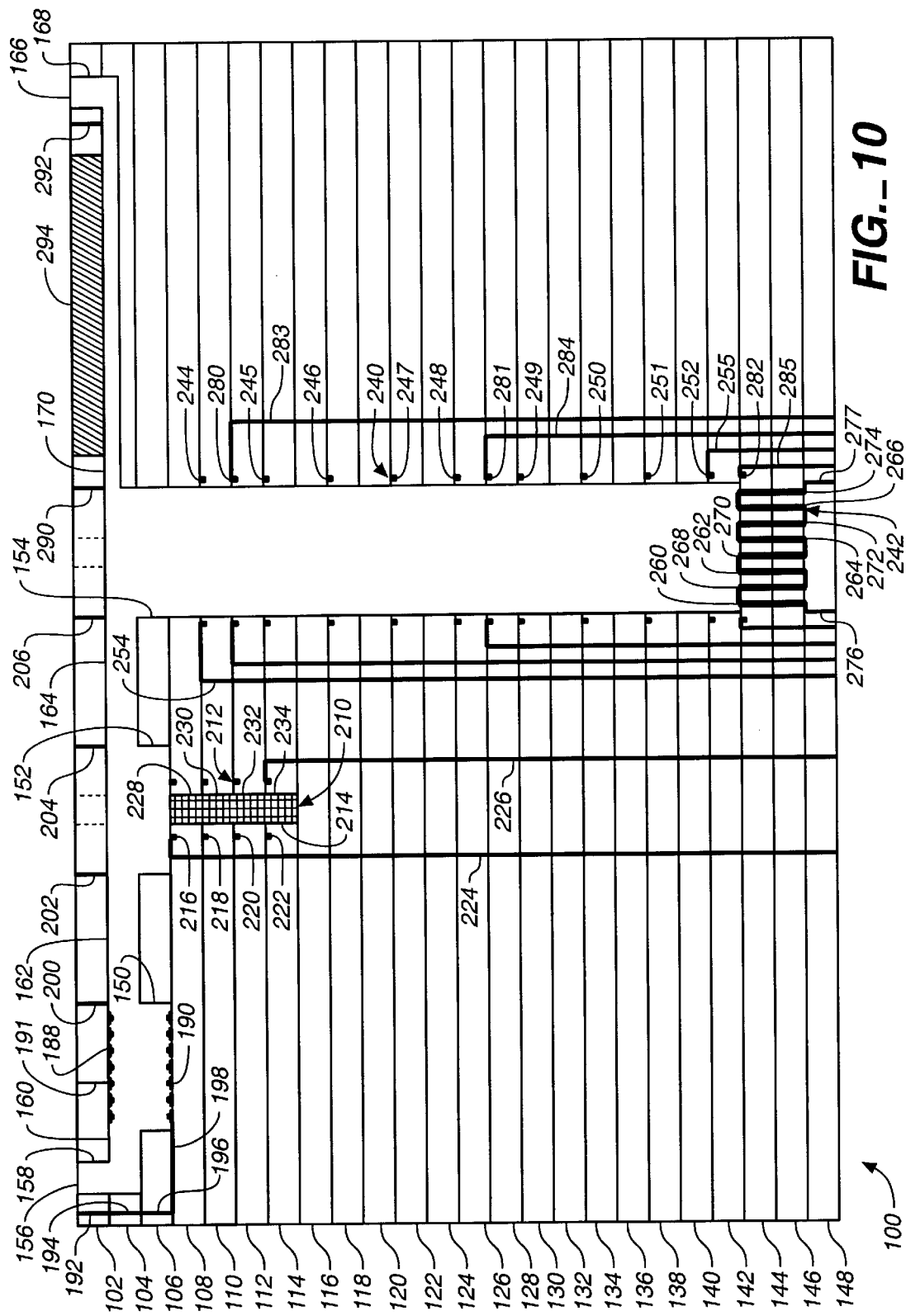
FIG._10

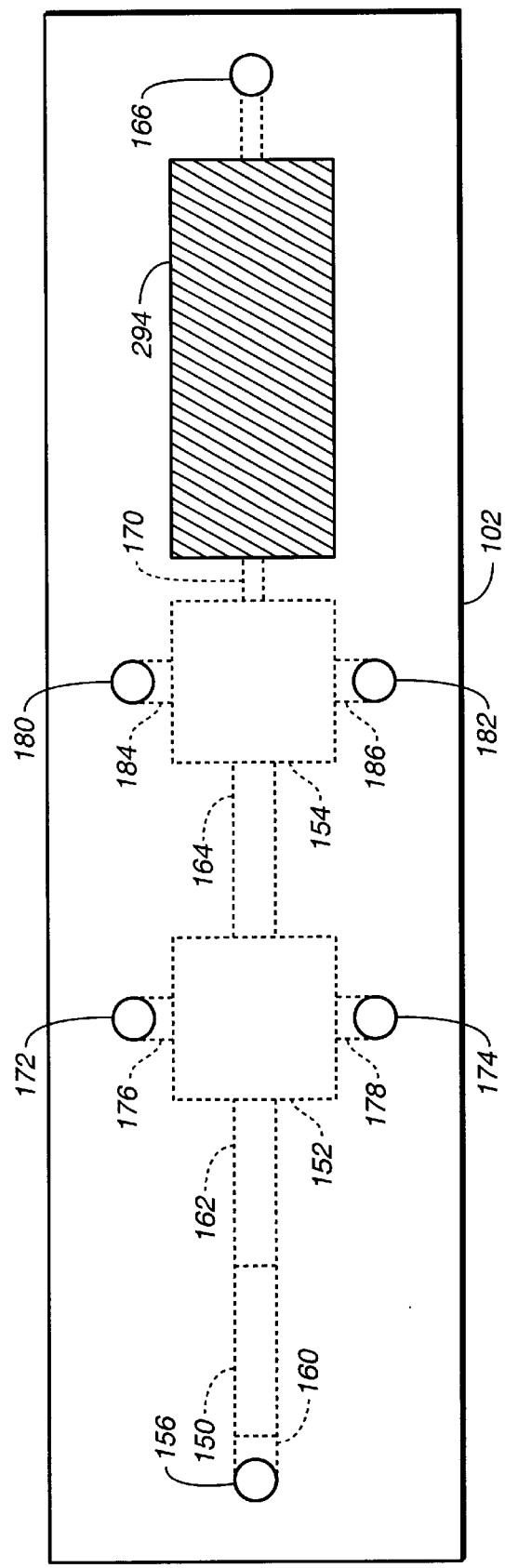
FIG._10A

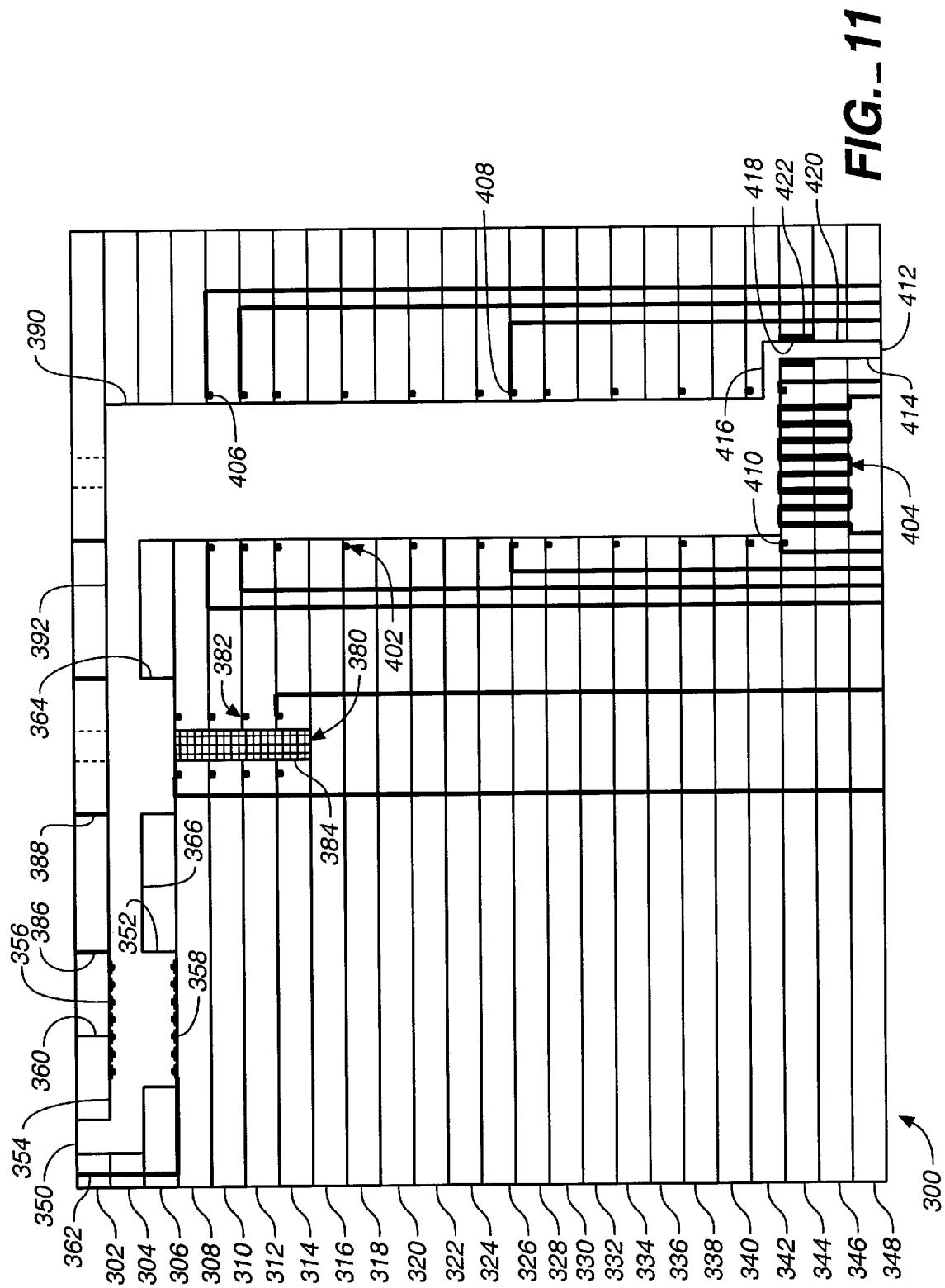

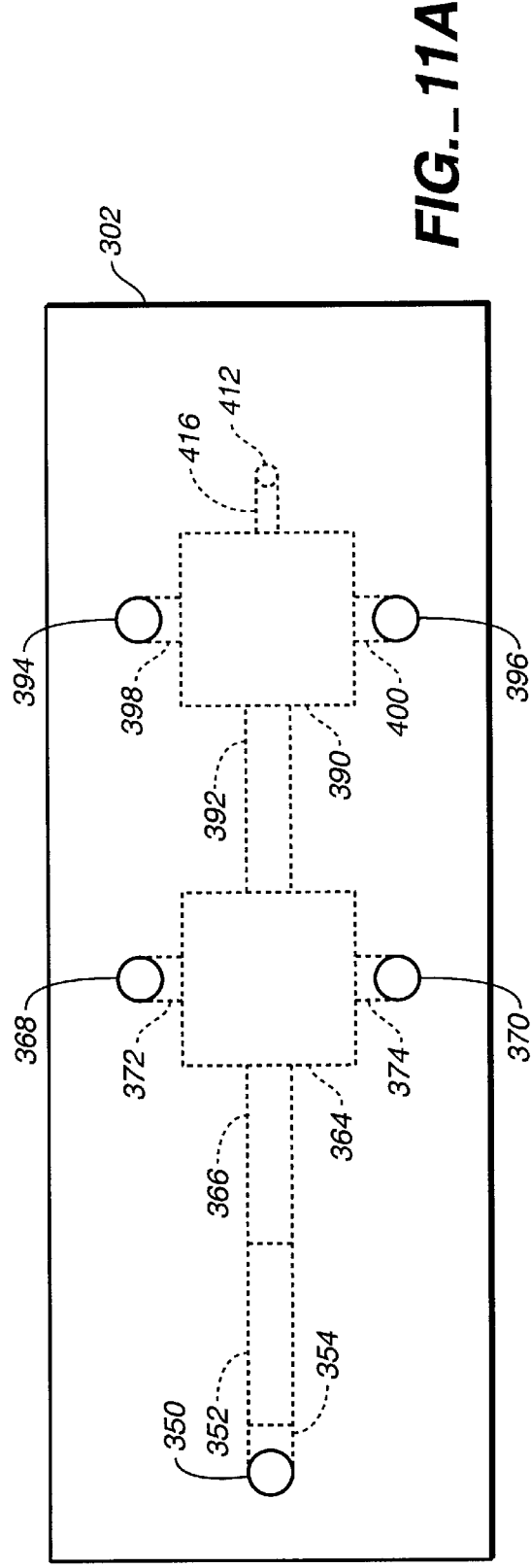
FIG._11A
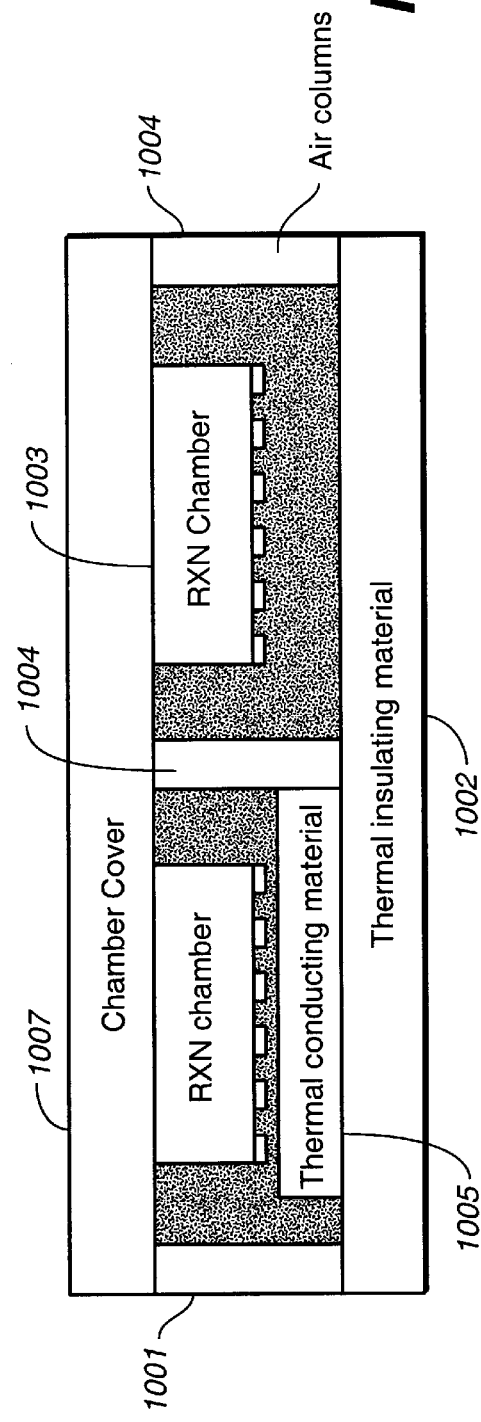
FIG._12

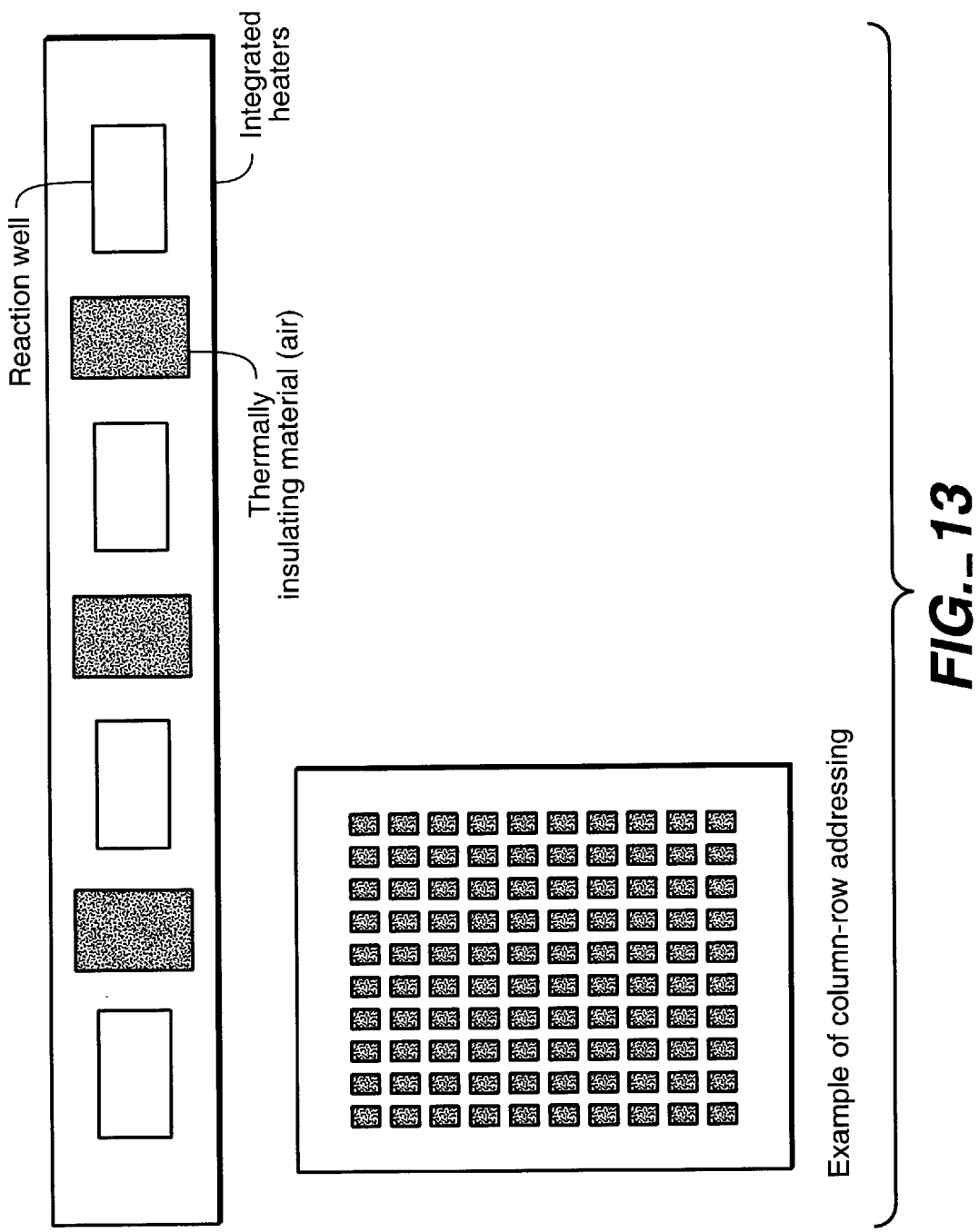
FIG._13

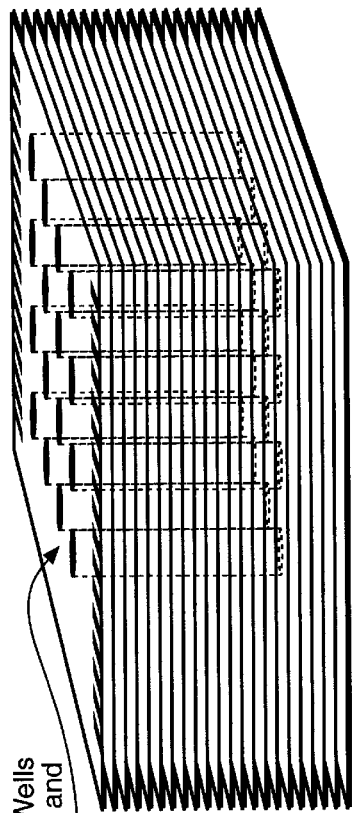
FIG._14A
4 x 4 Array of Reaction Wells with Embedded Heaters and an Embedded RTD
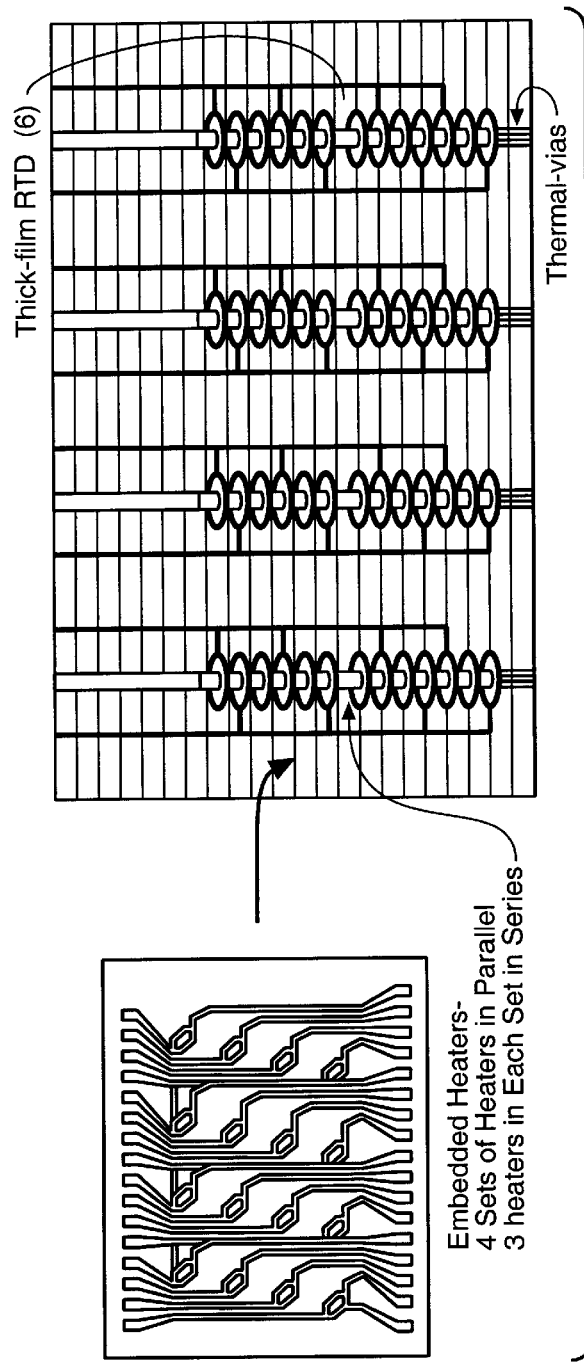
FIG._14B
Thick-film RTD (6)
Thermal-vias
Embedded Heaters- 4 Sets of Heaters in Parallel 3 heaters in Each Set in Series

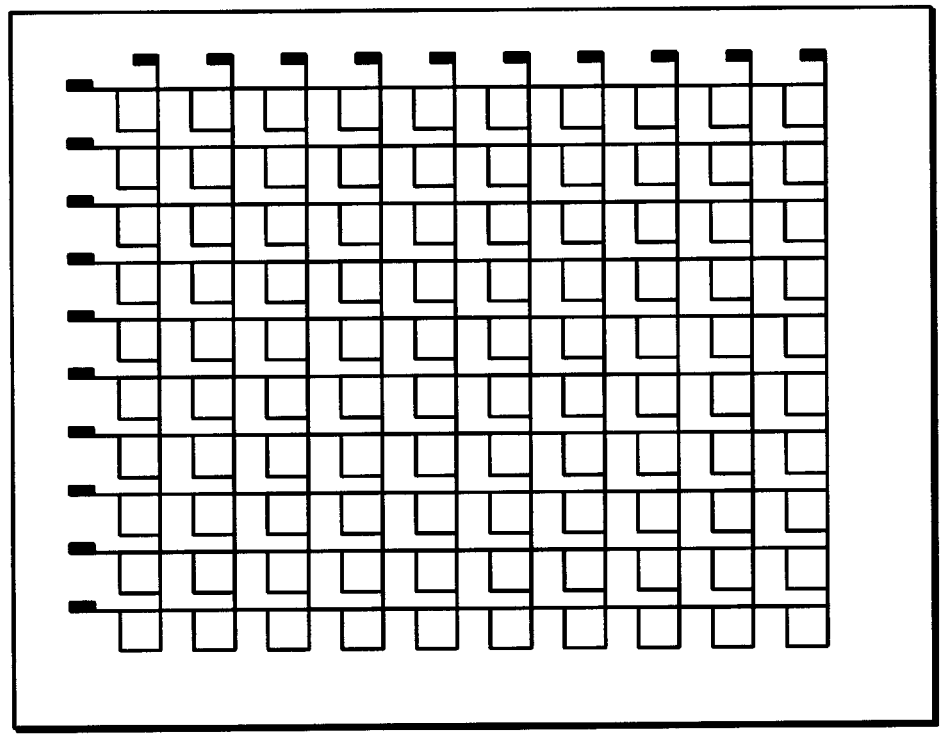
FIG._15
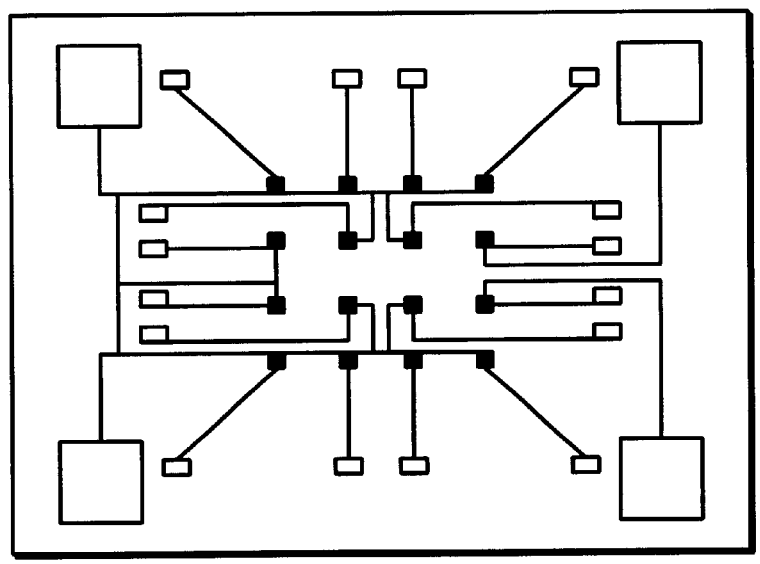
FIG._16

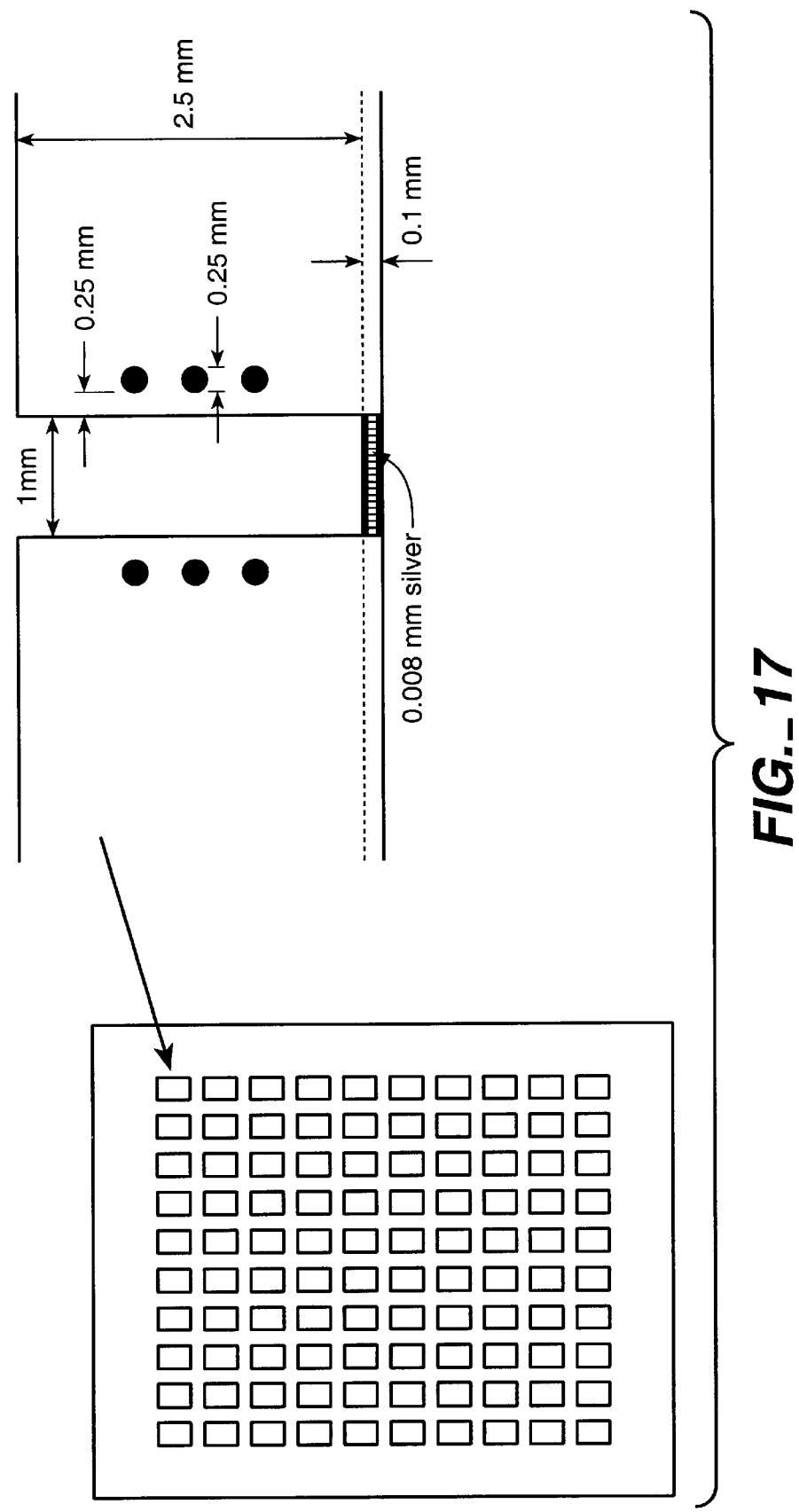
FIG._17

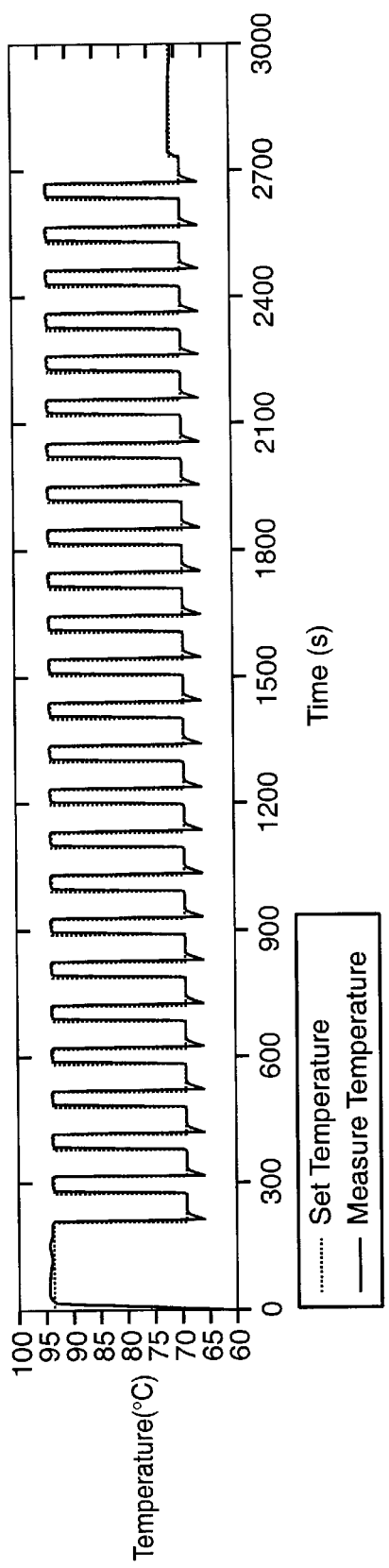
FIG._18A
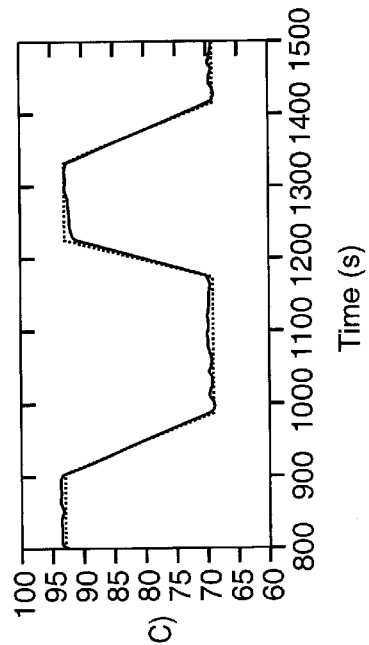
FIG._18C
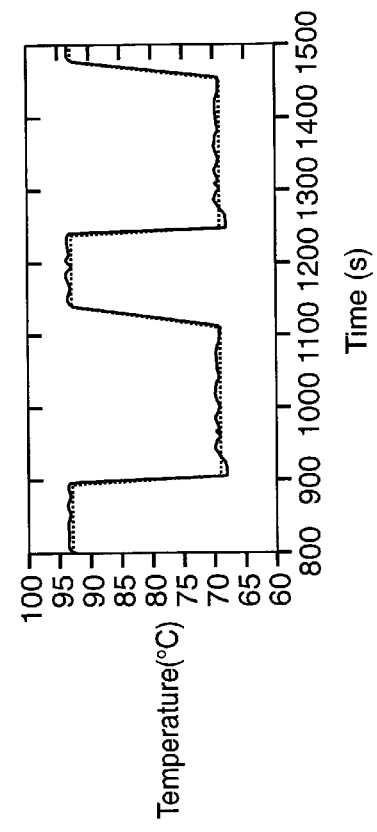
FIG._18B

FIG._19

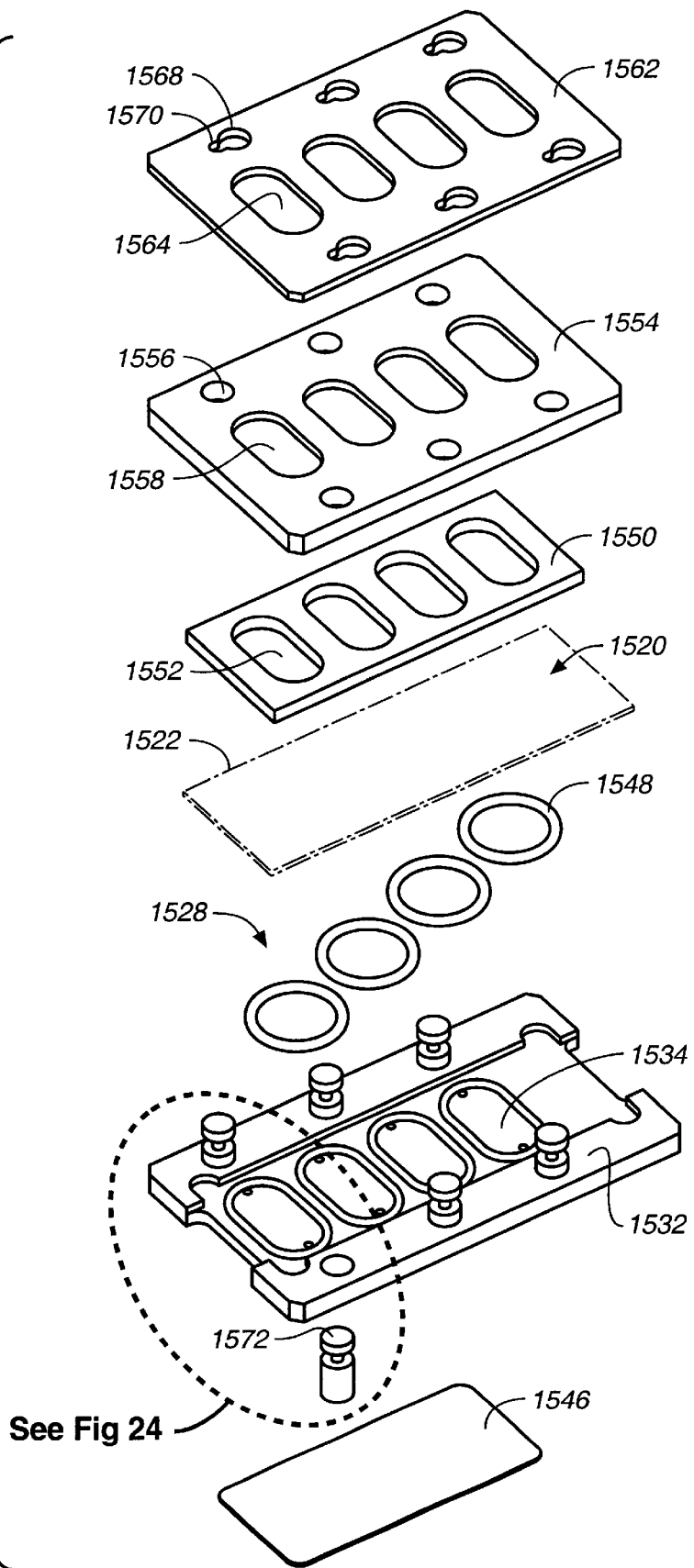
FIG._20

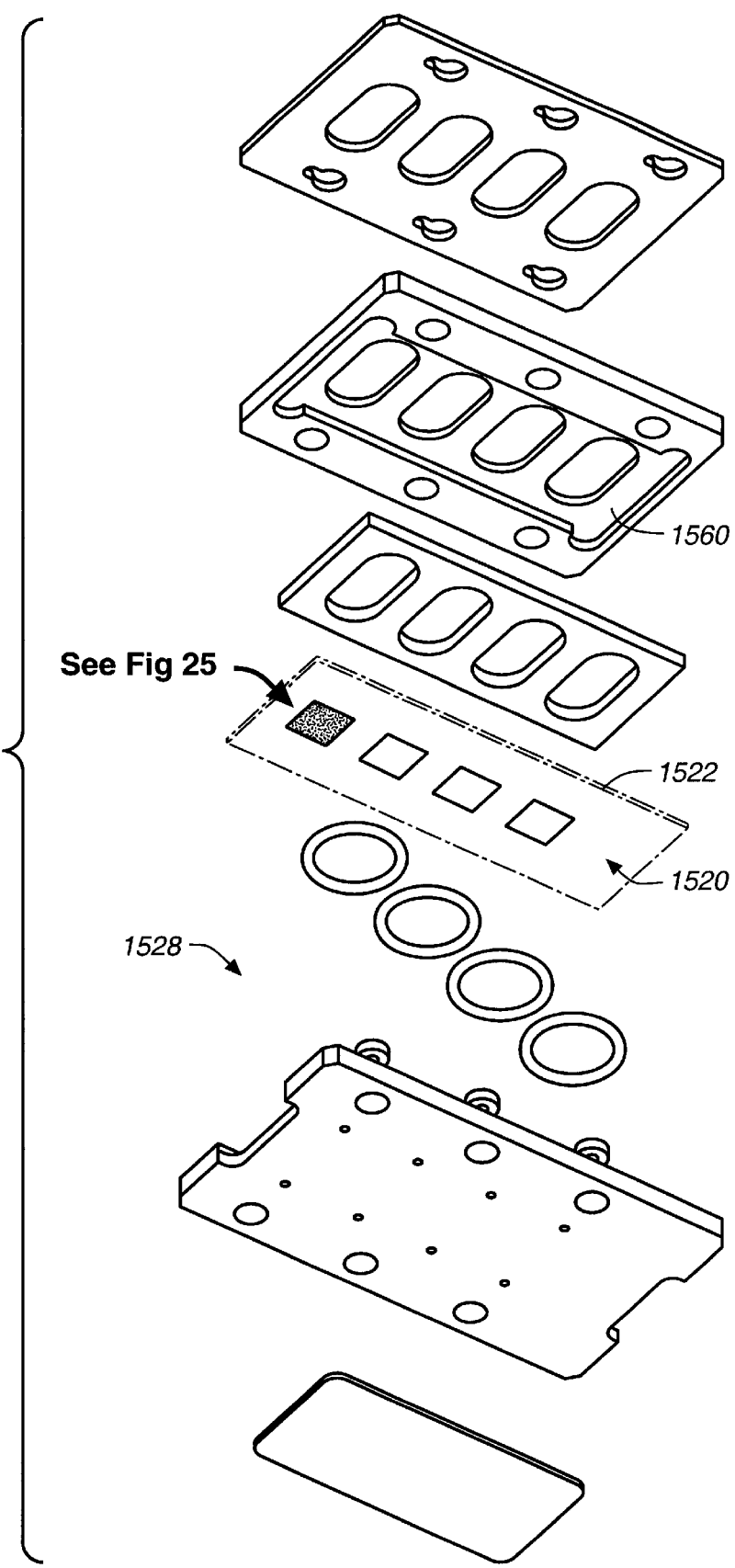
FIG._21

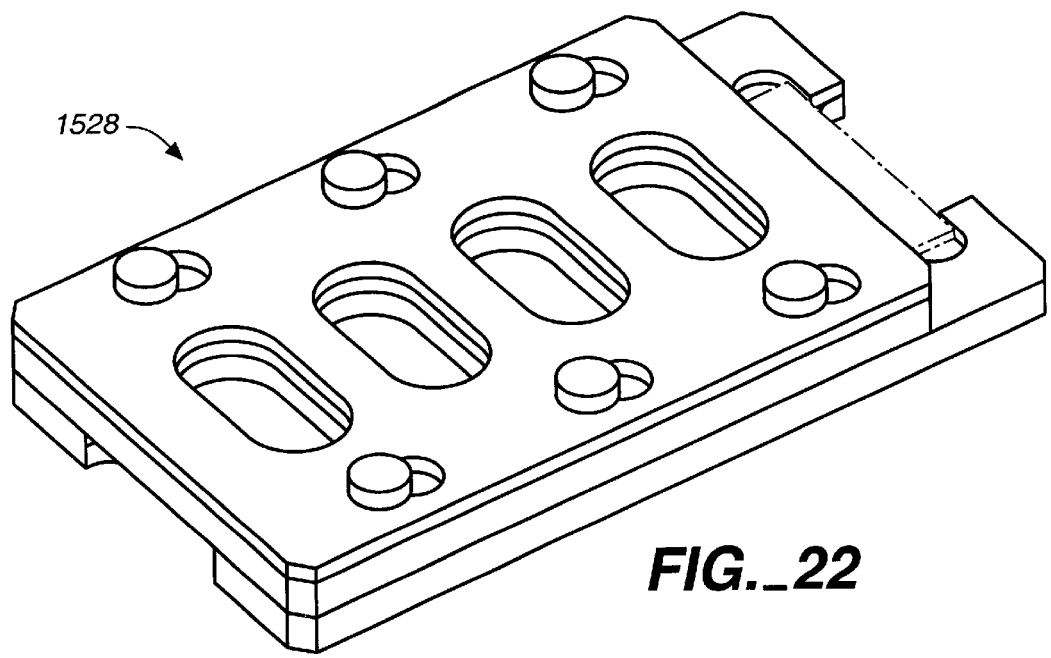
FIG._22
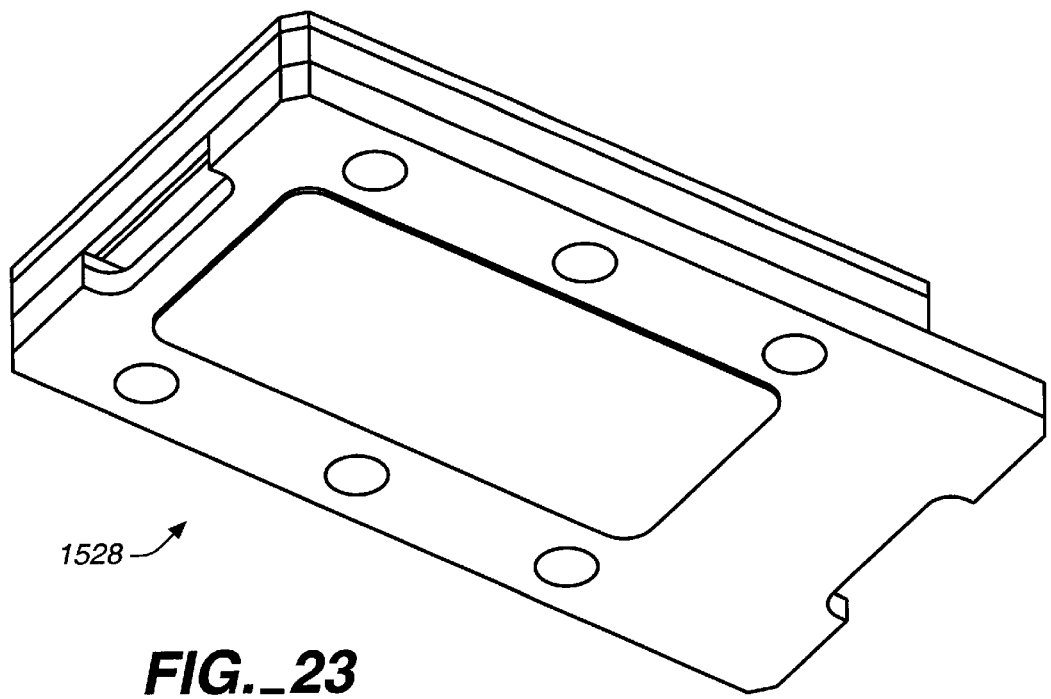
FIG._23

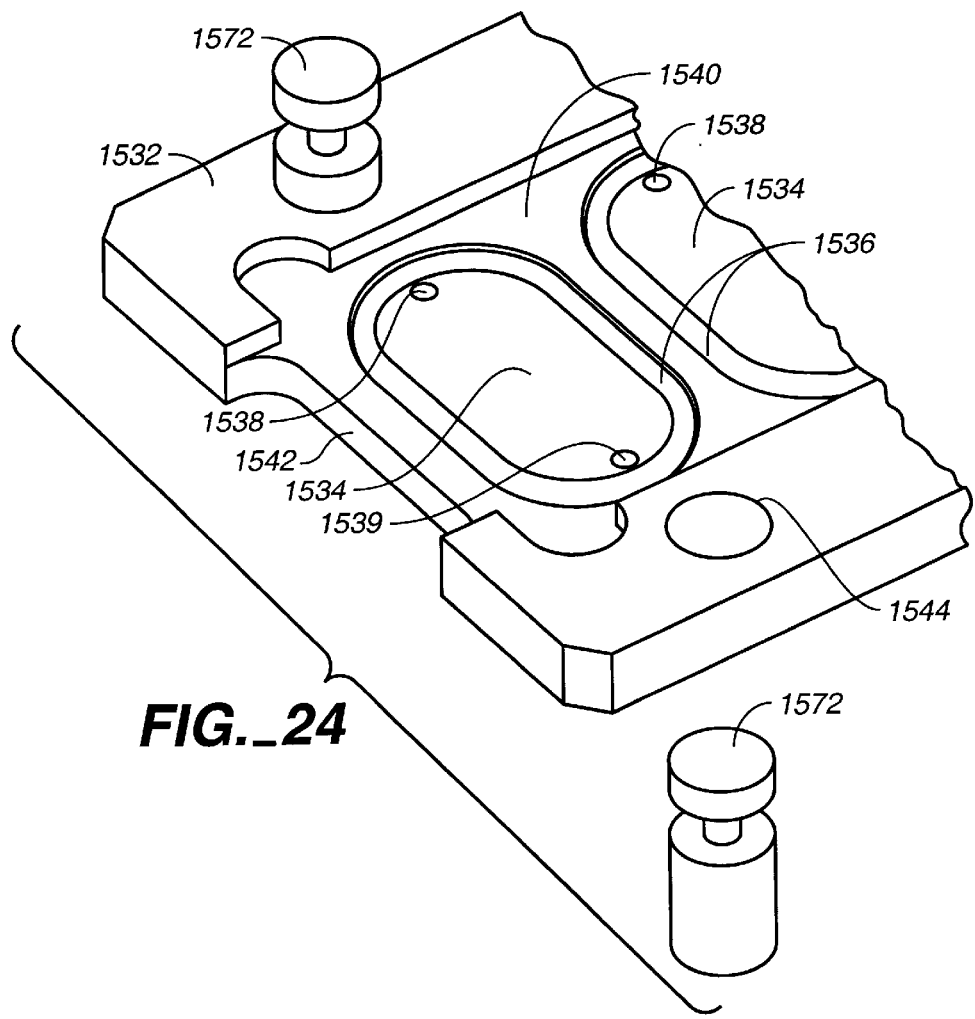
FIG._24
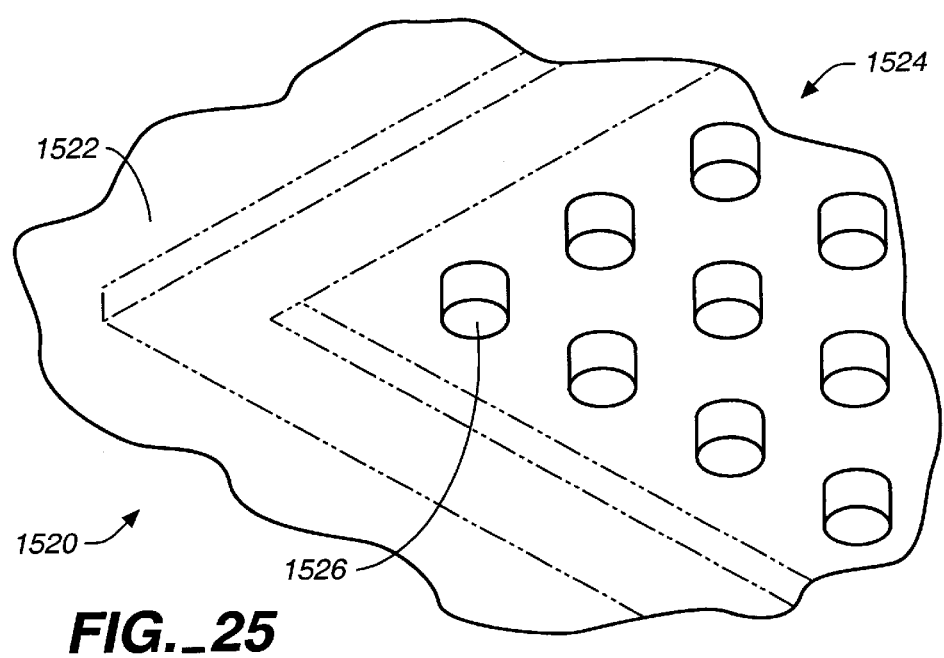
FIG._25

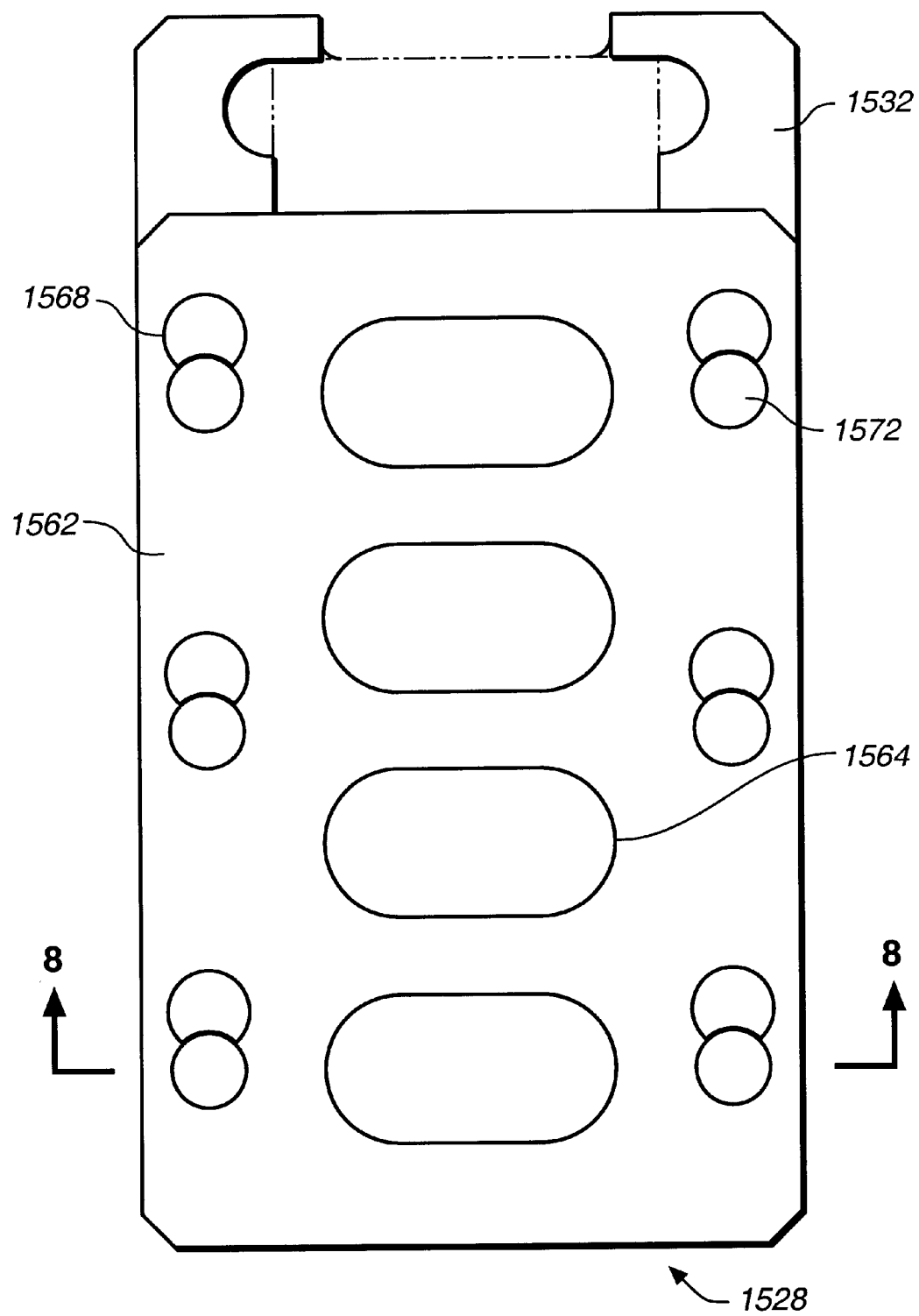
FIG._26

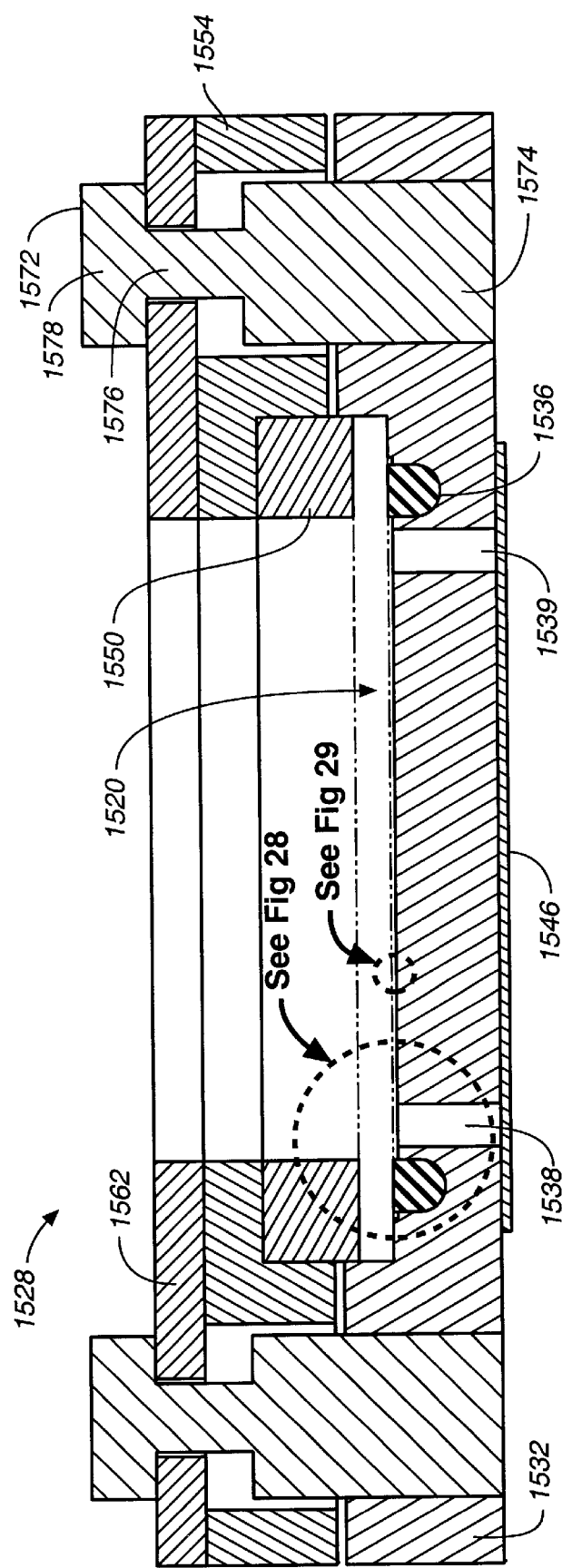
FIG._27

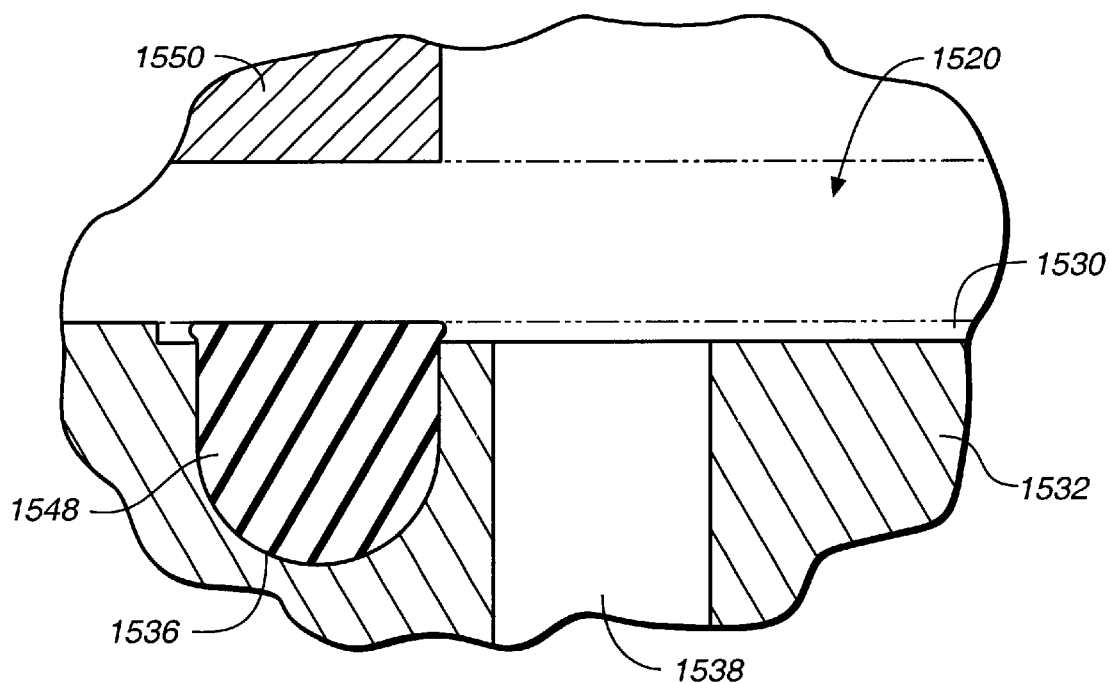
FIG._28
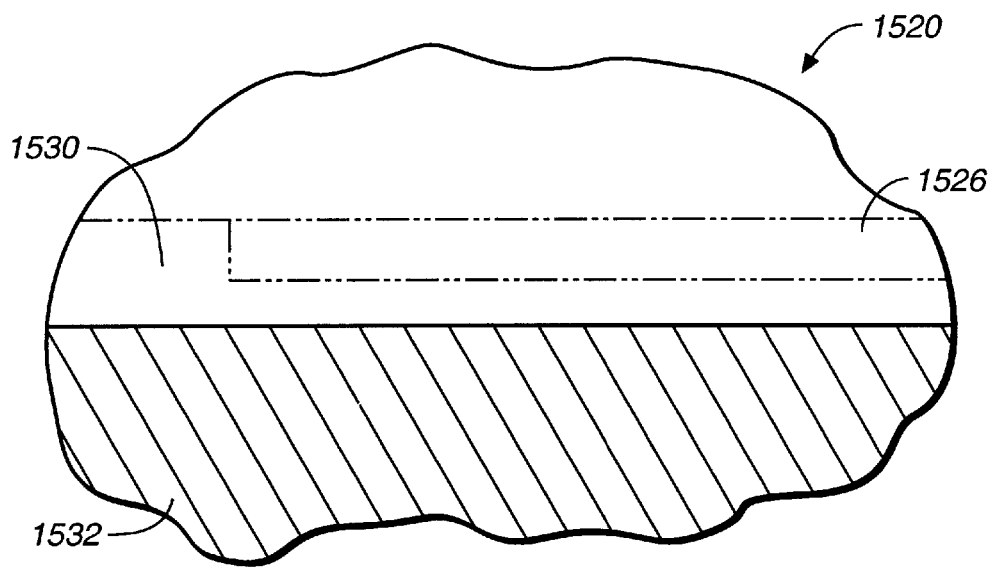
FIG._29

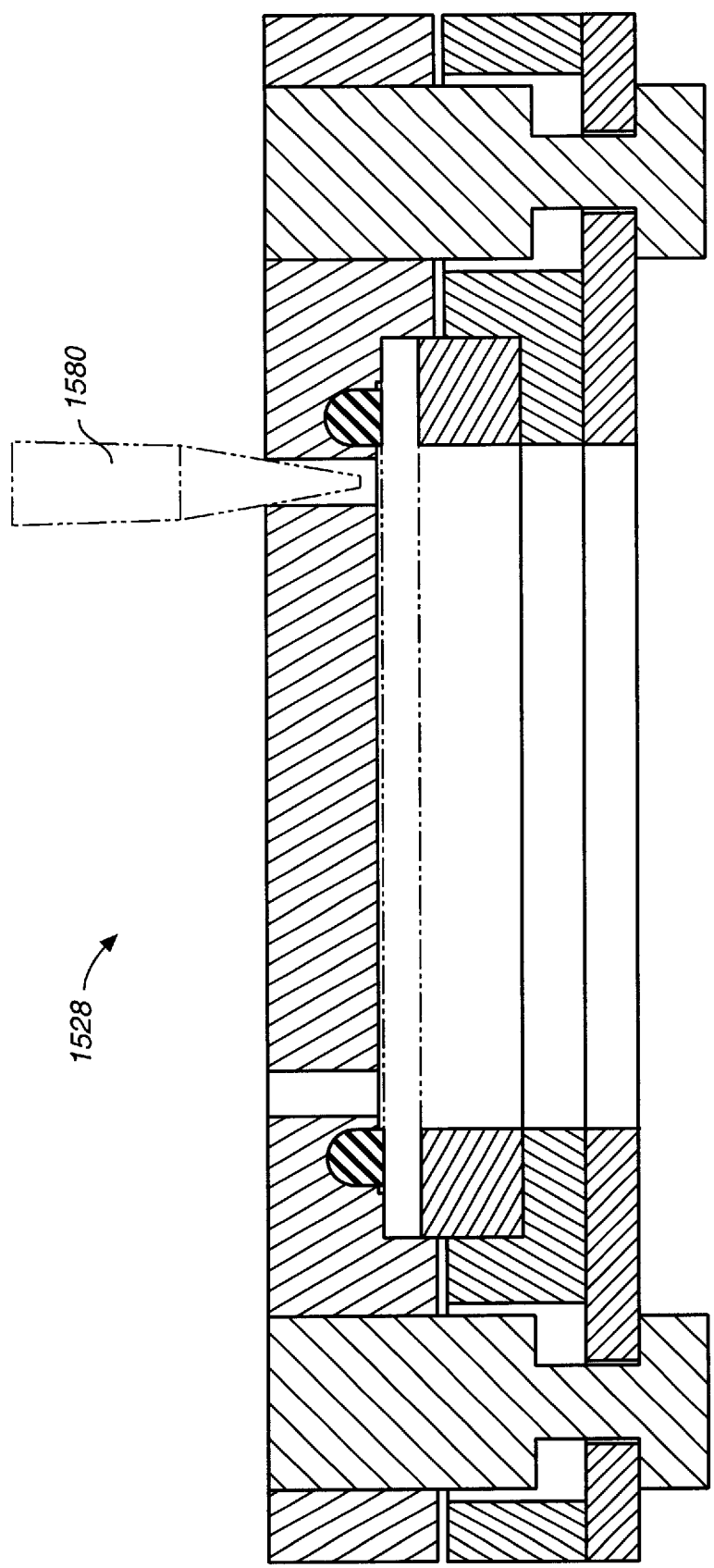
FIG._30

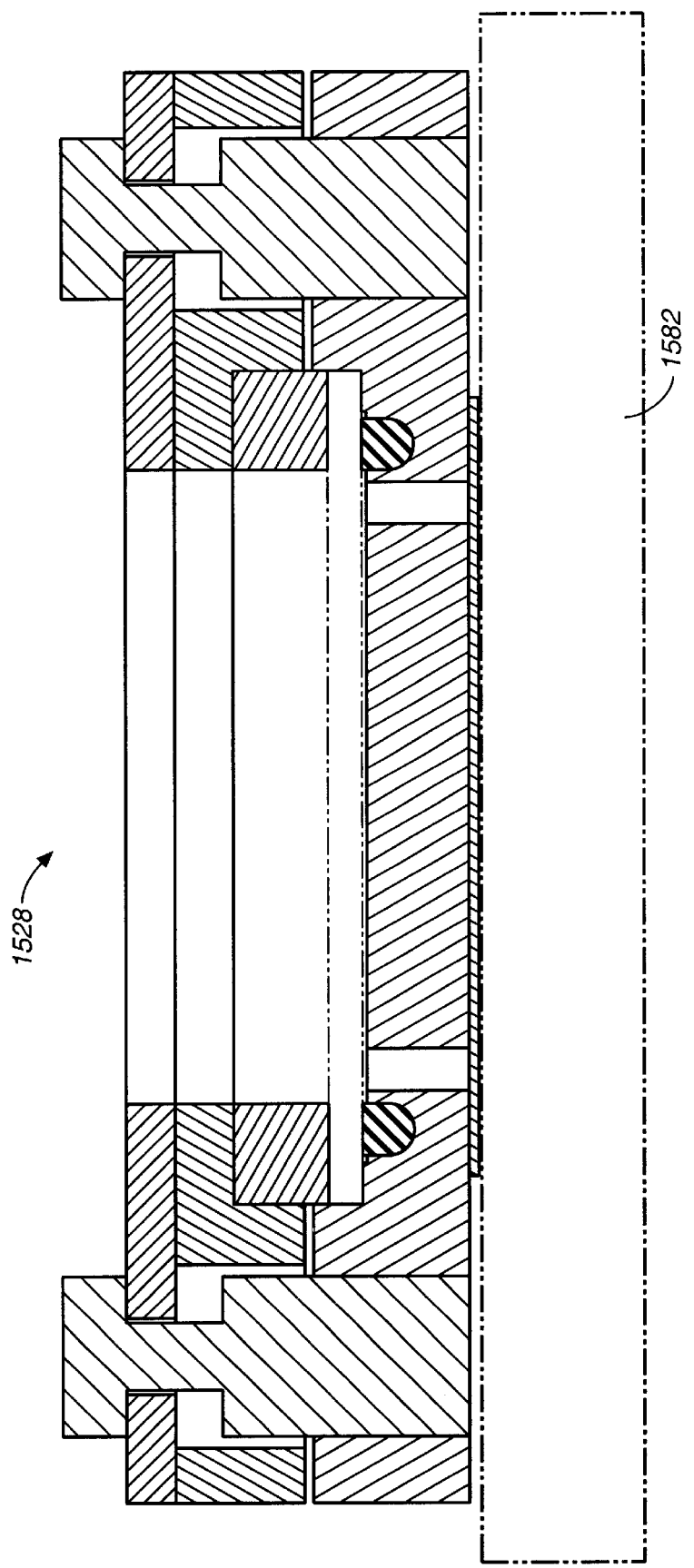
FIG._31

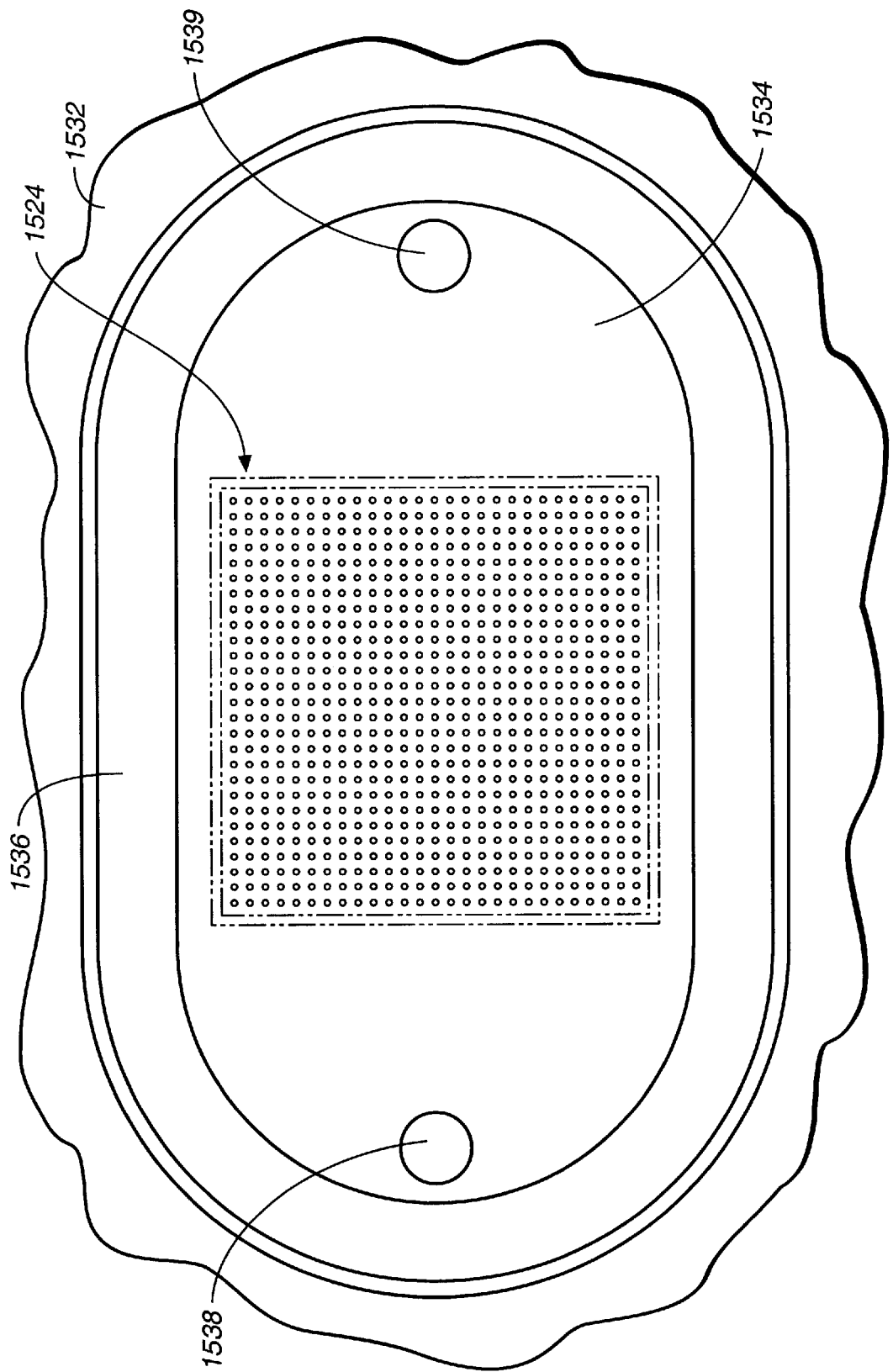
FIG._32

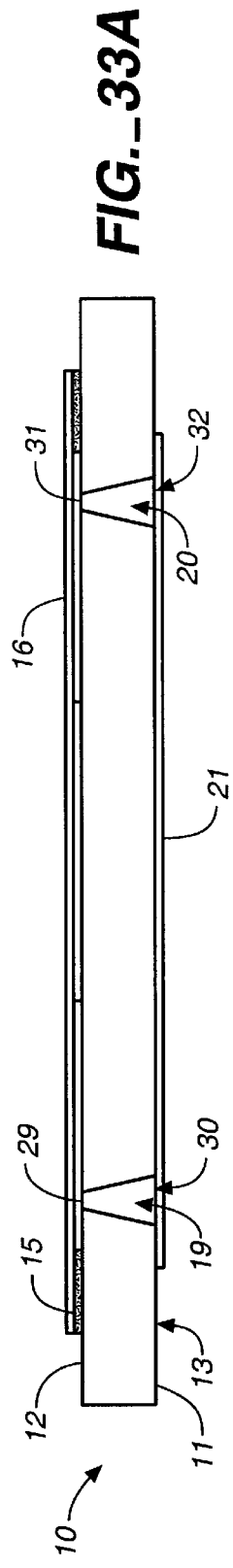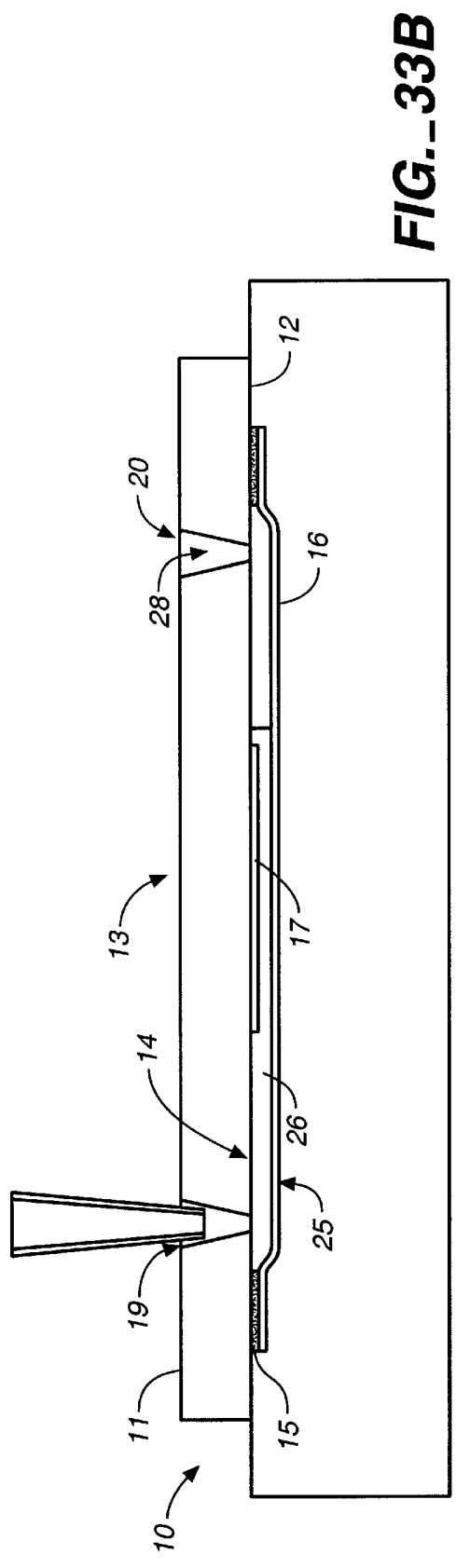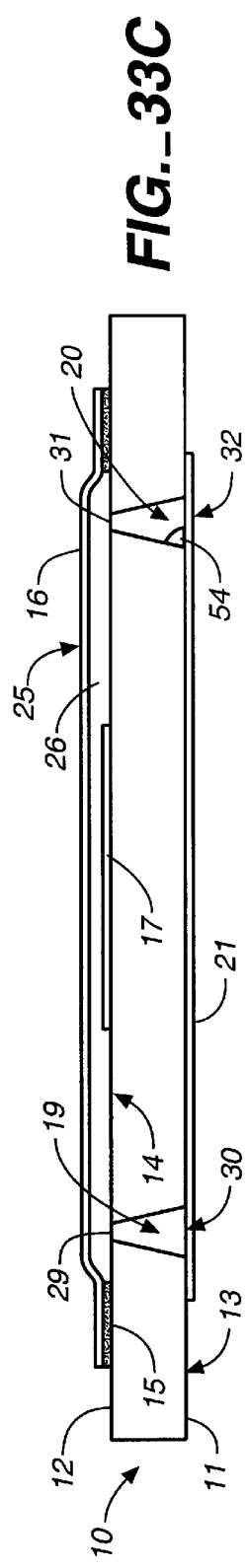

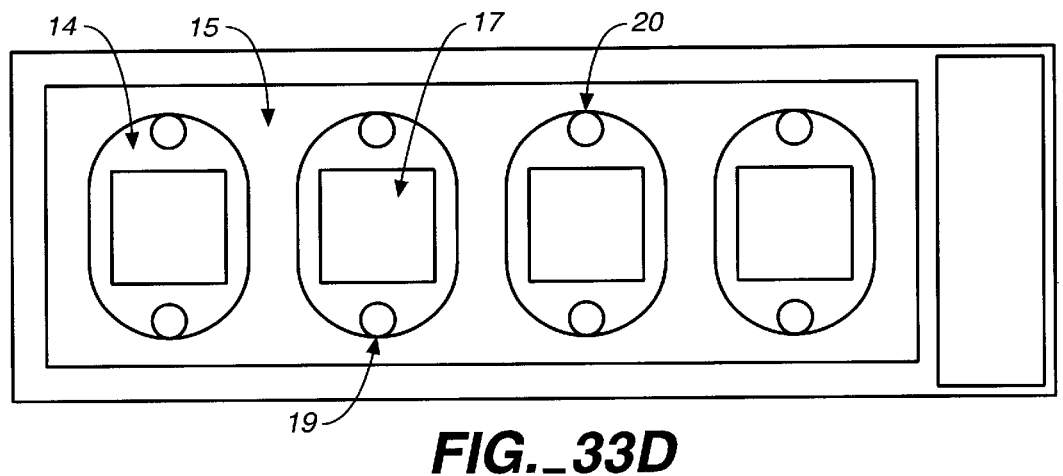
FIG._33D
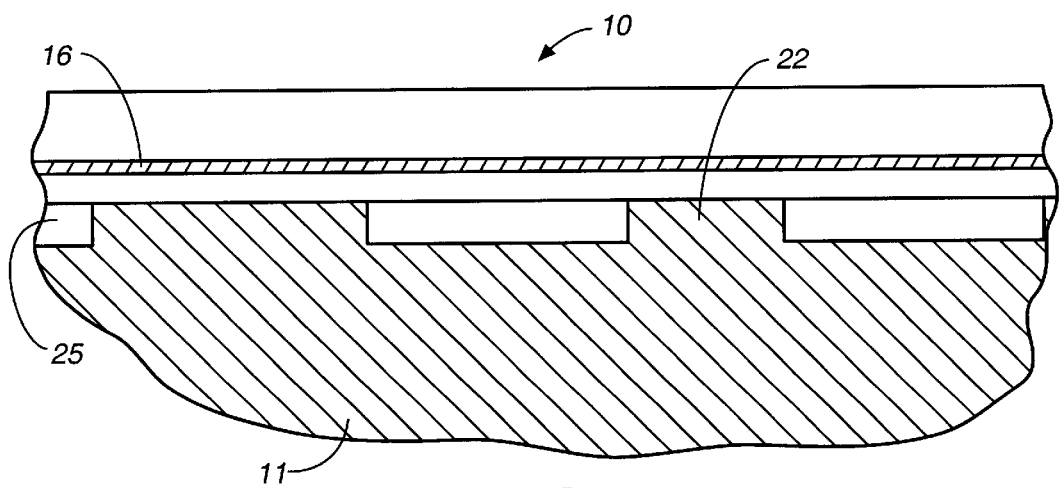
FIG._34

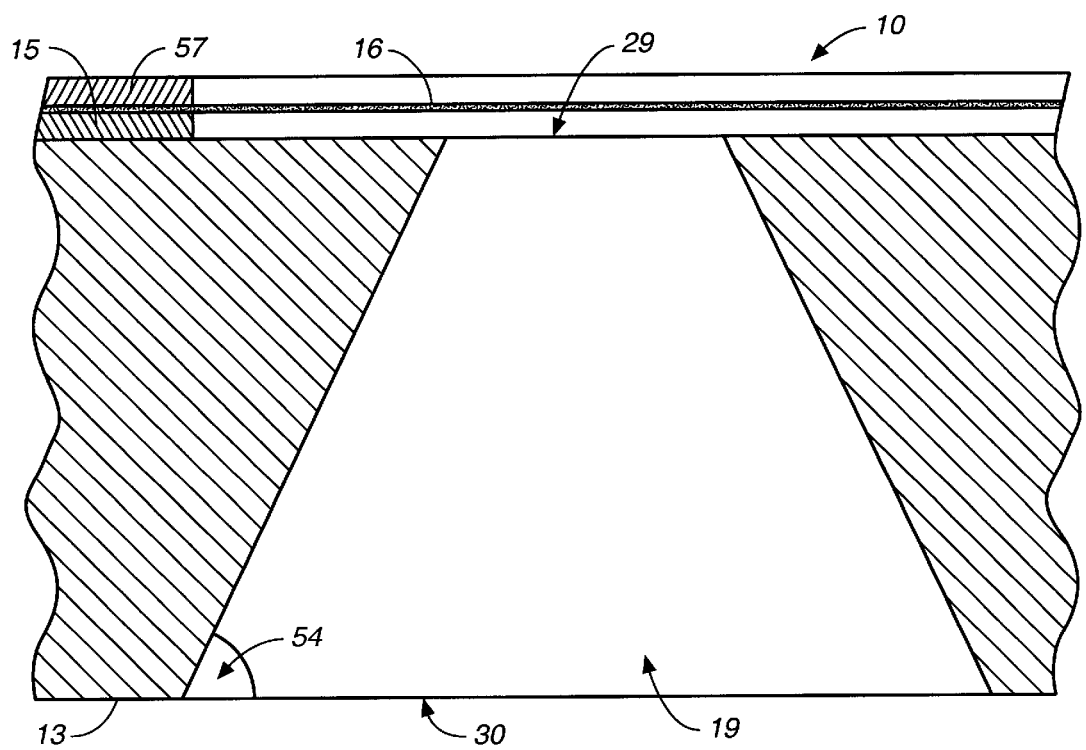
FIG._35

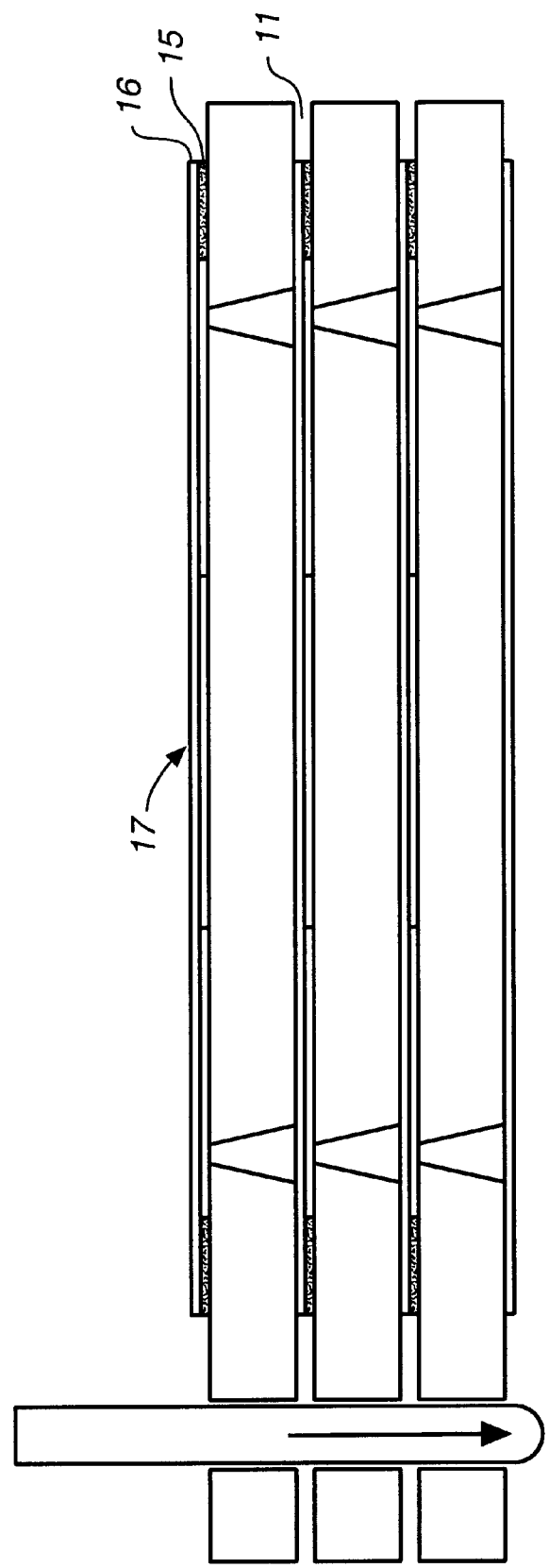
FIG._36

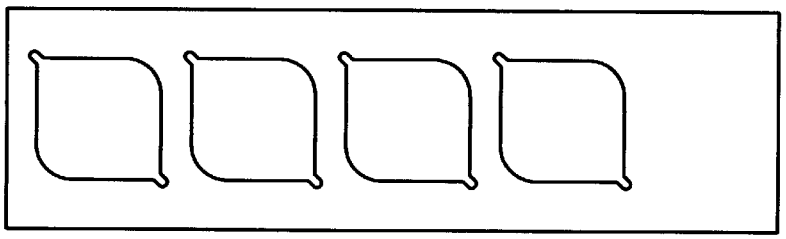
bottom adhesive layer
FIG._37A
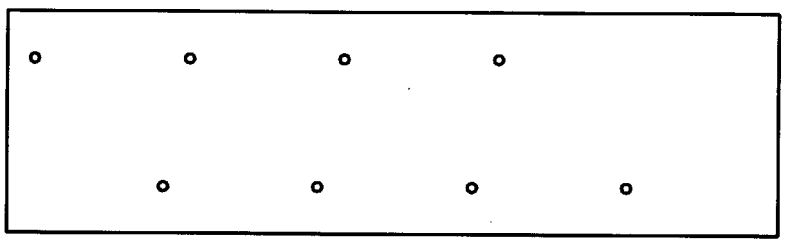
film layer
FIG._37B
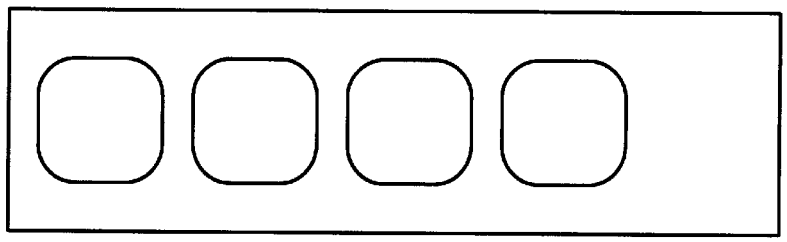
upper adhesive layer
FIG._37C
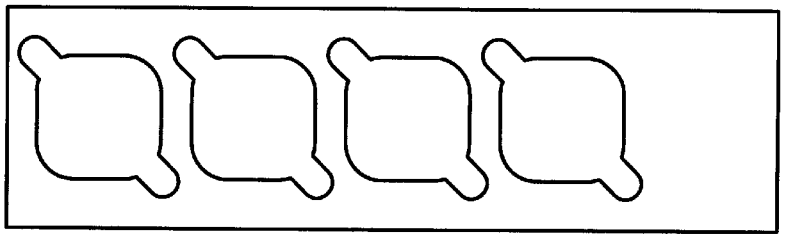
Label frame
FIG._37D
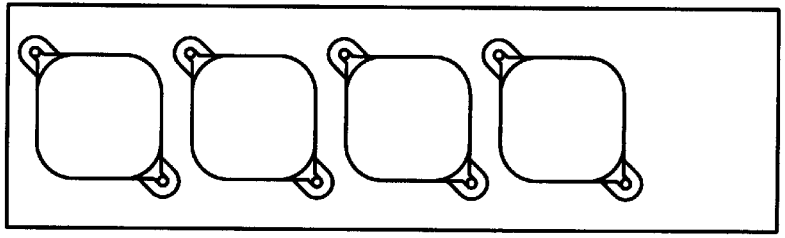
assembled label
FIG._37E

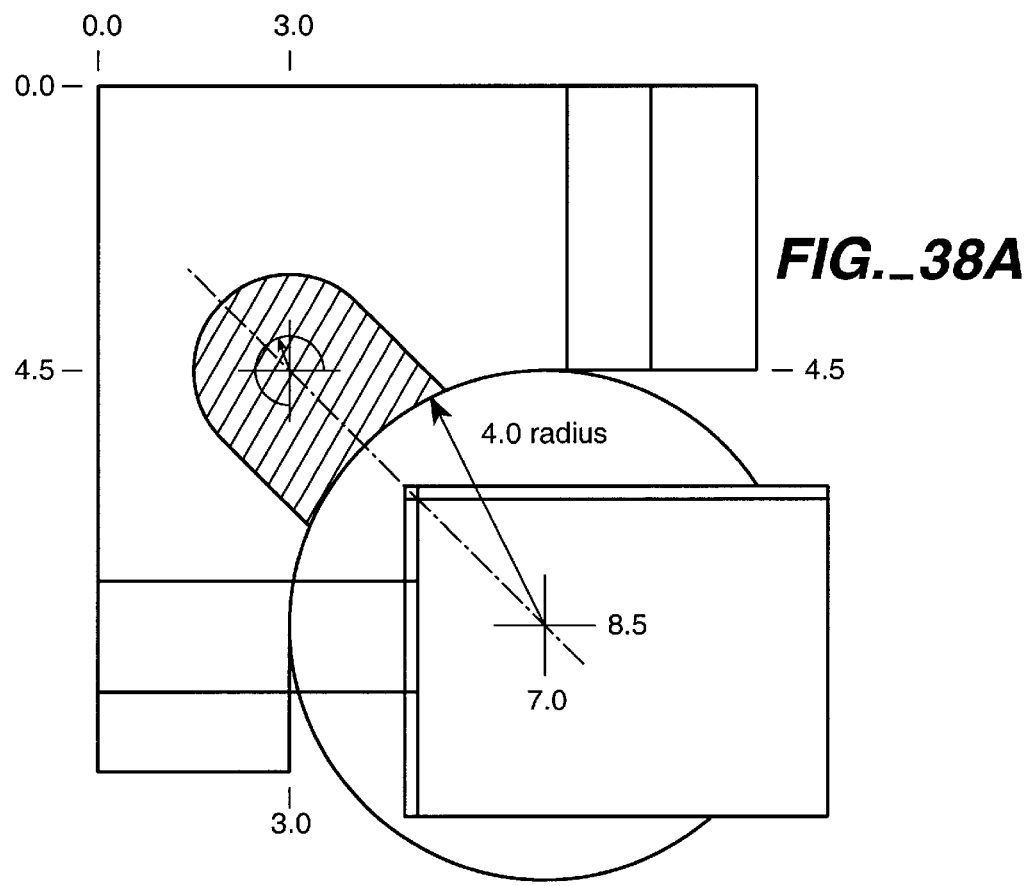
*FIG._38A*
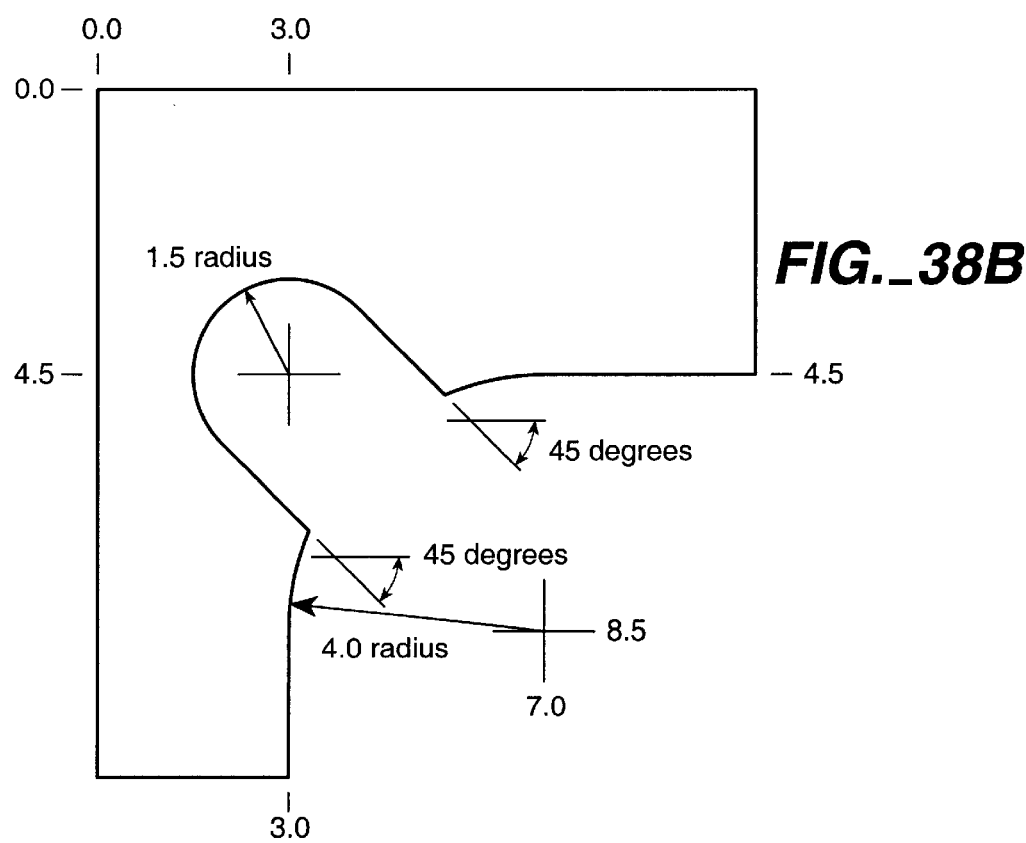
*FIG._38B*

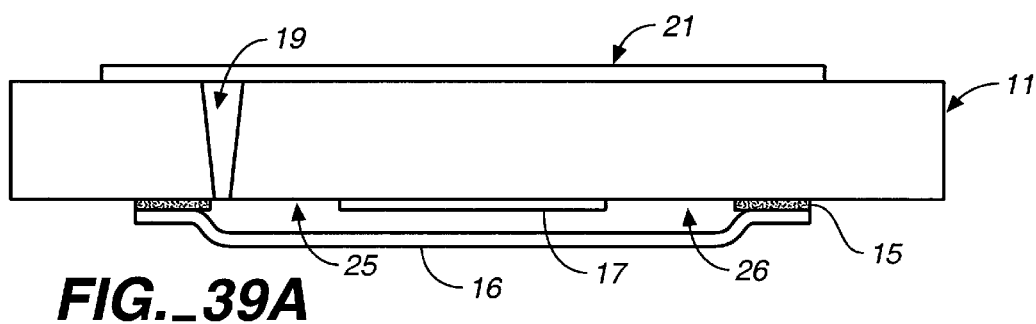
FIG._39A
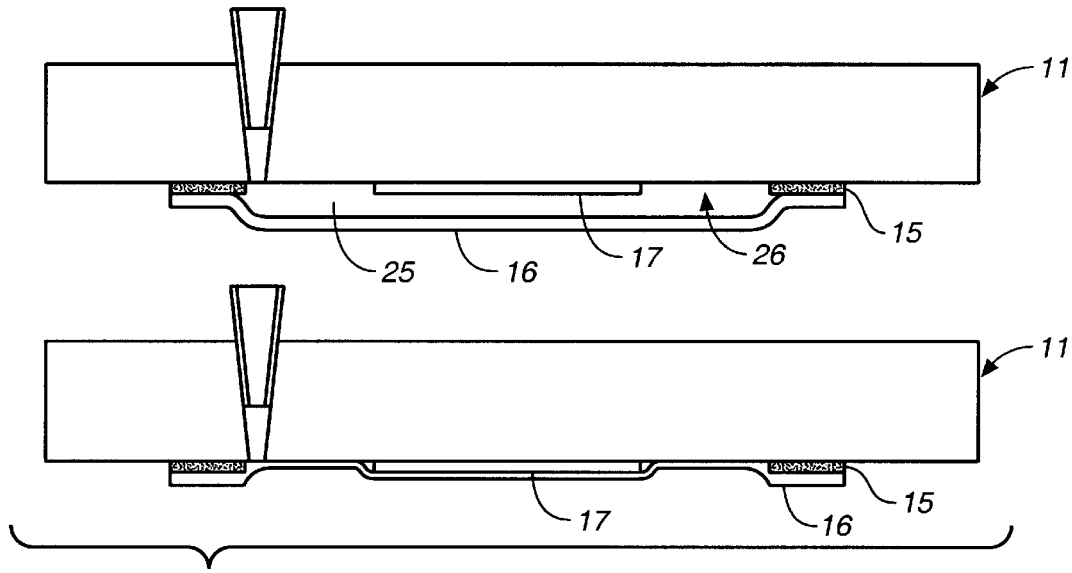
FIG._39B
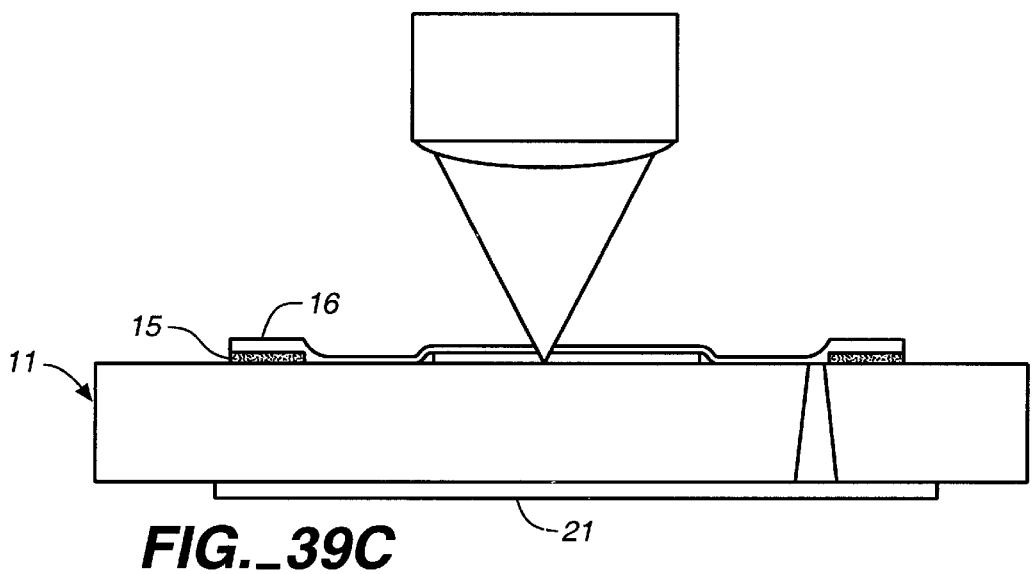
FIG._39C

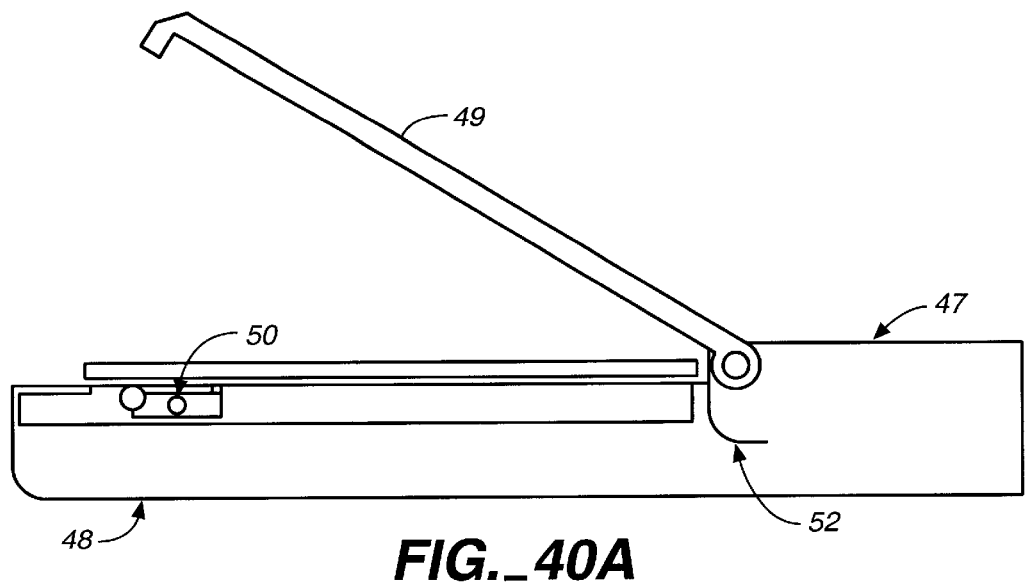
FIG._40A
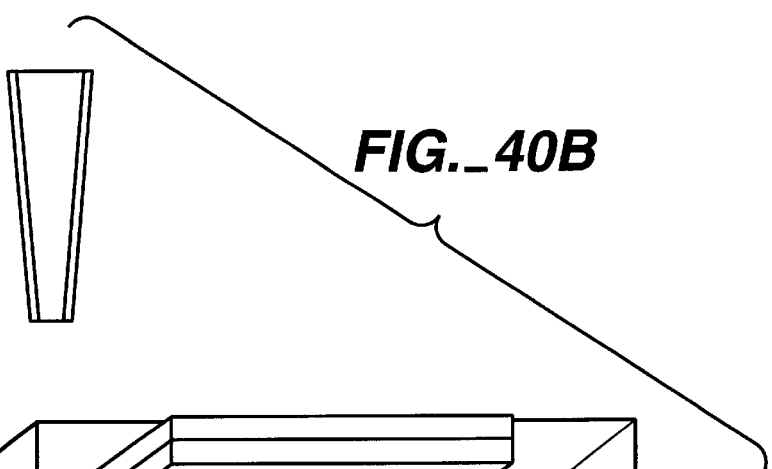
FIG._40B
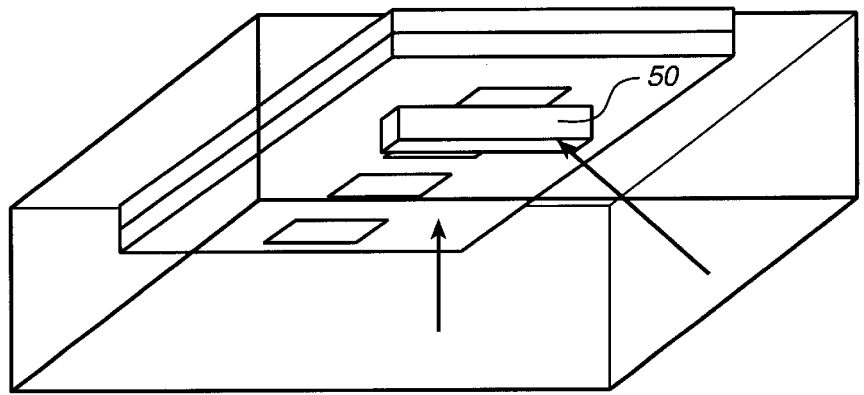

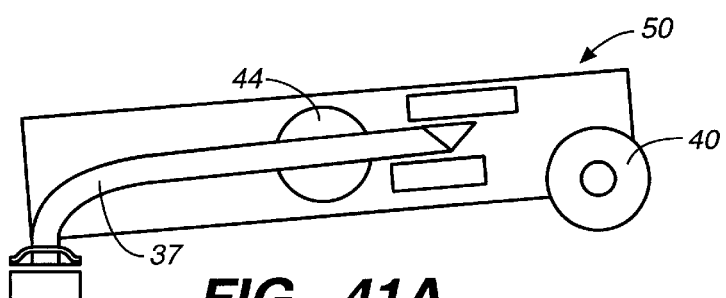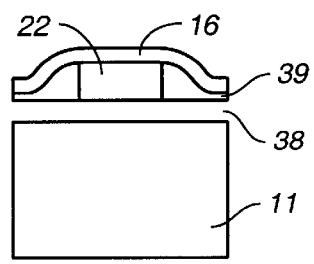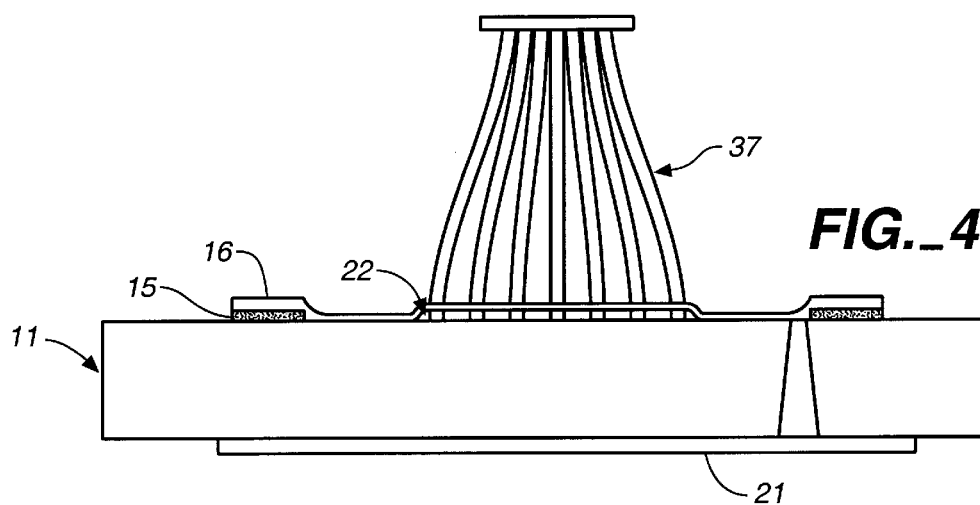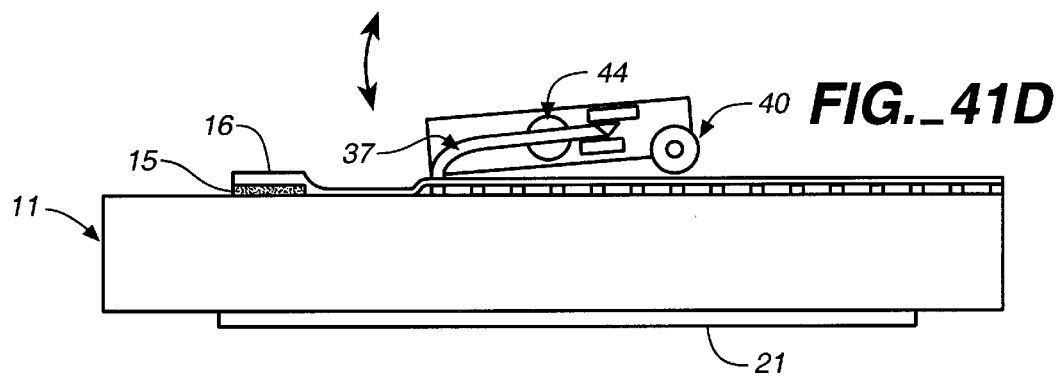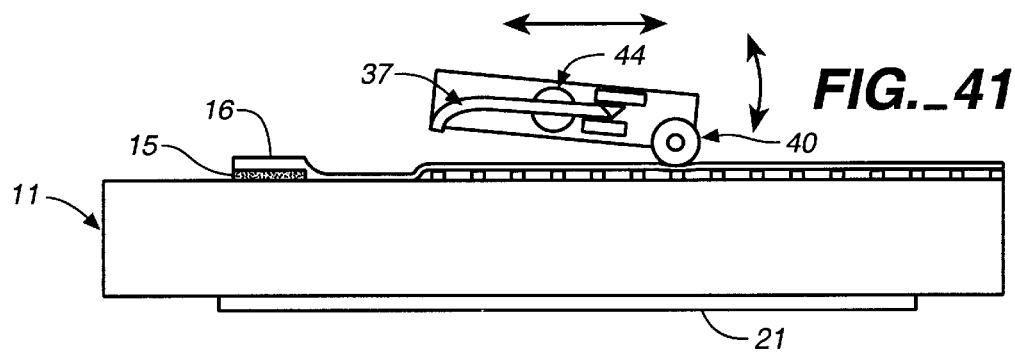

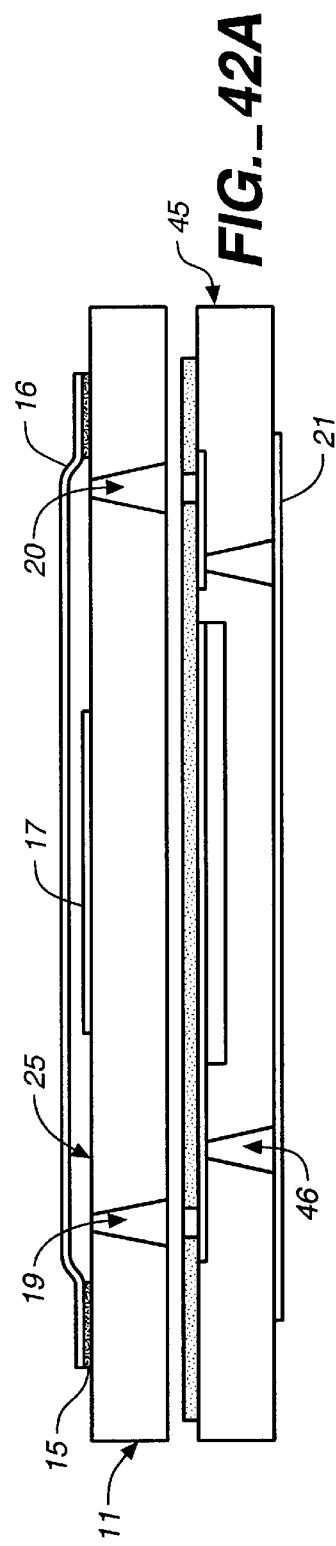
FIG._42A
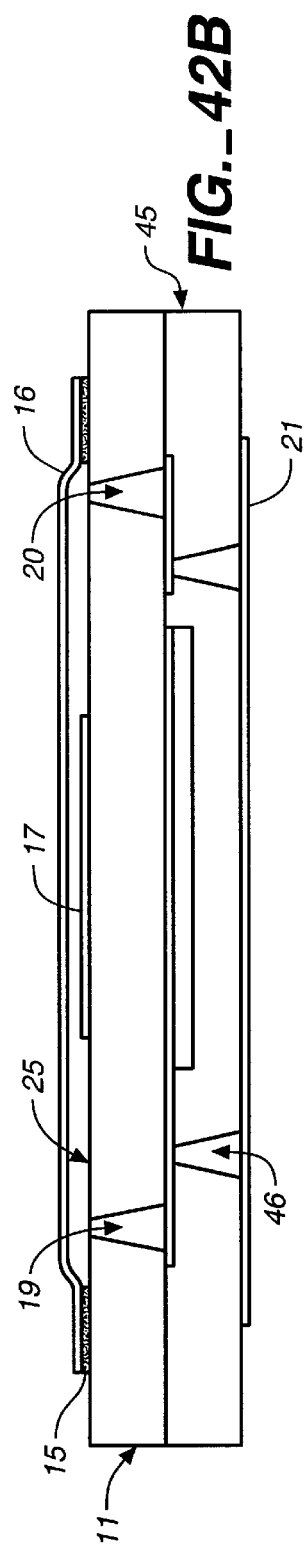
FIG._42B
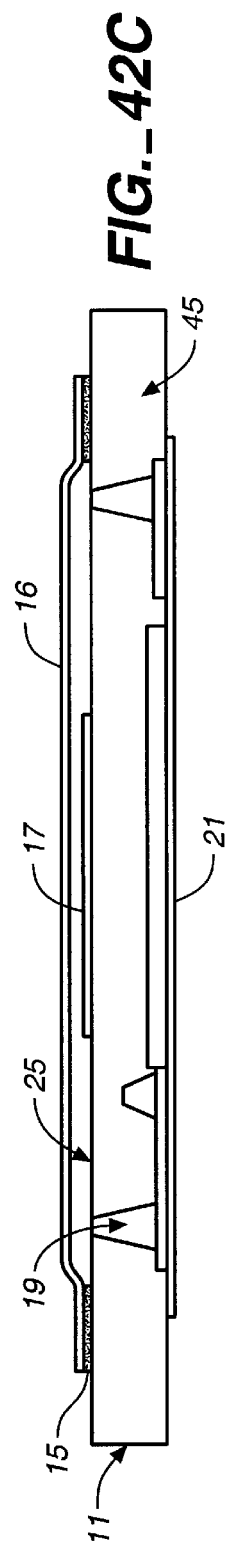
FIG._42C

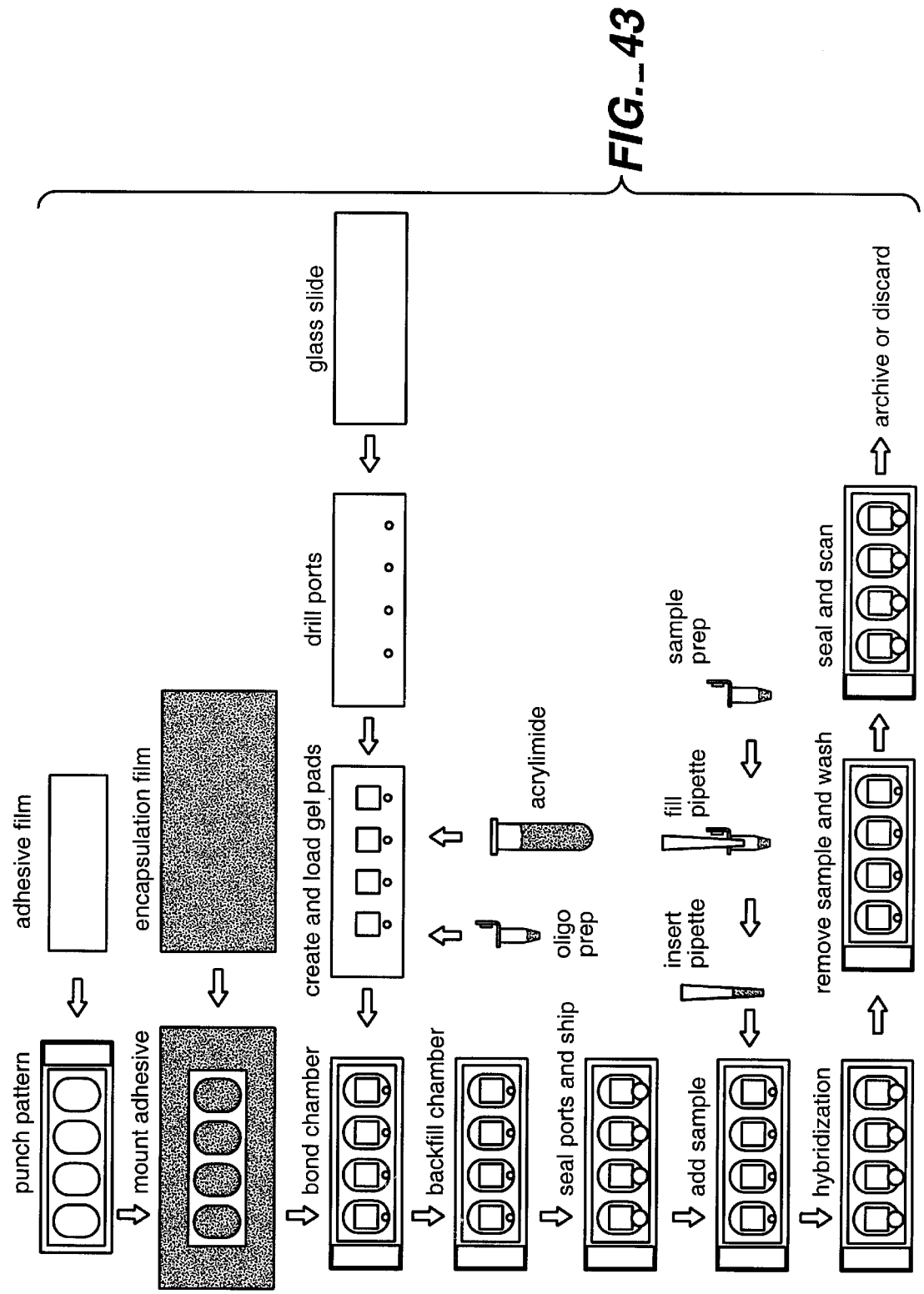
FIG._43

MICROFLUIDIC DEVICES COMPRISING BIOCHANNELS

FIELD OF THE INVENTION

The invention pertains to the structure, fabrication of a microfluidic device and methods for conducting analysis in microfluidic devices. These devices preferably comprise flow-through biochannels comprising a plurality of capture binding ligands.

BACKGROUND OF THE INVENTION

Recent advances in molecular biology have provided the opportunity to identify pathogens, diagnose disease states, and perform forensic determinations using gene sequences specific for the desired purpose. This explosion of genetic information has created a need for high-capacity assays and equipment for performing molecular biological assays, particularly nucleic acid hybridization assays. Most urgently, there is a need to miniaturize, automate, standardize and simplify such assays. This need stems from the fact that while these hybridization assays were originally developed in research laboratories working with purified products and performed by highly skilled individuals, adapting these procedures to clinical uses, such as diagnostics, forensics and other applications, has produced the need for equipment and methods that allow less-skilled operators to effectively perform the assays under higher capacity, less stringent assay conditions.

Existing technology utilizes the binding of molecules contained within a biologically reactive sample fluid, hereinafter referred to as target molecules, onto molecules contained within biologically reactive sites, hereinafter referred to as probe molecules. The primary enabler of this technology is an apparatus commonly referred to as a biochip, which comprises one or more ordered microscopic arrays ("microarrays") of biologically reactive sites immobilized on the surface of a substrate. A biologically reactive site can be created by dispensing a small volume of a fluid containing a biological reagent onto a discrete location on the surface of a substrate, also commonly referred to as spotting. To enhance immobilization of probe molecules, biochips can include a 2-dimensional array of 3-dimensional polymeric anchoring structures (for example, polyacrylamide gel pads) attached to the surface of the substrate. Probe molecules such as oligonucleotides are covalently attached to polyacrylamide-anchoring structures by forming amide, ester or disulfide bonds between the biomolecule and a derivatized polymer comprising the cognate chemical group. Covalent attachment of probe molecules to such polymeric anchoring structures is usually performed after polymerization and chemical cross-linking of the polymer to the substrate is completed.

Of particular interest are methods of analyzing the nucleic acid in a sample of cells. The conventional way of analyzing the nucleic acid present in a sample of cells involves performing multiple steps using several different bench top instruments in a laboratory setting. First, the nucleic acid must be extracted from the cells in the sample. This is typically done by performing any number of cell lysing procedures that cause the cells to break apart and release their contents. Next, the nucleic acid is typically separated from the rest of the cell contents, as the presence of other cell contents may be undesirable in subsequent steps. Frequently, a nucleic acid amplification reaction is done to obtain suitable amounts of nucleic acid for characterization. The resulting amplified nucleic acid products can then be identified by any number of techniques.

There are a variety of nucleic acid amplification reactions that are used, some of which utilize thermal cycling. Briefly, these techniques can be classified as either target amplification or signal amplification. Target amplification involves the amplification (i.e. replication) of the target sequence to be detected, resulting in a significant increase in the number of target molecules. Target amplification strategies include the polymerase chain reaction (PCR), strand displacement amplification (SDA), nucleic acid sequence based amplification (NASBA), and transcription mediated amplification (TMA).

Alternatively, rather than amplify the target, alternate techniques use the target as a template to replicate a signalling probe, allowing a small number of target molecules to result in a large number of signalling probes, that then can be detected. Signal amplification strategies include the ligase chain reaction (LCR), cycling probe technology (CPT), Invader™, Q-beta replicase (QBR), and the use of "amplification probes" such as "branched DNA" that result in multiple label probes binding to a single target sequence.

The polymerase chain reaction (PCR) is widely used and described, and involve the use of primer extension combined with thermal cycling to amplify a target sequence. This technique has been applied to a wide variety of biological methods, including for example, DNA sequence analysis, probe generation, cloning of nucleic acid sequences, directed mutagenesis, detection of genetic mutations, diagnoses of viral infections, molecular "fingerprinting," and the monitoring of contaminating microorganisms. See U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which may also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtration", among others.

The polymerase chain reaction comprises repeated rounds, or cycles, of target denaturation, primer annealing, and extension. This reaction process yields an exponential amplification of the desired target sequence and is most advantageously accomplished through the use of a thermally-stable polymerase. The length of time required to complete a particular PCR protocol is dependent upon the number of amplification cycles as well as the length of the denaturation, annealing, and extension steps. A typical PCR performed on a conventional thermal cycler can often take several hours.

The fidelity and efficiency of PCR amplification is affected by several factors. These factors include the concentration of various reaction components, particularly the polymerase, deoxynucleotide triphosphates, magnesium ions, target molecules, and amplimers (amplification primer pair), the length and temperature of the denaturation, annealing, and extension steps, the number of cycles, and the specificity and length of the amplimers. Since the success of any given PCR amplification depends upon a number of variables, optimized reaction conditions are often empirically determined. However, such an optimization process is usually labor intensive, costly, and time consuming.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818; Sooknanan et al., Nucleic Acid Sequence-Based Amplification, Ch. 12 (pp. 261–285) of Molecular Methods for Virus Detection, Academic Press, 1995; and "Profiting from Gene-based Diagnostics", CTB International Publishing Inc., N.J., 1996, both of which are incorporated by reference.

Transcription mediated amplification (TMA) is generally described in U.S. Pat. Nos. 5,399,491, 5,888,779, 5,705,365, 5,710,029, all of which are incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

The ligation chain reaction (LCR) involve the ligation of two smaller probes into a single long probe, using the target sequence as the template for the ligase. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, all of which are incorporated by reference.

Q-beta replicase (QBR) is a mRNA amplification technique, similar to NASBA and TMA, that relies on an RNA-dependent RNA polymerase derived from the bacteriophage Q-beta that can synthesize up to a billion stands of product from a template.

Invader™ technology is based on structure-specific polymerases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

"Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) Nuc. Acids Res. 26:5073–5078; Barany, F. (1991) Proc. Natl. Acad. Sci. USA 88:189–193; Lizardi et al. (1998) Nat. Genet. 19:225–232; Zhang et al., Gene 211:277 (1998); and Daubendiek et al., Nature Biotech. 15:273 (1997); all of which are incorporated by reference in their entirety.

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Similarily, dendrimers of nucleic acids serve to vastly increase the amount of label that can be added to a single molecule, using a similar idea but different compositions. This technology is as described in U.S. Pat. No. 5,175,270 and Nilsen et al., J. Theor. Biol. 187:273 (1997), both of which are incorporated herein by reference.

The ability to perform a variety of preparation and amplification steps in a single miniaturized device has the potential for saving time and expense. Such miniaturized devices can be made much more portable than conventional apparatus, thereby enabling samples to be analyzed outside of the laboratory, such as the location where the samples are collected. A miniaturized DNA analysis device can also allow the analysis steps to be automated more easily. As a result, assays could be performed by less highly trained personnel than presently required.

Thus, there is a significant trend to reduce the size of these sensors, both for sensitivity and to reduce reagent costs. Thus, a number of microfluidic devices have been developed, generally comprising a solid support with microchannels, utilizing a number of different wells, pumps, reaction chambers, and the like. See for example EP 0637996 B1; EP 0637998 B1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071,531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351. In addition, there are a number of devices including PCR microchips fabricated on silicon or glass (Wilding et al., 1994, Clin. Chem. 40:1815–18; Shoffer et al., 1996, Nucleic Acids Res. 24:375–79; Cheng et al., 1996, Nucleic Acids Res. 24:380–85; Woodley et al., 1996, Anal. Chem. 68:4081–86; Northrup et al., 1998, Anal. Chem. 70:918–22; Ibrahim et al., 1998, Anal. Chem. 70:2013–17; U.S. Pat. No. 5,498,392 (Wilding et al., 1996), U.S. Pat. No. 5,587,128 (Wilding et al., 1996), U.S. Pat. No. 5,589,136 (Northrup et al., 1996)).

While conventional PCR is performed in volumes of between 10–100 mL and require several hours to process, microchip PCR is performed in volumes of less than 5 mL and can be completed in minutes. The decrease in reaction time for microchip PCR has been achieved as a result of the low thermal mass of silicon reaction chambers and the integration of thin-film heaters (Northrup et al., 1998, Anal. Chem. 70:918).

While silicon microchip arrays have been fabricated for the parallel analysis of multiple samples (Beigrader et al., 1998, Clin. Chem. 44:2191–94), such devices do not facilitate reaction condition optimization. In order to rapidly optimize amplification conditions for a particular target and amplimer pair, an investigator must be able to perform independently controlled, parallel amplifications on a single microchip array. Due to the inefficient well-to-well thermal isolation achievable in arrays constructed of silicon or glass and the complicated fabrication methods required to prepare microchip arrays from such materials, present techniques have not permitted preparation of a cost-effective commercial microchip array for performing such optimization experiments.

Existing apparatus for performing detection reactions such as thermally-controlled biological reactions on a substrate surface are deficient in that they either require unacceptably large volumes of sample fluid to operate properly, cannot accommodate substrates as large as or larger than a conventional microscope slide, cannot independently accommodate a plurality of independent reactions, or cannot accommodate a substrate containing hydrogel-based microarrays. Most existing apparatus also do not allow introduction of fluids in addition to the sample fluid such as wash buffers, fluorescent dyes, etc., into the reaction chamber. Disposable apparatus require disassembly and reapplication of a new apparatus to the substrate surface every time a new fluid must be introduced. Other existing apparatus are difficult to use in a laboratory environment because they cannot be loaded with standard pipet tips and associated pipettor apparatus.

Many existing apparatus also exhibit unacceptable reaction reproducibility, efficiency, and duration. Reaction reproducibility may be adversely affected by bubble formation in the reaction chamber or by the use of biologically incompatible materials for the reaction chamber. Reaction duration and efficiency may be adversely affected by the presence of concentration gradients in the reaction chamber.

Bubbles can form upon introduction of sample fluid to the reaction chamber or by outgassing of the reaction chamber materials. When gas bubbles extend over the substrate surface in an area containing biologically reactive sites, the intended reaction may intermittently fail or yield erroneous results because the intended concentration of the sample fluid mixture has been compromised by the presence of gas bubbles.

Biologically incompatible reaction chamber materials may cause unacceptable reaction reproducibility, by interacting with the sample fluid, thus causing the intended reaction to intermittently fail or yield erroneous results.

Incomplete mixing of the sample fluid can introduce concentration gradients within the sample fluid that adversely impact reaction efficiency and duration. This effect is most pronounced when there is a depletion of target molecules in the local volume surrounding a biologically reactive site. During a biological reaction, the probability that a particular target molecule will bind to a complementary (immobilized) probe molecule is determined by the given concentration of target molecules present within the sample fluid volume, the diffusion rate of the target molecule through the reaction chamber, and the statistics of interaction between the target molecule and the complementary probe molecule. For diagnostic assays, target DNA molecules are often obtained in minute (<picomol) quantities. In practice, it can take tens of hours for a hybridization reaction to be substantially complete at the low target nucleic acid molecule levels available for biological samples. Concentration gradients in the hybridization chamber can further exacerbate this problem.

U.S. Pat. No. 5,948,673 to Cottingham discloses a self-contained multi-chamber reactor for performing both DNA amplification and DNA probe assays in a sealed unit wherein some reactants are provided by coating the walls of the chambers and other reactants are introduced into the chambers prior to starting the reaction in order to eliminate flow into and out of the chamber. No provisions are made for eliminating gas bubbles from the chambers.

There remains a need in the art for methods and apparatus for performing biological reactions on a substrate surface that use a low volume of sample fluid, that accommodate substrates as large as or larger than a conventional microscope slide, that accommodate a plurality of independent reactions, and that accommodate a substrate surface having one or more hydrogel-based microarrays attached thereto. There also remains a need in the art for an apparatus that allows introduction of fluids in addition to sample fluid into each reaction chamber via standard pipet tips and associated pipettor apparatus. There also remains a need in the art for such an apparatus that increases reaction reproducibility, increases reaction efficiency, and reduces reaction duration. There also remains a need in this art for a simple method for removing gas bubbles from such an apparatus. These needs are particularly striking in view of the tremendous interest in biochip technology, the investment and substantial financial rewards generated by research into biochip technology, and the variety of products generated by such research.

Nucleic acid hybridization assays are advantageously performed using probe array technology, which utilizes binding of target single-stranded DNA onto immobilized DNA (usually, oligonucleotide) probes.

The detection limit of a nucleic acid hybridization assay is determined by the sensitivity of the detection device, and also by the amount of target nucleic acid available to be bound to probes, typically oligonucleotide probes, during hybridization.

A common challenge to all DNA hybridization technologies is the lack of control of stringency for each individual probe site. The DNA hybridization process occurs at specific temperature and salinity conditions and varies with DNA sequences. For DNA probe arrays, since the DNA probe sequences are different, hybridization recognition is never perfect under a uniform stringency condition for the entire probe array. The problem is most obvious for short duplexes which often results in single base mismatches. One can minimize the effect of mismatched hybridization by using large probe site redundancy. Stringency control has been provided for each probe site by controlling the electrophoretic movement of oligonucleotides. To successfully implement this later scheme, a meticulously engineered permeation layer is required to prevent DNA molecules or labeling agents being damaged by direct electrolysis or by the product of the electolysis.

In addition, the current DNA array technologies have failed to provide an effective solution to maximize hybridization efficiency. For diagnostic assays, the target DNA molecules are often of minute quantities. The detection limit of the assay is determined by the sensitivity of the detection device, and also by the amount of target oligos bound to the probes during the course of hybridization. In a stationary hybridization chamber where active mixing is absent, the probability of a given target molecule hybridizes to its complementary strand on the surface is determined by diffusion rate and statistics. It takes up to tens of hours for hybridization to complete at low target concentration levels. To better utilize the target molecules and enhance the hybridization, flow through technology has been proposed where the probe arrays are placed perpendicular to the fluidic flow direction. Even with flow through technology, only a portion of the target molecules can come in contact with any specific DNA probe site.

The present invention overcomes the above technical issues by sequentially placing the DNA probe sites in microfluidic channels such that the DNA probe can efficiently contact its binding partner.

U.S. Pat. No. 5,147,607 describes a variety of microassay devices which have microchannels in plastic materials with a reagent such as an antibody or DNA immobilized on the channel at different locations. Techniques for binding antibodies to the microchannel wall are described but techniques for binding DNA are not described. The binding of probes to the microchannel wall does not provide for optimum contact of probe and test sample. U.S. Pat. No. 5,843,767 describes microfabricated flowthrough porous apparatus for discrete detection of binding reactions such as DNA/DNA. WO/98/43739 describes porous flow channels having reagents immobilized in the chamber.

Nucleic acid hybridization chambers are known in the prior art. U.S. Pat. No. 5,100,755 to Smyczek et al. discloses a hybridization chamber. U.S. Pat. No. 5,545,531 to Rava et al. discloses a hybridization plate comprising a multiplicity of oligonucleotide arrays. U.S. Pat. No. 5,360,741 to Hunnell discloses a gas heated hybridization chamber. U.S. Pat. No. 5,922,591 to Anderson et al. discloses a miniaturized hybridization chamber for use with oligonucleotide arrays. U.S. Pat. No. 5,945,334 to Besemer discloses oligonucleotide array packaging.

As currently employed, oligonucleotide array technology does not provide maximum hybridization efficiency. Existing nucleic acid hybridization assay equipment includes numerous components, each of which is a source of inefficiency and inaccuracy.

Hybridization using oligonucleotide arrays must be performed in a volume in which a small amount of target DNA or other nucleic acid can be efficiently annealed to the immobilized probes. For diagnostic assays, target DNA molecules are often obtained in minute (<picomol) quantities. In practice, it can take several (tens of) hours for hybridization to be substantially complete at the low target nucleic acid levels available for biological samples.

In addition, array hybridization is conventionally performed in a stationary hybridization chamber where active mixing is absent. Under these conditions, the probability that a particular target molecule will hybridize to a complementary oligonucleotide probe immobilized on a surface is determined by the concentration of the target, the diffusion rate of the target molecule and the statistics of interaction between the target and the complementary oligonucleotide. Consequently, a larger number of samples must be tested to obtain useful information, and this in turn leads to increased hybridization times and inefficiencies.

In addition, efficiency is increased when the amount of user manipulation is kept to a minimum. As currently performed, oligonucleotide array hybridization requires a great deal of operator attentiveness and manipulation, and the degree of skill required to perform the analysis is high. For example, hybridization is typically performed in an assay chamber, and then data collection and analysis are performed in a separate apparatus (such as a laser scanner or fluorescence microscope). This arrangement requires a substantial amount of handling by the user, and makes the assays both time-consuming and subject to user error.

It is also a limitation of current practice that array hybridizations are performed one array at a time, thereby forgoing the economies of parallel processing and data analysis.

Additional limitations, inefficiencies, and expenses arise from the structural characteristics of existing apparatus. Many existing apparatus are limited in the size of the substrate they can accommodate. Other apparatus are not disposable and therefore require extensive cleaning between runs in order to prevent sample contamination. Yet other apparatus are high mass and therefore not susceptible of the rapid heating and cooling necessary for efficient hybridization. Other apparatus require the use of expensive optics for analysis of the reaction products.

There remains a need in this art for an easy-to-use apparatus for performing biological reactions, particularly nucleic acid hybridization, that comprises a small reaction volume, where the fluid components can be actively mixed, that can be performed in parallel and that minimizes user intervention. There also remains a need for such an apparatus that is easy to manufacture in various sizes, that is disposable to minimize sample contamination, that allows for the use of low cost optical analytical equipment, and that is low mass to allow for rapid heating and cooling of the sample fluid. There also remains a need for methods for using such apparatus to increase hybridization efficiency, particularly relating to biochip arrays as understood in the art. This need is particularly striking, in view of the tremendous interest in biochip technology, the investment and substantial financial rewards generated by research into biochip technology, and the variety of products generated by such research.

SUMMARY OF THE INVENTION

In accordance with the objects outlined above, the present invention provides microfluidic devices comprising a substrate comprising a plurality of biochannels each comprising a plurality of spatially distinct regions upon which capture binding ligands are immobilized.

In a further aspect, the invention provides microfluidic devices comprising a substrate comprising at least one biochannel comprising a plurality of spatially distinct regions upon which capture binding ligands are immobilized, wherein the biochannel is formed by a spacer such as an adhesive layer affixed to the substrate and a flexible layer.

In an additional aspect, the invention provides microfluidic devices comprising a ceramic substrate comprising at least one biochannel comprising a plurality of spatially distinct regions upon which capture binding ligands are immobilized.

In a further aspect, the invention provides methods of detecting a target analyte in a test sample comprising providing a microfluidic device as outlined herein and flowing a test sample through the microchannel to form an assay complex. The target analyte in the assay complex is then detected.

BRIEF DESCRIPTION OF THE DRAWINGS

FIG. 1 shows a schematic top view of a fluid channel filled with porous gel and spotted DNA probes. FIG. 1 illustrates a serpentine shaped microfluidic channel 1 filled with porous gel 2 with discrete separate regions 3 which have attached a member of a specific binding pair. Such as DNA. Sample flows into the microfluidic channel and exits the channel at 5. In this approach the channel is filled with porous gel matenal such as agarose or polyacrylamide. The pores of the gel are made large enough by using dilute gelling solutions to permit significant fluid flow through the gel members of specific binding pair is spotted onto the gels so that the probes are chemically attached.

FIG. 2 shows lithographically patterned gel pads inside a microfluidic channel. FIG. 2 illustrates a microfluidic channel 10 which has patterned gel pads 11 within the channel. The gel pads are formed by photopolymerization of acrylamide using lithographic techniques.

FIGS. 3a and 3b show microfluidic channels with molded plastic microstructures for DNA attachment. FIGS. 3a and 3b illustrate a microfluidic channel 15 where high surface area microstructures are molded into the channel. FIG. 3a shows a series of columns 16 in a distinct region and FIG. 3b shows a distinct region of domes 17 molded into channel 15. These microstructures are chemically modified and specific binding substances are attached.

FIG. 4 shows a microfluidic channel packed with beads where distinct sections of beads have a specific binding agent such as DNA. FIG. 4 illustrates a microfluidic channel 20 packed alternately with regions of plain beads 21 and beads 22 having a specific binding substance, such as DNA.

FIG. 5 illustrates a simple initial flow being directed into numerous channels. FIG. 5 illustrates a microfluidic channel 25 which branches in multiple microfluidic channels 26a, b, c etc each of which have a distinct region of a binding substance 27 as described above. Through this embodiment, a sample can be studied in parallel to test its reactivity to the same or different specific binding substance.

FIG. 6 illustrates a circulating microfluidic channel device. FIG. 6 illustrates a chip 30 with a recirculating microfluidic channel 34. The microfluidic channel has discrete areas with specific binding substances 32 as described above and a recirculating arm 33 and a valve 34 for output recirculation. In this embodiment the test sample is recirculated past the location of the binding partner. Thus, dilute samples or slow reacting samples can be respectively passed by the specific binding substance.

FIGS. 7A, 7B and 7C depict a variety of different embodiments of the invention. FIG. 7A depicts a substrate with an inlet port into an optional single chamber or well that feeds into a plurality of microchannels with detection pads. FIG. 7B shows individual optional chambers and microchannels. FIG. 7C depicts individual serpentine channels. As described herein, the substrates may comprise additional elements, such as additional wells, thermal units, PCR chambers, etc.

FIG. 8 is a schematic diagram of a microfluidic DNA analysis system, in accordance with a preferred embodiment of the present invention.

FIG. 9 is a schematic diagram of the DNA detection system of FIG. 8, in accordance with a preferred embodiment of the present invention.

FIG. 10 is a cross-sectional sectional view of a microfluidic DNA amplification device, in accordance with a first preferred embodiment of the present invention.

FIG. 10A is a partial top plan view of the microfluidic DNA amplification device of FIG. 10, in accordance with a first preferred embodiment of the present invention.

FIG. 11 is a cross-sectional view of a microfluidic DNA amplification device, in accordance with a second preferred embodiment of the present invention.

FIG. 11A is a partial top plan view of the microfluidic DNA amplification device of FIG. 11, in accordance with a second preferred embodiment of the present invention.

FIG. 12 is a schematic representation of a cross-sectional view of a microchip array according to one embodiment of the invention.

FIG. 13 is a schematic representation of the a cross sectional view of a microchip array according to one embodiment of the invention.

FIGS. 14A–14B are schematic representations of (A) a sixteen well microchip array and (B) a cross-sectional view of the embedded heating elements of a microchip array according to one embodiment of the invention.

FIG. 15 is a schematic representation of a microchip array of the invention having column-and-row electrical addressing.

FIG. 16 is a schematic representation of a microchip array with individual electrical addressing.

FIG. 17 is a schematic representation of a cross-sectional view of a microchip well structure and integrated heating and cooling elements.

FIGS. 18A–18C illustrate the thermal cycling capability of the microchip device of the invention during a 25-cycle experiment (FIG. 18A), over the course of 2 cycles in a 25-cycle experiment (FIG. 18B), and over the course of 2 cycles in a 25-cycle experiment in which the microchip device was clamped to a commercially available thermal cycler (FIG. 18C). In all experiments illustrated, a cycle consisted of a "denaturation" step of 45 sec. at 94° C. and an "annealing" step of 60 sec. at 72° C.

FIG. 19 illustrates the results obtained for the PCR amplification of bla usng the microchip device of the present invention, the left-hand lane contains fragment size standards.

FIG. 20 is an exploded perspective view from the upper side of a specific embodiment of the present invention, illustrating the relationships between the various components and a biochip.

FIG. 21 is an exploded perspective view from the lower side of the apparatus of FIG. 20, illustrating the proper orientation of a biochip.

FIG. 22 is a perspective view from the upper side of the apparatus of FIG. 21, illustrating the apparatus as assembled and ports for viewing the contents of each reaction chamber.

FIG. 23 is a perspective view from the lower side of the apparatus of FIG. 20, illustrating the relationship of the fluid port-sealing member to the base plate.

FIG. 24 is an enlarged partial view of the apparatus of FIG. 20, illustrating details of the base plate and the relationship of the retaining pins to the base plate.

FIG. 25 is an enlarged partial view of the biochip as shown in FIG. 21, illustrating a hydrogel-based microarray attached to a substrate surface.

FIG. 26 is a top view of the apparatus of FIG. 20, illustrating ports for viewing the contents of each reaction chamber.

FIG. 27 is a cross-sectional view of the apparatus of FIG. 20 taken along line 8—8 in FIG. 26, illustrating a reaction chamber.

FIG. 28 is an enlarged partial view of the apparatus of FIG. 20, illustrating the spatial relationship between a reaction chamber and a biochip.

FIG. 29 is an enlarged partial view of the apparatus of FIG. 20, illustrating a reaction chamber seal.

FIG. 30 is a cross-sectional view of the apparatus of FIG. 20 taken along line 8–8 in FIG. 26, illustrating a pipet tip inserted into a fluid port.

FIG. 31 is a front-end plan view of the apparatus of FIG. 20, illustrating the application of a heating element for temperature cycling.

FIG. 32 is a top view of the apparatus of FIG. 20, illustrating an O-ring groove in relation to a well structure and microarray.

FIGS. 33A–33D are views of a preferred embodiment of the present invention illustrating the preparation of a chamber for reaction. FIG. 33A is a cross-sectional view of the apparatus illustrating a reaction chamber prefilled with a water-soluble compound in thermal contact with a heating element. FIG. 33B is a cross sectional view of the apparatus illustrating the mixing of the water-soluble compound and the biological sample fluid. FIG. 33C is a cross sectional view of the apparatus illustrating a chamber filled with the sample fluid/water-soluble compound mixture, wherein the first and second ports are covered with a seal. FIG. 33D is a top plan view of the apparatus illustrating the pattern of adhesive defining the individual areas containing the arrays of oligonucleotide probes.

FIG. 34 is an exploded cross-sectional view of a chamber showing the array of gel pads of a preferred embodiment of the invention.

FIG. 35 is an exploded cross-sectional view of a port illustrating the conical shape of the port of a preferred embodiment of the invention.

FIG. 36 is a cross-sectional view of a stack of chambers according to a preferred embodiment.

FIGS. 37A–37E are top views of the layers of an alternate preferred embodiment of the invention having inlet and outlet ports extending through the flexible layer. FIG. 37A is a view of the first adhesive layer, FIG. 37B is a view of the flexible layer, FIG. 37C is a view of the second adhesive layer, FIG. 37D is a view of the label layer, and FIG. 37E is a view of the layers of 37A to 37D as assembled.

FIGS. 38A–38B are detail views of the notches cut into the first adhesive layer and the label layer of a preferred embodiment of the invention having inlet and outlet ports extending through the flexible layer.

FIGS. 39A–39C are cross-sectional views of a preferred embodiment of the present invention illustrating the process of analyzing the array after completion of the reaction. FIG. 39A shows the apparatus upon completion of the reaction. FIG. 39B illustrates removal of the sample fluid from the chamber such that the flexible layer contacts the array. FIG. 39C illustrates use of a laser scanner to analyze the array. As noted herein, the inlet port 19 may be through the flexible layer 16 as well.

FIGS. 40A–40B illustrate a handheld embodiment of the present invention. FIG. 40A is a side view of the hand held scanning system. FIG. 40B is a perspective view of a preferred embodiment comprising a hand-held scanning device illustrating the contact of the flexible layer with the carriage.

FIGS. 41A–41E are cross-sectional views of the direct contact fiber optic scanner as shown in FIG. 40.

FIGS. 42A–42C are alternate embodiments illustrating the apparatus coupled to a sample preparation chip. FIG. 42A illustrates an embodiment wherein the sample preparation chip is removably positioned against the second surface of the substrate. FIG. 42B illustrates an embodiment wherein the sample preparation chip is affixed to the second surface of the substrate. FIG. 42C illustrates an embodiment wherein the sample preparation chip is incorporated into the substrate.

FIG. 43 illustrates the assembly and use of a preferred embodiment of the present invention.

DETAILED DESCRIPTION OF THE INVENTION

Figure 44:
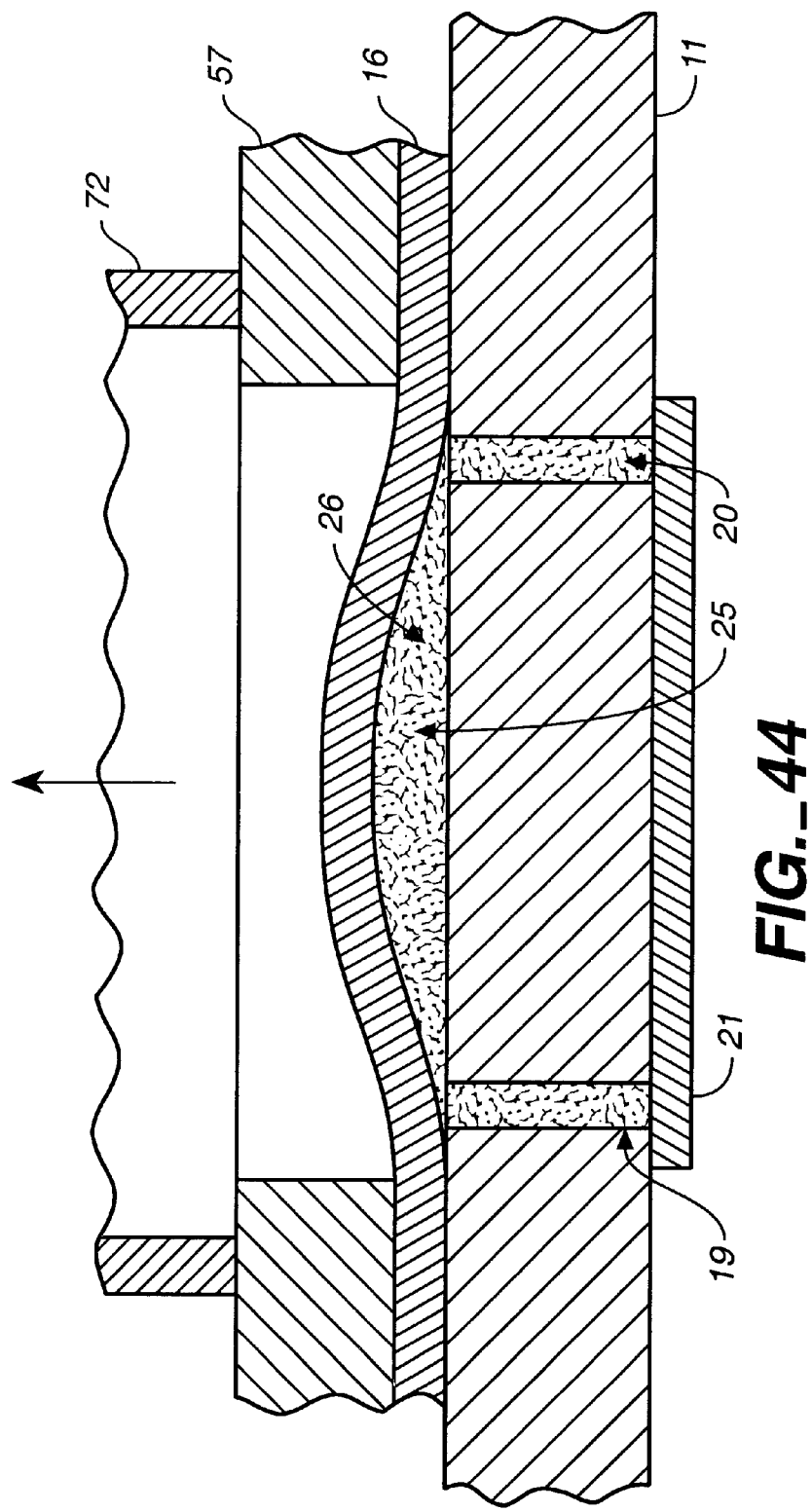
FIG. 44 depicts a cross sectional view of a preferred embodiment of the present invention illustrating the application of vacuum to a reaction chamber or volume.

The present invention is directed to a variety of microfluidic devices with configurations including the use of biochannels or microchannels comprising arrays of capture binding ligands to capture target analytes in samples. The invention provides microfluidic cassettes or devices that can be used to effect a number of manipulations on a sample to ultimately result in target analyte detection or quantification. These manipulations can include cell handling (cell concentration, cell lysis, cell removal, cell separation, etc.), separation of the desired target analyte from other sample components, chemical or enzymatic reactions on the target analyte, detection of the target analyte, etc. The devices of the invention can include one or more wells for sample manipulation, waste or reagents; microchannels to and between these wells, including microchannels containing electrophoretic separation matrices and inlet and outlet ports; valves to control fluid movement; on-chip pumps such as electroosmotic, electrohydrodynamic, or electrokinetic pumps; thermal modules (including devices for both heating and/or cooling); and detection systems, as is more fully described below. The devices of the invention can be configured to manipulate one or multiple samples or analytes.

In a preferred embodiment, the substrates comprising biochannels can be configured to contain reaction chambers including the biochannels, wherein the reaction chamber is formed with a substrate, a layer of adhesive and a flexible cover. The system utilizes ports, either in the substrate or in the flexible cover, to allow sample and/or reagent loading. In addition, the invention provides methods for removing gas bubbles from the apparatus using a gas diffusion accelerator, that will facilitate and accelerate the rate of diffusion through the gas permeable, flexible membrane.

Reference is made to U.S. Ser. Nos. 09/438,600 filed on Nov. 12, 1999; 09/460,281 filed on Dec. 9, 1999; 09/460,283 filed on Dec. 9, 1999; 09/458,534 filed on Dec. 9, 1999; 09/464,490 filed on Dec. 15, 1999; 09/466,325 filed on Dec. 17, 1999; and 09/492,013 filed on Jan. 26, 2000, all of which are expressly incorporated by reference.

Accordingly, the present invention provides devices of the invention are used to detect target analytes in samples. By "target analyte" or "analyte" or grammatical equivalents herein is meant any molecule, compound or particle to be detected. As outlined below, target analytes preferably bind to binding ligands, as is more fully described above. As will be appreciated by those in the art, a large number of analytes may be detected using the present methods; basically, any target analyte for which a binding ligand, described herein, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. Nucleic acid analogs also include "locked nucleic acids". All of these references are hereby expressly incorporated by reference. These modifications of the ribose-phosphate backbone may be done to facilitate the addition of electron transfer moieties, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or electron transfer moiety attachment, an analog structure may be used. Alternatively, mixtures of different nucleic acid analogs, and mixtures of naturally occurring nucleic acids and analogs may be made.

As outlined herein, the nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as nucleosides.

In a preferred embodiment, the present invention provides methods of detecting target nucleic acids. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 100 to 10,000 basepairs, with fragments of roughly 500 basepairs being preferred in some embodiments. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As is outlined more fully below, probes (including primers) are made to hybridize to target sequences to determine the presence or absence of the target sequence in a sample. Generally speaking, this term will be understood by those skilled in the art.

The target sequence may also be comprised of different target domains, which may be adjacent (i.e. contiguous) or separated. For example, when ligation chain reaction (LCR) techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenytoin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including Bacillus; Vibrio, e.g. V. cholerae; Escherichia, e.g. Enterotoxigenic E. coli, Shigella, e.g. S. dysenteriae; Salmonella, e.g. S. typhi; Mycobacterium e.g. M. tuberculosis, M. leprae; Clostridium, e.g. C. botulinum, C. tetani, C. difficile, C. perfringens; Cornyebacterium, e.g. C. diphtheriae; Streptococcus, S. pyogenes, S. pneumoniae; Staphylococcus, e.g. S. aureus; Haemophilus, e.g. H. influenzae; Neisseria, e.g. N. meningitidis, N. gonorrhoeae; Yersinia, e.g. G. lamblia Y. pestis, Pseudomonas, e.g. P. aeruginosa, P. putida; Chlamydia, e.g. C. trachomatis; Bordetella, e.g. B. pertussis; Treponema, e.g. T. palladium; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-$\alpha$ and TGF-$\beta$), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (4) other proteins (including $\alpha$-fetoprotein, carcinoembryonic antigen CEA, cancer markers, etc.).

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Suitable target analytes include metal ions, particularly heavy and/or toxic metals, including but not limited to, aluminum, arsenic, cadmium, selenium, cobalt, copper, chromium, lead, silver and nickel.

These target analytes may be present in any number of different sample types, including, but not limited to, bodily fluids including blood, lymph, saliva, vaginal and anal secretions, urine, feces, perspiration and tears, and solid tissues, including liver, spleen, bone marrow, lung, muscle, brain, etc.

Accordingly, the present invention provides devices for the detection of target analytes comprising a solid substrate. The solid substrate can be made of a wide variety of materials and can be configured in a large number of ways, as is discussed herein and will be apparent to one of skill in the art. In addition, a single device may be comprises of more than one substrate; for example, there may be a "sample treatment" cassette that interfaces with a separate "detection" cassette; a raw sample is added to the sample treatment cassette and is manipulated to prepare the sample for detection, which is removed from the sample treatment cassette and added to the detection cassette. There may be an additional functional cassette into which the device fits; for example, a heating element which is placed in contact with the sample cassette to effect reactions such as PCR. In some cases, a portion of the substrate may be removable; for example, the sample cassette may have a detachable detection cassette, such that the entire sample cassette is not contacted with the detection apparatus. See for example U.S. Pat. No. 5,603,351, PCT US96/17116, and "MULTILAYERED MICROFLUIDIC DEVICES FOR ANALYTE REACTIONS" filed in the PCT Dec. 11, 2000, Ser. No. PCT/US00/33499, hereby incorporated by reference.

The composition of the solid substrate will depend on a variety of factors, including the techniques used to create the device, the use of the device, the composition of the sample, the analyte to be detected, the size of the wells and microchannels, the presence or absence of electronic components, etc. Generally, the devices of the invention should be easily sterilizable as well.

In a preferred embodiment, the solid substrate can be made from a wide variety of materials including, but not limited to, silicon such as silicon wafers, silcon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, brass, sapphire, etc. High quality glasses such as high melting borosilicate or fused silicas may be preferred for their UV transmission properties when any of the sample manipulation steps require light based technologies. In addition, as outlined herein, portions of the internal surfaces of the device may be coated with a variety of coatings as needed, to reduce non-specific binding, to allow the attachment of binding ligands, for biocompatibility, for flow resistance, etc.

Substrates comprising channels can be made in a variety of ways. Microfabricated plastic capillary electrophoresis (CE) devices have been demonstrated in the art. Thermoplastic molded polymethylmethacrylate CE devices are described by R. M. McCormick, et al, "Microchannel electrophoretic separations of DNA in injection-molded plastic substrates," Anal. Chem., vol. 69, pp. 2626, 1997. Eckstrom et al investigated elastomeric polymers such as PDMS, "PCT Appl. WO91/16966," 1991. More recently, others have published electrophoretic separation of DNA ladders in PDMS devices, for example, C. S. Effenhauser, et al, "Integrated Capillary Electrophoresis on Flexible Silicone Microdevices," Anal. Chem. vol. 69. pp. 3451, 1997. Mastrangelo, et al describes building micro CE devices based on parylene-polycarbonate substrates using a surface micromachining approach, "An Inexpensive Plastic Technology for Microfabricated Capillary Electroophoresis Chip" presented at Micro-TAS'98, Banff, 1998. Thus, techniques are available for fabricating microchannels. The invention involves fixing specific binding substances by way of porous polymer, beads or structure in the microchannel to more efficiently promote binding.

In a preferred embodiment, the solid support comprises ceramic materials, such as are outlined in U.S. Ser. Nos. 09/235,081; 09/337,086; 09/464,490; 09/492,013; 09/466,325; 09/460,281; 09/460,283; 09/387,691; 09/438,600; 09/506,178; and 09/458,534; all of which are expressly incorporated by reference in their entirety. In this embodiment, the devices are made from layers of green-sheet that have been laminated and sintered together to form a substantially monolithic structure. Green-sheet is a composite material that includes inorganic particles of glass, glass-ceramic, ceramic, or mixtures thereof, dispersed in a polymer binder, and may also include additives such as plasticizers and dispersants. The green-sheet is preferably in the form of sheets that are 50 to 250 microns thick. The ceramic particles are typically metal oxides, such as aluminum oxide or zirconium oxide. An example of such a green-sheet that includes glass-ceramic particles is "AX951" that is sold by E.I. Du Pont de Nemours and Company. An example of a green-sheet that includes aluminum oxide particles is "Ferro Alumina" that is sold by Ferro Corp. The composition of the green-sheet may also be custom formulated to meet particular applications. The green-sheet layers are laminated together and then fired to form a substantially monolithic multilayered structure. The manufacturing, processing, and applications of ceramic green-sheets are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference.

The method for fabricating devices (such as those depicted in FIGS. 10 and 11 as devices 100 and 300) begins with providing sheets of green-sheet that are preferably 50 to 250 microns thick. The sheets of green-sheet are cut to the desired size, typically 6 inches by 6 inches for conventional processing, although smaller or larger devices may be used as needed. Each green-sheet layer may then be textured using various techniques to form desired structures, such as vias, channels, or cavities, in the finished multilayered structure.

Various techniques may be used to texture a green-sheet layer. For example, portions of a green-sheet layer may be punched out to form vias or channels. This operation may be accomplished using conventional multilayer ceramic punches, such as the Pacific Trinetics Corp. Model APS-8718 Automated Punch System. Instead of punching out part of the material, features, such as channels and wells may be embossed into the surface of the green-sheet by pressing the green-sheet against an embossing plate that has a negative image of the desired structure. Texturing may also be accomplished by laser tooling with a laser via system, such as the Pacific Trinetics LVS-3012.

Next, a wide variety of materials may be applied, preferably in the form of thick-film pastes, to each textured green-sheet layer. For example, electrically conductive pathways may be provided by depositing metal-containing thick-film pastes onto the green-sheet layers. Thick-film pastes typically include the desired material, which may be either a metal or a dielectric, in the form of a powder dispersed in an organic vehicle, and the pastes are designed to have the viscosity appropriate for the desired deposition technique, such as screen-printing. The organic vehicle may include resins, solvents, surfactants, and flow-control agents. The thick-film paste may also include a small amount of a flux, such as a glass frit, to facilitate sintering. Thick-film technology is further described in J. D. Provance, "Performance Review of Thick Film Materials," *Insulation/Circuits* (April, 1977) and in Morton L. Topfer, *Thick Film Microelectronics, Fabrication, Design, and Applications* (1977), pp. 41–59, which are incorporated herein by reference.

The porosity of the resulting thick-film can be adjusted by adjusting the amount of organic vehicle present in the thick-film paste. Specifically, the porosity of the thick-film can be increased by increased the percentage of organic vehicle in the thick-film paste. Similarly, the porosity of a green-sheet layer can be increased by increasing the proportion of organic binder. Another way of increasing porosity in thick-films and green-sheet layers is to disperse within the organic vehicle, or the organic binder, another organic phase that is not soluble in the organic vehicle. Polymer microspheres can be used advantageously for this purpose.

To add electrically conductive pathways, the thick film pastes typically include metal particles, such as silver, platinum, palladium, gold, copper, tungsten, nickel, tin, or alloys thereof. Silver pastes are preferred. Examples of suitable silver pastes are silver conductor composition numbers 7025 and 7713 sold by E.I. Du Pont de Nemours and Company.

The thick-film pastes are preferably applied to a green-sheet layer by screen-printing. In the screen-printing process, the thick-film paste is forced through a patterned silk screen so as to be deposited onto the green-sheet layer in a corresponding pattern. Typically, the silk screen pattern is created photographically by exposure to a mask. In this way, conductive traces may be applied to a surface of a green-sheet layer. Vias present in the green-sheet layer may also be filled with thick-film pastes. If filled with thick-filled pastes containing electrically conductive materials, the vias can serve to provide electrical connections between layers.

After the desired structures are formed in each layer of green-sheet, preferably a layer of adhesive is applied to either surface of the green-sheet. Preferably, the adhesive is a room-temperature adhesive. Such room-temperature adhesives have glass transition temperatures below room temperature, i.e., below about 20° C., so that they can bind substrates together at room temperature. Moreover, rather than undergoing a chemical change or chemically reacting with or dissolving components of the substrates, such room-temperature adhesives bind substrates together by penetrating into the surfaces of the substrates. Sometimes such room-temperature adhesives are referred to as "pressure-sensitive adhesives." Suitable room-temperature adhesives are typically supplied as water-based emulsions and are available from Rohm and Haas, Inc. and from Air Products, Inc. For example, a material sold by Air Products, Inc. as "Flexcryl 1653" has been found to work well.

The room-temperature adhesive may be applied to the green-sheet by conventional coating techniques. To facilitate coating, it is often desirable to dilute the supplied pressure-sensitive adhesive in water, depending on the coating technique used and on the viscosity and solids loading of the starting material. After coating, the room-temperature adhesive is allowed to dry. The dried thickness of the film of room-temperature adhesive is preferably in the range of 1 to 10 microns, and the thickness should be uniform over the entire surface of the green-sheet. Film thicknesses that exceed 15 microns are undesirable. With such thick films of adhesive voiding or delamination can occur during firing, due to the large quantity of organic material that must be removed. Films that are less than about 0.5 microns thick when dried are too thin because they provide insufficient adhesion between the layers.

From among conventional coating techniques, spin-coating and spraying are the preferred methods. If spin-coating is used, it is preferable to add 1 gram of deionized water for every 10 grams of "Flexcryl 1653." If spraying is used, a higher dilution level is preferred to facilitate ease of spraying. Additionally, when room-temperature adhesive is sprayed on, it is preferable to hold the green-sheet at an elevated temperature, e.g., about 60 to 70° C., so that the material dries nearly instantaneously as it is deposited onto the green-sheet. The instantaneous drying results in a more uniform and homogeneous film of adhesive.

After the room-temperature adhesive has been applied to the green-sheet layers, the layers are stacked together to form a multilayered green-sheet structure. Preferably, the layers are stacked in an alignment die, so as to maintain the desired registration between the structures of each layer. When an alignment die is used, alignment holes must be added to each green-sheet layer. Typically, the stacking process alone is sufficient to bind the green-sheet layers together when a room-temperature adhesive is used. In other words, little or no pressure is required to bind the layers together. However, in order to effect a more secure binding of the layers, the layers are preferably laminated together after they are stacked.

The lamination process involves the application of pressure to the stacked layers. For example, in the conventional lamination process, a uniaxial pressure of about 1000 to 1500 psi is applied to the stacked green-sheet layers that is then followed by an application of an isostatic pressure of about 3000 to 5000 psi for about 10 to 15 minutes at an elevated temperature, such as 70° C. Adhesives do not need to be applied to bind the green-sheet layers together when the conventional lamination process is used.

However, pressures less than 2500 psi are preferable in order to achieve good control over the dimensions of such structures as internal or external cavities and channels. Even lower pressures are more desirable to allow the formation of larger structures, such as cavities and channels. For example, if a lamination pressure of 2500 psi is used, the size of well-formed internal cavities and channels is typically limited to no larger than roughly 20 microns. Accordingly, pressures less than 1000 psi are more preferred, as such pressures generally enable structures having sizes greater than about 100 microns to be formed with some measure of dimensional control. Pressures of less than 300 psi are even more preferred, as such pressures typically allow structures with sizes greater than 250 microns to be formed with some degree of dimensional control. Pressures less than 100 psi, which are referred to herein as "near-zero pressures," are most preferred, because at such pressures few limits exist on the size of internal and external cavities and channels that can be formed in the multilayered structure.

The pressure is preferably applied in the lamination process by means of a uniaxial press.

Alternatively, pressures less than about 100 psi may be applied by hand.

As with semiconductor device fabrication, many devices may be present on each sheet.

Accordingly, after lamination the multilayered structure may be diced using conventional green-sheet dicing or sawing apparatus to separate the individual devices. The high level of peel and shear resistance provided by the room-temperature adhesive results in the occurrence of very little edge delamination during the dicing process. If some layers become separated around the edges after dicing, the layers may be easily re-laminated by applying pressure to the affected edges by hand, without adversely affecting the rest of the device.

The final processing step is firing to convert the laminated multilayered green-sheet structure from its "green" state to form the finished, substantially monolithic, multilayered structure. The firing process occurs in two important stages as the temperature is raised. The first important stage is the binder burnout stage that occurs in the temperature range of about 250 to 500° C., during which the other organic materials, such as the binder in the green-sheet layers and the organic components in any applied thick-film pastes, are removed from the structure.

In the next important stage, the sintering stage, which occurs at a higher temperature, the inorganic particles sinter together so that the multilayered structure is densified and becomes substantially monolithic. The sintering temperature used depends on the nature of the inorganic particles present in the green-sheet. For many types of ceramics, appropriate sintering temperatures range from about 950 to about 1600° C., depending on the material. For example, for green-sheet containing aluminum oxide, sintering temperatures between 1400 and 1600° C. are typical. Other ceramic materials, such as silicon nitride, aluminum nitride, and silicon carbide, require higher sintering temperatures, namely 1700 to 2200° C. For green-sheet with glass-ceramic particles, a sintering temperature in the range of 750 to 950° C. is typical. Glass particles generally require sintering temperatures in the range of only about 350 to 700° C. Finally, metal particles may require sintering temperatures anywhere from 550 to 1700° C., depending on the metal.

Typically, the devices are fired for a period of about 4 hours to about 12 hours or more, depending on the material used. Generally, the firing should be of a sufficient duration so as to remove the organic materials from the structure and to completely sinter the inorganic particles. In particular, polymers are present as a binder in the green-sheet and in the room-temperature adhesive. The firing should be of sufficient temperature and duration to decompose these polymers and to allow for their removal from the multilayered structure.

Typically, the multilayered structure undergoes a reduction in volume during the firing process. During the binder burnout phase, a small volume reduction of about 0.5 to 1.5% is normally observed. At higher temperatures, during the sintering stage, a further volume reduction of about 14 to 17% is typically observed.

The volume change due to firing, on the other hand, can be controlled. In particular, to match volume changes in two materials, such as green-sheet and thick-film paste, one should match: (1) the particle sizes; and (2) the percentage of organic components, such as binders, which are removed during the firing process. Additionally, volume changes need not be matched exactly, but any mismatch will typically result in internal stresses in the device. But symmetrical processing, placing the identical material or structure on opposite sides of the device can, to some extent, compensate for shrinkage mismatched materials. Too great a mismatch in either sintering temperatures or volume changes may result in defects in or failure of some or all of the device. For example, the device may separate into its individual layers, or it may become warped or distorted.

As noted above, preferably any dissimilar materials added to the green-sheet layers are co-fired with them. Such dissimilar materials could be added as thick-film pastes or as other green-sheet layers, or added later in the fabrication process, after sintering. The benefit of co-firing is that the added materials are sintered to the green-sheet layers and become integral to the substantially monolithic microfluidic device. However, to be co-fireable, the added materials should have sintering temperatures and volume changes due to firing that are matched with those of the green-sheet layers. Sintering temperatures are largely material-dependent, so that matching sintering temperatures simply requires proper selection of materials. For example, although silver is the preferred metal for providing electrically conductive pathways, if the green-sheet layers contain alumina particles, which require a sintering temperature in the range of 1400 to 1600° C., some other metal, such as platinum, must be used due to the relatively low melting point of silver (961° C.).

Alternatively, the addition of other substrates or joining of two post-sintered pieces can be done using any variety of adhesive techniques, including those outlined herein. For example, two "halves" of a device can be glued or fused together. For example, a particular detection platform, reagent mixture such as a hydrogel or biological components that are not stable at high temperature can be sandwiched in between the two halves. Alternatively, ceramic devices comprising open channels or wells can be made, additional substrates or materials placed into the devices, and then they may be sealed with other materials.

A particularly preferred substrate is glass, such as a microscope slide.

In addition to the ceramics components of the devices, there may be additional components of other materials as outlined herein. These components can be made in a variety of ways, as will be appreciated by those in the art. See for example WO96/39260, directed to the formation of fluid-tight electrical conduits; U.S. Pat. No. 5,747,169, directed to sealing; EP 0637996 B1; EP 0637998 B1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071,531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are hereby incorporated by reference. Suitable fabrication techniques again will depend on the choice of substrate or component, but preferred methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques (see U.S. Pat. No. 5,747,169, hereby incorporated by reference). In addition, there are printing techniques for the creation of desired fluid guiding pathways; that is, patterns of printed material can permit directional fluid transport. Thus, the build-up of "ink" can serve to define a flow channel. In addition, the use of different "inks" or "pastes" can allow different portions of the pathways having different flow properties. For example, materials can be used to change solute/solvent RF values (the ratio of the distance moved by a particular solute to that moved by a solvent front). For example, printed fluid guiding pathways can be manufactured with a printed layer or layers comprised of two different materials, providing different rates of fluid transport. Multi-material fluid guiding pathways can be used when it is desirable to modify retention times of reagents in fluid guiding pathways. Furthermore, printed fluid guiding pathways can also provide regions containing reagent substances, by including the reagents in the "inks" or by a subsequent printing step. See for example U.S. Pat. No. 5,795,453, herein incorporated by reference in its entirety.

In a preferred embodiment, the solid substrate is configured for handling a single sample that may contain a plurality of target analytes. That is, a single sample is added to the device and the sample may either be aliquoted for parallel processing for detection of the analytes or the sample may be processed serially, with individual targets being detected in a serial fashion. In addition, samples may be removed periodically or from different locations for in line sampling.

In a preferred embodiment, the solid substrate is configured for handling multiple samples, each of which may contain one or more target analytes. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection platform.

Furthermore, in some embodiments, the substrate comprises a multiplicity of arrays, particularly nucleic acid arrays, which are contained in one or a plurality of reaction volumes (e.g. bounded by the adhesive and covered by the flexible layer). The reaction volume can comprise a biochannel comprising a plurality of spatially separated "pads" or "array addresses" comprising different capture probes, formed by the use of a spacer such as an adhesive and covered by a flexible layer. As for all the embodiments outlined herein, samples may be introduced into the reaction volume through ports either in the substrate or in the flexible layer. See generally FIG. 7.

In addition, it should be understood that while most of the discussion herein is directed to the use of generally planar substrates with microchannels and wells, other geometries can be used as well. For example, two or more planar substrates can be stacked to produce a three dimensional device, that can contain microchannels flowing within one plane or between planes; similarly, wells may span two or more substrates to allow for larger sample volumes. Thus for example, both sides of a substrate can be etched to contain microchannels; see for example U.S. Pat. Nos. 5,603,351 and 5,681,484, both of which are hereby incorporated by reference.

The biochip substrates of the invention have capture binding ligands attached in array formats. By "array" or "biochip" herein is meant a plurality of capture binding ligands, preferably nucleic acids, in an array format; the size of the array will depend on the composition and end use of the array. Most of the discussion herein is directed to the use of nucleic acid arrays with attached capture probes, but this is not meant to limit the scope of the invention, as other types of capture binding ligands (proteins, etc.), can be used. "Array" in this context generally refers to an ordered spatial arrangement, particularly an arrangement of immobilized biomolecules or polymeric anchoring structures. "Addressble array" refers to an array wherein the individual elements have precisely defined X and Y coordinates, so that a given element at a particular position in the array can be identified.

Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. The size of the array can vary; with arrays containing from about 2 different capture probes to many millions can be made, with very large arrays being possible. Generally, the array will comprise from two to as many as 100,000, with from about 400 to about 1000 being the most preferred, and about 10,000 being especially preferred. Arrays can also be classifed as "addressable", which means that the individual elements of the array have precisely defined x and y coordinates, so that a given array element can be pinpointed.

In a preferred embodiment, the devices of the invention comprise biochannels or microchannels comprising arrays of capture binding ligands; that is, the channels comprise spatially separated regions of immobilized capture binding ligands, particularly oligonucleotides. The microchannels may have a variety of configurations, feedback arms, valves, and vents to control fluid flow. There may be single or multiple channels that converge in one or more wells. For example, a single PCR reaction chamber can "feed" into a plurality of biochannels. Alternatively, each biochannel can comprise its own PCR chamber (or any other microfluidic structure as described herein). The invention provides for efficient contact between immobilized binding substances (e.g. capture binding ligands) and binding partners (e.g. target analytes) in the fluid flowing through the channel. The invention provides for improved hybridization stringency control by flow modulation; shortened assay time by increasing the rate of hybridization with flow induced agitation and by bringing the target and probe into proximity within the microfluidic channel; and increased hybridization efficiency which improves sensitivity. In addition there is no interference through hydrolysis.

The microfluidic channels of the present invention are channels generally less than 200 microns in plastic with molding or embossing technology. The channels need to be of the dimension to support pumping of the microfluidic system The microfluidic channel may have any shape, for example, it may be linear, serpentine, arc shaped and the like. The cross-sectional dimension of the channel may be square, rectagular, semicircular, circular, etc. There may be multiple and interconnected microchannels with valves to provide for recirculation.

In a preferred embodiment, pumps (as generally described below) or other fluid propelling components such as pressurized gas, vacuum, electric field, magnetic field and centrifugal force devices are operatively associated with the microchannel to move fluid through the microchannel. In addition, charged test samples may be altered by modulating the electric field against or in the direction of the flow or perpendicular to the flow. Thus, the rate of fluid flow in the microchannel can be altered to promote binding of binding pairs, for example, hybridization of DNAIDNA or DNA/ RNA pairs. Also, as more fully outlined below, operatively associated with the microchannel is a detector such as an optical, electrical or electrochemical detector.

The invention is advantageously used for performing assays using biochips 18. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence expected to be present in a biological sample. Alternatively, peptides or other small molecules can be arrayed in such biochips for performing immunological analysis (wherein the arrayed molecules are antigens) or assaying biological receptors (wherein the arrayed molecules are ligands, agonists or antagonists of said receptors). Thus, while "probes" generally refer to nucleic acids that are substantially complementary to target nucleic acids, "probe" and "biomolecular probe" can also refer to a biomolecule used to detect another biomolecule, e.g. its binding partner.

One useful feature of biochips is the manner in which the arrayed biomolecules are attached to the surface of the biochip. Conventionally such procedures involve multiple reaction steps, often requiring chemical modification of the solid support itself. Even in embodiments comprising absorption matrices, such as hydrogels, present on a solid support, chemical modification of the gel polymer is necessary to provide a chemical functionality capable forming a covalent bond with the biomolecule. The efficiency of the attachment chemistry and strength of the chemical bonds formed are critical to the fabrication and ultimate performance of the microarray.

Polymeric hydrogels and gel pads are used as binding layers to adhere to surfaces biological molecules including, but not limited to, proteins, peptides, oligonucleotides, polynucleotides, and larger nucleic acid fragments. The oligonucleotide probes may be bound to the surface of a continuous layer of the hydrogel, or to an array of gel pads. The gel pads comprising biochips for use with the apparatus of the present invention are conveniently produced as thin sheets or slabs, typically by depositing a solution of acrylamide monomer, a crosslinker such methylene bisacrylamide, and a catalyst such as N,N,N',N'-tetramethylethylendiamine (TEMED) and an initiator such as ammonium persulfate for chemical polymerization, or 2,2-dimethoxy-2-phenyl-acetophone (DMPAP) for photopolymerization, in between two glass surfaces (e.g., glass plates or microscope slides) using a spacer to obtain the desired thickness of the polymeric gel. Generally, the acrylamide monomer and crosslinker are prepared in one solution of about 4–5% acrylamide (having an acrylamide/ bisacrylamide ratio of 19/1) in water/glycerol, with a nominal amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature (e.g., typically at about 40° C.). Following polymerization and crosslinking, the top glass slide is removed from the surface to uncover the gel. The pore size (and hence the "sieving properties") of the gel is controlled by changing the amount of crosslinker and the percent solids in the monomer solution. The pore size also can be controlled by changing the polymerization temperature.

In the fabrication of polyacrylamide embodiments of the polymeric hydrogel arrays of the invention (i.e., patterned gels) used as binding layers for biological molecules, the acrylamide solution typically is imaged through a mask during the UV polymerization/crosslinking step. The top glass slide is removed after polymerization, and the unpolymerized monomer is washed away (developed) with water, leaving a fine feature pattern of polyacrylamide hydrogel, which is used to produce the crosslinked polyacrylamide hydrogel pads. Further, in an application of lithographic techniques known in the semiconductor industry, light can be applied to discrete locations on the surface of a polyacrylamide hydrogel to activate these specified regions for the attachment of an oligonucleotide, an antibody, an antigen, a hormone, hormone receptor, a ligand or a polysaccharide on the surface (e.g., a polyacrylamide hydrogel surface) of a solid support (see, for example, International Application, Publication No. WO 91/07087, incorporated by reference).

For hydrogel-based arrays using polyacrylamide, biomolecules (such as oligonucleotides) are covalently attached by forming an amide, ester or disulfide bond between the biomolecule and a derivatized polymer comprising the cognate chemical group. Covalent attachment of the biomolecule to the polymer is usually performed after polymerization and chemical cross-linking of the polymer is completed.

Alternatively, oligonucleotides bearing 5'-terminal acrylamide modifications can be used that efficiently copolymerize with acrylamide monomers to form DNA-containing polyacrylamide copolymers (Rehman et al., 1999, *Nucleic Acids Research* 27: 649–655). Using this approach, stable probe-containing layers can be fabricated on supports (e.g., microtiter plates and silanized glass) having exposed acrylic groups. This approach has made available the commercially marketed "Acrydite™" capture probes (available from Mosaic Technologies, Boston, Mass.). The Acrydite moiety is a phosporamidite that contains an ethylene group capable of free-radical copolymerization with acrylamide, and which can be used in standard DNA synthesizers to introduce copolymerizable groups at the 5' terminus of any oligonucleotide probe.

Thus, the devices of the invention include at least one microchannel or flow channel (sometimes referred to herein as "vias") that allows the flow of sample from the sample inlet port to the other components or modules of the system. The collection of microchannels and wells is sometimes referred to in the art as a "mesoscale flow system". As will be appreciated by those in the art, the flow channels may be configured in a wide variety of ways, depending on the use of the channel. For example, a single flow channel starting at the sample inlet port may be separated into a variety of smaller channels, such that the original sample is divided into discrete subsamples for parallel processing or analysis. Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used.

In general, the microfluidic devices of the invention are generally referred to as "mesoscale" devices. The devices herein are typically designed on a scale suitable to analyze microvolumes, although in some embodiments large samples (e.g. cc's of sample) may be reduced in the device to a small volume for subsequent analysis. That is, "mesoscale" as used herein refers to chambers and microchannels that have cross-sectional dimensions on the order of 0.1 $\mu$m to 500 $\mu$m. The mesoscale flow channels and wells have preferred depths on the order of 0.1 $\mu$m to 100 $\mu$m, typically 2–50 $\mu$m. The channels have preferred widths on the order of 2.0 to 500 $\mu$m, more preferably 3–100 $\mu$m. For many applications, channels of 5–50 $\mu$m are useful. However, for many applications, larger dimensions on the scale of millimeters may be used; for example, in ceramic applications, typical vias have diameters ranging from 100 to 500 microns. Vias may also be filled with other materials, such as metallic pastes containing metal particles, such as silver, platinum, gold, copper, tungsten, nickel, tin, or alloys thereof. Preferably the metallic paste is silver.

Similarly, chambers (sometimes also referred to herein as "wells") in the substrates often will have larger dimensions, on the scale of a few millimeters. The well structures of the microarray of the present invention can have volumes ranging from 1 to 25 mL, and may be configured as, for example, cylinders, rectangles, or squares, or any other convenient or useful cross-sectional shape. Similarly, they may be irregularly shaped; they may be wider at the top, etc. In one embodiment of the present invention, the well structures have a volume of about 2 mL and are configured as cylinders. Suitable well structures may have a number of different dimensions that would permit reactions of between 1 and 25 mL to be performed therein. In preferred embodiments of the microarray of the present invention, the well structures have depths of between 1 and 10 mm and diameters of between 0.5 and 5 mm. In one embodiment, the well structures have a depth of 2 mm and a diameter of 1.2 mm. In an alternative embodiment, well structures have a depth of 2.5 mm and a diameter of 1 mm (FIG. 17). In embodiments relying on thermal modules, the flow of heat will determine the most favorable dimensions for the well structures, and the dimensions will vary with the materials used for the fabrication of the integral heating and cooling components.

In addition to the flow channel system, the devices of the invention are configured to include one or more of a variety of components, herein referred to as "modules", that will be present on any given device depending on its use. These modules include, but are not limited to: sample inlet ports; sample introduction or collection modules; cell handling modules (for example, for cell lysis, cell removal, cell concentration, cell separation or capture, cell growth, etc.); separation modules, for example, for electrophoresis, dielectrophoresis, gel filtration, ion exchange/affinity chromatography (capture and release) etc.; reaction modules for chemical or biological alteration of the sample, including amplification of the target analyte (for example, when the target analyte is nucleic acid, amplification techniques are useful, including, but not limited to polymerase chain reaction (PCR), ligase chain reaction (LCR), strand displacement amplification (SDA), and nucleic acid sequence based amplification (NASBA)), chemical, physical or enzymatic cleavage or alteration of the target analyte, or chemical modification of the target; fluid pumps; fluid valves; thermal modules for heating and cooling (which may be part of other modules, such as reaction modules); storage modules for assay reagents; mixing chambers; and detection modules. In particular, the present invention provides for thermal modules which allow for heating and/or cooling of the samples.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well or chamber.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the devices of the invention include a cell handling module. This is of particular use when the sample comprises cells that either contain the target analyte or that must be removed in order to detect the target analyte. Thus, for example, the detection of particular antibodies in blood can require the removal of the blood cells for efficient analysis, or the cells (and/or nucleus) must be lysed prior to detection. In this context, "cells" include eukaryotic and prokaryotic cells, and viral particles that may require treatment prior to analysis, such as the release of nucleic acid from a viral particle prior to detection of target sequences. In addition, cell handling modules may also utilize a downstream means for determining the presence or absence of cells. Suitable cell handling modules include, but are not limited to, cell lysis modules, cell removal modules, cell concentration modules, and cell separation or capture modules. In addition, as for all the modules of the invention, the cell handling module is in fluid communication via a flow channel with at least one other module of the invention.

In a preferred embodiment, the cell handling module includes a cell lysis module. As is known in the art, cells may be lysed in a variety of ways, depending on the cell type. In one embodiment, as described in EP 0 637 998 B1 and U.S. Pat. No. 5,635,358, hereby incorporated by reference, the cell lysis module may comprise cell membrane piercing protrusions that extend from a surface of the cell handling module. As fluid is forced through the device, the cells are ruptured. Similarly, this may be accomplished using sharp edged particles trapped within the cell handling region. Alternatively, the cell lysis module can comprise a region of restricted cross-sectional dimension, which results in cell lysis upon pressure.

In a preferred embodiment, the cell lysis module comprises a cell lysing agent, such as guanidium chloride, chaotropic salts, enzymes such as lysozymes, etc. In some embodiments, for example for blood cells, a simple dilution with water or buffer can result in hypotonic lysis. The lysis agent may be solution form, stored within the cell lysis module or in a storage module and pumped into the lysis module. Alternatively, the lysis agent may be in solid form, that is taken up in solution upon introduction of the sample.

The cell lysis module may also include, either internally or externally, a filtering module for the removal of cellular debris as needed. This filter may be microfabricated between the cell lysis module and the subsequent module to enable the removal of the lysed cell membrane and other cellular debris components; examples of suitable filters are shown in EP 0 637 998 B1, incorporated by reference.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population, for example, white blood cells for the analysis of chromosomal nucleic acid, or subsets of white blood cells. These binding moieties may be immobilized either on the surface of the module or on a particle trapped within the module (i.e. a bead) by physical absorption or by covalent attachment. Suitable binding moieties will depend on the cell type to be isolated or removed, and generally includes antibodies and other binding ligands, such as ligands for cell surface receptors, etc. Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size. This can be done in a variety of ways, including protrusions from the surface that allow size exclusion, a series of narrowing channels, a weir, or a diafiltration type setup.

In a preferred embodiment, the cell handling module includes a cell removal module. This may be used when the sample contains cells that are not required in the assay or are undesirable. Generally, cell removal will be done on the basis of size exclusion as for "sieving", above, with channels exiting the cell handling module that are too small for the cells.

In a preferred embodiment, the cell handling module includes a cell concentration module. As will be appreciated by those in the art, this is done using "sieving" methods, for example to concentrate the cells from a large volume of sample fluid prior to lysis.

In a preferred embodiment, the devices of the invention include a separation module. Separation in this context means that at least one component of the sample is separated from other components of the sample. This can comprise the separation or isolation of the target analyte, or the removal of contaminants that interfere with the analysis of the target analyte, depending on the assay.

In a preferred embodiment, the separation module includes chromatographic-type separation media such as absorptive phase materials, including, but not limited to reverse phase materials (e.g. $C_8$ or $C_{18}$ coated particles, etc.), ion-exchange materials, affinity chromatography materials such as binding ligands, etc. See U.S. Pat. No. 5,770,029, herein incorporated by reference.

In a preferred embodiment, the separation module utilizes binding ligands, as is generally outlined herein for cell separation or analyte detection. In this embodiment, binding ligands are immobilized (again, either by physical absorption or covalent attachment, described below) within the separation module (again, either on the internal surface of the module, on a particle such as a bead, filament or capillary trapped within the module, for example through the use of a frit). Suitable binding moieties will depend on the sample component to be isolated or removed. By "binding ligand" or grammatical equivalents herein is meant a compound that is used to bind a component of the sample, either a contaminant (for removal) or the target analyte (for enrichment). In some embodiments, as outlined below, the binding ligand is used to probe for the presence of the target analyte, and that will bind to the analyte.

As will be appreciated by those in the art, the composition of the binding ligand will depend on the sample component to be separated. Binding ligands for a wide variety of analytes are known or can be readily found using known techniques. For example, when the component is a protein, the binding ligands include proteins (particularly including antibodies or fragments thereof (FAbs, etc.)) or small molecules. When the sample component is a metal ion, the binding ligand generally comprises traditional metal ion ligands or chelators. Preferred binding ligand proteins include peptides. For example, when the component is an enzyme, suitable binding ligands include substrates and inhibitors. Antigen-antibody pairs, receptor-ligands, and carbohydrates and their binding partners are also suitable component-binding ligand pairs. The binding ligand may be nucleic acid, when nucleic acid binding proteins are the targets; alternatively, as is generally described in U.S. Pat. Nos. 5,270,163, 5,475,096, 5,567,588, 5,595,877, 5,637,459, 5,683,867,5,705,337, and related patents, hereby incorporated by reference, nucleic acid "aptomers" can be developed for binding to virtually any target analyte. Similarly, there is a wide body of literature relating to the development of binding partners based on combinatorial chemistry methods. In this embodiment, when the binding ligand is a nucleic acid, preferred compositions and techniques are outlined in PCT US97/20014, hereby incorporated by reference.

In a preferred embodiment, the binding of the sample component to the binding ligand is specific, and the binding ligand is part of a binding pair. By "specifically bind" herein is meant that the ligand binds the component, for example the target analyte, with specificity sufficient to differentiate between the analyte and other components or contaminants of the test sample. The binding should be sufficient to remain bound under the conditions of the separation step or assay, including wash steps to remove non-specific binding. In some embodiments, for example in the detection of certain biomolecules, the disassociation constants of the analyte to the binding ligand will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors.

When the sample component bound by the binding ligand is the target analyte, it may be released for detection purposes if necessary, using any number of known techniques, depending on the strength of the binding interaction, including changes in pH, salt concentration, temperature, etc. or the addition of competing ligands, detergents, chaotropic agents, organic compounds, or solvents, etc.

In some embodiments, preferential binding of molecules to surfaces can be achieved using coating agents or buffer conditions; for example, DNA and RNA may be differentially bound to glass surfaces depending on the conditions.

In a preferred embodiment, the separation module includes an electrophoresis module, as is generally described in U.S. Pat. Nos. 5,770,029; 5,126,022; 5,631,337; 5,569,364; 5,750,015, and 5,135,627, all of which are hereby incorporated by reference. In electrophoresis, molecules are primarily separated by different electrophoretic mobilities caused by their different molecular size, shape and/or charge. Microcapillary tubes have recently been used for use in microcapillary gel electrophoresis (high performance capillary electrophoresis (HPCE)). One advantage of HPCE is that the heat resulting from the applied electric field is efficiently disappated due to the high surface area, thus allowing fast separation. The electrophoresis module serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the electrophoresis module can take on a variety of forms, and generally comprises an electrophoretic microchannel and associated electrodes to apply an electric field to the electrophoretic microchannel. Waste fluid outlets and fluid reservoirs are present as required.

The electrodes comprise pairs of electrodes, either a single pair, or, as described in U.S. Pat. Nos. 5,126,022 and 5,750,015, a plurality of pairs. Single pairs generally have one electrode at each end of the electrophoretic pathway. Multiple electrode pairs may be used to precisely control the movement of sample components, such that the sample components may be continuously subjected to a plurality of electric fields either simultaneously or sequentially.

In a preferred embodiment, electrophoretic gel media may also be used. By varying the pore size of the media, employing two or more gel media of different porosity, and/or providing a pore size gradient, separation of sample components can be maximized. Gel media for separation based on size are known, and include, but are not limited to, polyacrylamide and agarose. One preferred electrophoretic separation matrix is described in U.S. Pat. No. 5,135,627, hereby incorporated by reference, that describes the use of "mosaic matrix", formed by polymerizing a dispersion of microdomains ("dispersoids") and a polymeric matrix. This allows enhanced separation of target analytes, particularly nucleic acids. Similarly, U.S. Pat. No. 5,569,364, hereby incorporated by reference, describes separation media for electrophoresis comprising submicron to above-micron sized cross-linked gel particles that find use in microfluidic systems. U.S. Pat. No. 5,631,337, hereby incorporated by reference, describes the use of thermoreversible hydrogels comprising polyacrylamide backbones with N-substituents that serve to provide hydrogen bonding groups for improved electrophoretic separation. See also U.S. Pat. Nos. 5,061,336 and 5,071,531, directed to methods of casting gels in capillary tubes.

In a preferred embodiment, the devices of the invention include a reaction module. This can include either physical, chemical or biological alteration of one or more sample components. Alternatively, it may include a reaction module wherein the target analyte alters a second moiety that can then be detected; for example, if the target analyte is an enzyme, the reaction chamber may comprise an enzyme substrate that upon modification by the target analyte, can then be detected. In this embodiment, the reaction module may contain the necessary reagents, or they may be stored in a storage module and pumped as outlined herein to the reaction module as needed.

In a preferred embodiment, the reaction module includes a chamber for the chemical modification of all or part of the sample. For example, chemical cleavage of sample components (CNBr cleavage of proteins, etc.) or chemical cross-linking can be done. PCT US97/07880, hereby incorporated by reference, lists a large number of possible chemical reactions that can be done in the devices of the invention, including amide formation, acylation, alkylation, reductive amination, Mitsunobu, Diels Alder and Mannich reactions, Suzuki and Stille coupling, chemical labeling, etc. Similarly, U.S. Pat. Nos. 5,616,464 and 5,767,259 describe a variation of LCR that utilizes a "chemical ligation" of sorts. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts as one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes. At least one of the side chains of the primers comprises an activatable cross-linking agent, generally covalently attached to the side chain, that upon activation, results in a chemical cross-link or chemical ligation. The activatible group may comprise any moiety that will allow cross-linking of the side chains, and include groups activated chemically, photonically and thermally, with photo-activatable groups being preferred. In some embodiments a single activatable group on one of the side chains is enough to result in cross-linking via interaction to a functional group on the other side chain; in alternate embodiments, activatable groups are required on each side chain. In addition, the reaction chamber may contain chemical moieties for the protection or deprotection of certain functional groups, such as thiols or amines.

In a preferred embodiment, the reaction module includes a chamber for the biological alteration of all or part of the sample. For example, enzymatic processes including nucleic acid amplification, hydrolysis of sample components or the hydrolysis of substrates by a target enzyme, the addition or removal of detectable labels, the addition or removal of phosphate groups, etc.

In a preferred embodiment, the target analyte is a nucleic acid and the biological reaction chamber allows amplification of the target nucleic acid. Suitable amplification techniques include, both target amplification and probe amplification, including, but not limited to, polymerase chain reaction (PCR), ligase chain reaction (LCR), strand displacement amplification (SDA), self-sustained sequence replication (3SR), QB replicase amplification (QBR), repair chain reaction (RCR), cycling probe technology or reaction (CPT or CPR), and nucleic acid sequence based amplification (NASBA). In this embodiment, the reaction reagents generally comprise at least one enzyme (generally polymerase), primers, and nucleoside triphosphates as needed.

General techniques for nucleic acid amplification are discussed below. In most cases, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques such as the use of extra probes or nucleic acid binding proteins may also be used. Thus, as more fully described below, the reaction chambers of the invention can include thermal modules.

A probe nucleic acid (also referred to herein as a primer nucleic acid) is then contacted to the target sequence to form a hybridization complex. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique.

In addition, the different amplification techniques may have further requirements of the primers, as is more fully described below.

Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identification of the enzyme will depend on the amplification technique used, as is more fully outlined below. Similarly, the modification will depend on the amplification technique, as outlined below, although generally the first step of all the reactions herein is an extension of the primer, that is, nucleotides are added to the primer to extend its length.

Once the enzyme has modified the primer to form a modified primer, the hybridization complex is disassociated. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

After a suitable time or amplification, the modified primer can be moved to a detection module and detected.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), and nucleic acid sequence based amplification (NASBA).

In a preferred embodiment, the target amplification technique is PCR. The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtration", among others. In one embodiment, the amplification technique is not PCR.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostabile polymerase such as Taq I polymerase and thermal cycling.

Accordingly, the PCR reaction requires at least one PCR primer and a polymerase.

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25–100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'-O-(1-thiotriphosphate), 5-methyldeoxycytidine 5'-triphosphate, 2'-deoxyuridine 5'-triphosphate, adn 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'→3' exonuclease activity. However, if less than all the nucleotides are substituted, the polymerase preferably lacks 5'→3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindII, AvaI, Fnu4HI, TthlII, NclI, BstXI, BamI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'→3', thereby creating another newly synthesized strand. The polymerase chosen should be able to intiate 5'→3' polymerization at a nick site, should also displace the polymerized strand downstream from the nick, and should lack 5'→3'exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261–285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template"), is contacted with a first primer, generally referred to herein as a "NASBA primer" (although "TMA primer" is also suitable). Starting with a DNA target sequence is described below. These primers generally have a length of 25–100 nucleotides, with NASBA primers of approximately 50–75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf thymus.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPS) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage ϕII, Salmonella phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

In a preferred embodiment, the amplification technique is signal amplification. Signal amplification involves the use of limited number of target molecules as templates to either generate multiple signalling probes or allow the use of multiple signalling probes. Signal amplification strategies include LCR, CPT, Invader™, and the use of amplification probes in sandwich assays.

In a preferred embodiment, the signal amplification technique is the oligonucleotide ligation assay (OLA), sometimes referred to as the ligation chain reaction (LCR). The method can be run in two different ways; in a first embodiment, only one strand of a target sequence is used as a template for ligation (OLA); alternatively, both strands may be used (OLA). See generally U.S. Pat. Nos. 5,185,243 and 5,573,907; EP 0 320 308 B1; EP 0 336 731 B1; EP 0 439 182 B1WO 90/01069; WO 89/12696; and WO 89/09835, and U.S. S. Nos. 60/078,102 and 60/073,011, all of which are incorporated by reference.

In a preferred embodiment, the single-stranded target sequence comprises a first target domain and a second target domain, and a first LCR primer and a second LCR primer nucleic acids are added, that are substantially complementary to its respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two LCR primers are then covalently attached, for example using a ligase enzyme such as is known in the art. This forms a first hybridization complex comprising the ligated probe and the target sequence. This hybridization complex is then denatured (disassociated), and the process is repeated to generate a pool of ligated probes.

In a preferred embodiment, LCR is done for two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

A variation of LCR utilizes a "chemical ligation" of sorts, as is generally outlined in U.S. Pat. Nos. 5,616,464 and 5,767,259, both of which are hereby expressly incorporated by reference in their entirety. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes.

At least one of the side chains of the primers comprises an activatable cross-linking agent, generally covalently attached to the side chain, that upon activation, results in a chemical cross-link or chemical ligation. The activatible group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the disassocation of the hybridization complex, thus freeing up the target to serve as a template for the next ligation or cross-linking. In this way, signal amplification occurs, and can be detected as outlined herein.

In a preferred embodiment the signal amplification technique is RCA. Rolling-circle amplification is generally described in Baner et al. (1998) *Nuc. Acids Res.* 26:5073–5078; Barany, F. (1991) *Proc. Natl. Acad. Sci. USA* 88:189–193; Lizardi et al. (1998) *Nat. Genet.* 19:225–232; Zhang et al., Gene 211:277 (1998); and Daubendiek et al., Nature Biotech. 15:273 (1997); all of which are incorporated by reference in their entirety.

In general, RCA may be described as follows. First, as is outlined in more detail below, a single RCA probe is hybridized with a target nucleic acid. Each terminus of the probe hybridizes adjacently on the target nucleic acid (or alternatively, there are intervening nucleotides that can be "filled in" using a polymerase and dNTPs, as outlined below) and the OLA assay as described above occurs. When ligated, the probe is circularized while hybridized to the target nucleic acid. Addition of a primer, a polymerase and dNTPs results in extension of the circular probe. However, since the probe has no terminus, the polymerase continues to extend the probe repeatedly. Thus results in amplification of the circular probe. This very large concatamer can be detected intact, as described below, or can be cleaved in a variety of ways to form smaller amplicons for detection as outlined herein.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent (either directly or indirectly, as outlined herein) to the first domain. Hybridization of the probe to the target nucleic acid results in the formation of a hybridization complex. Ligation of the "primers" (which are the discrete ends of a single oligonucleotide, the RCA probe) results in the formation of a modified hybridization complex containing a circular probe i.e. an RCA template complex. That is, the oligonucleotide is circularized while still hybridized with the target nucleic acid. This serves as a circular template for RCA. Addition of a primer, a polymerase and the required dNTPs to the RCA template complex results in the formation of an amplified product nucleic acid. Following RCA, the amplified product nucleic acid is detected as outlined herein. This can be accomplished in a variety of ways; for example, the polymerase may incorporate labeled nucleotides; a labeled primer may be used, or alternatively, a label probe is used that is substantially complementary to a portion of the RCA probe and comprises at least one label is used.

Accordingly, the present invention provides RCA probes (sometimes referred to herein as "rolling circle probes (RCPs) or "padlock probes" (PPs)). The RCPs may comprise any number of elements, including a first and second ligation sequence, a cleavage site, a priming site, a capture sequence, nucleotide analogs, and a label sequence.

In a preferred embodiment, the RCP comprises first and second ligation sequences. As outlined above for OLA, the ligation sequences are substantially complementary to adjacent domains of the target sequence. The domains may be directly adjacent (i.e. with no intervening bases between the 3' end of the first and the 5' of the second) or indirectly adjacent, with from 1 to 100 or more bases in between.

In a preferred embodiment, the RCPs comprise a cleavage site, such that either after or during the rolling circle amplification, the RCP concatamer may be cleaved into amplicons. In some embodiments, this facilitates the detection, since the amplicons are generally smaller and exhibit favorable hybridization kinetics on the surface. As will be appreciated by those in the art, the cleavage site can take on a number of forms, including, but not limited to, the use of restriction sites in the probe, the use of ribozyme sequences, or through the use or incorporation of nucleic acid cleavage moieties.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA (or in some cases, during the reaction), the product nucleic acid is contacted with the appropriate restriction endonuclease. This results in cleavage of the product nucleic acid into smaller fragments. The fragments are then hybridized with the capture probe that is immobilized resulting in a concentration of product fragments onto the detection electrode. Again, as outlined herein, these fragments can be detected in one of two ways: either labelled nucleotides are incorporated during the replication step, for example either as labeled individual dNTPs or through the use of a labeled primer, or an additional label probe is added.

In a preferred embodiment, the restriction site is a single-stranded restriction site chosen such that its complement occurs only once in the RCP.

In a preferred embodiment, the cleavage site is a ribozyme cleavage site as is generally described in Daubendiek et al., Nature Biotech. 15:273 (1997), hereby expressly incorporated by reference. In this embodiment, by using RCPs that encode catalytic RNAs, NTPs and an RNA polymerase, the resulting concatamer can self cleave, ultimately forming monomeric amplicons.

In a preferred embodiment, cleavage is accomplished using DNA cleavage reagents. For example, as is known in the art, there are a number of intercalating moieties that can effect cleavage, for example using light.

In a preferred embodiment, the RCPs do not comprise a cleavage site. Instead, the size of the RCP is designed such that it may hybridize "smoothly" to many capture probes on a surface. Alternatively, the reaction may be cycled such that very long concatamers are not formed.

In a preferred embodiment, the RCPs comprise a priming site, to allow the binding of a DNA polymerase primer. As is known in the art, many DNA polymerases require double stranded nucleic acid and a free terminus to allow nucleic acid synthesis. However, in some cases, for example when RNA polymerases are used, a primer may not be required (see Daubendiek, supra). Similarly, depending on the size and orientation of the target strand, it is possible that a free end of the target sequence can serve as the primer; see Baner et al., supra.

Thus, in a preferred embodiment, the padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

In a preferred embodiment, the primer may comprise the covalently attached ETMs.

In a preferred embodiment, the RCPs comprise a capture sequence. A capture sequence, as is outlined herein, is substantially complementary to a capture probe, as outlined herein.

In a preferred embodiment, the RCPs comprise a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

In a preferred embodiment, the RCP/primer sets are designed to allow an additional level of amplification, sometimes referred to as "hyperbranching" or "cascade amplification". As described in Zhang et al., supra, by using several priming sequences and primers, a first concatamer can serve as the template for additional concatamers. In this embodiment, a polymerase that has high displacement activity is preferably used. In this embodiment, a first antisense primer is used, followed by the use of sense primers, to generate large numbers of concatamers and amplicons, when cleavage is used.

Thus, the invention provides for methods of detecting using RCPs as described herein. Once the ligation sequences of the RCP have hybridized to the target, forming a first hybridization complex, the ends of the RCP are ligated together as outlined above for OLA. The RCP primer is added, if necessary, along with a polymerase and dNTPs (or NTPs, if necessary).

The polymerase can be any polymerase as outlined herein, but is preferably one lacking 3' exonuclease activity (3' exo⁻). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

Thus, in a preferred embodiment the OLA/RCA is performed in solution followed by restriction endonuclease cleavage of the RCA product. The cleaved product is then applied to an array as described herein. The incorporation of an endonuclease site allows the generation of short, easily hybridizable sequences. Furthermore, the unique capture sequence in each rolling circle padlock probe sequence allows diverse sets of nucleic acid sequences to be analyzed in parallel on an array, since each sequence is resolved on the basis of hybridization specificity.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template.

The RCA as described herein finds use in allowing highly specific and highly sensitive detection of nucleic acid target sequences. In particular, the method finds use in improving the multiplexing ability of DNA arrays and eliminating costly sample or target preparation. As an example, a substantial savings in cost can be realized by directly analyzing genomic DNA on an array, rather than employing an intermediate PCR amplification step. The method finds use in examining genomic DNA and other samples including mRNA.

In addition the RCA finds use in allowing rolling circle amplification products to be easily detected by hybridization to probes in a solid-phase format. An additional advantage of the RCA is that it provides the capability of multiplex analysis so that large numbers of sequences can be analyzed in parallel. By combining the sensitivity of RCA and parallel detection on arrays, many sequences can be analyzed directly from genomic DNA.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected as outlined herein.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

In one embodiment, the entire scissile probe is made of RNA, the nicking is facilitated especially when carried out with a double-stranded ribonuclease, such as RNAseH or Exo III. RNA probes made entirely of RNA sequences are particularly useful because first, they can be more easily produced enzymatically, and second, they have more cleavage sites which are accessible to nicking or cleaving by a nicking agent, such as the ribonucleases. Thus, scissile probes made entirely of RNA do not rely on a scissile linkage since the scissile linkage is inherent in the probe.

In a preferred embodiment, Invader™ technology is used. Invader™ technology is based on structure-specific polymerases that cleave nucleic acids in a site-specific manner.

Two probes are used: an "invader" probe and a "signaling" probe, that adjacently hybridize to a target sequence with a non-complementary overlap. The enzyme cleaves at the overlap due to its recognition of the "tail", and releases the "tail". This can then be detected. The Invader™ technology is described in U.S. Pat. Nos. 5,846,717; 5,614,402; 5,719,028; 5,541,311; and 5,843,669, all of which are hereby incorporated by reference.

Accordingly, the invention provides a first primer, sometimes referred to herein as an "invader primer", that hybridizes to a first domain of a target sequence, and a second primer, sometimes referred to herein as the signaling primer, that hybridizes to a second domain of the target sequence. The first and second target domains are adjacent. The signaling primer further comprises an overlap sequence, comprising at least one nucleotide, that is perfectly complementary to at least one nucleotide of the first target domain, and a non-complementary "tail" region. The cleavage enzyme recognizes the overlap structure and the noncomplementary tail, and cleaves the tail from the second primer. Suitable cleavage enzymes are described in the Patents outlined above, and include, but are not limited to, 5' thermostable nucleases from Thermus species, including *Thermus aquaticus, Thermus flavus* and *Thermus thermophilus*. The entire reaction is done isothermally at a temperature such that upon cleavage, the invader probe and the cleaved signaling probe come off the target stand, and new primers can bind. In this way large amounts of cleaved signaling probe (i.e. "tails") are made. The uncleaved signaling probes are removed (for example by binding to a solid support such as a bead, either on the basis of the sequence or through the use of a binding ligand attached to the portion of the signaling probe that hybridizes to the target). The cleaved signalling probes are then detected as outlined herein.

In this way, a number of target molecules are made. As is more fully outlined below, these reactions (that is, the products of these reactions) can be detected in a number of ways, as is generally outlined in U.S. Ser. Nos. 09/458,553; 09/458,501; 09/572,187; 09/495,992; 09/344,217; WO00/31148; 09/439,889; 09/438,209; 09/344,620; PCTUS00/17422; 09/478,727, all of which are expressly incorporated by reference in their entirety.

In a preferred embodiment, detection proceeds through the use of labels. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis [(dimethylimino-3,1-propanediyl]]bis[4-[(3-methyl-2(3H)-benzoxazolylidene)methyl]]-tetraioide, which is sold under the name YOYO-1, and others described in the 6th Edition of the Molecular Probes Handbook by Richard P. Haugland, hereby expressly incorporated by reference. In addition, redox active labels may also be used when electronic detection systems are used.

In some embodiments, fluorochromes or other labels are added to the newly synthesized strands, either by incorporating the labels into the primers, incorporating them using labeled dNTPs that are enzymatically incorporated into the newly synthesized strand, or through the use of other known methods, including the use of hybridization indicators. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up.

In a preferred embodiment, the signal amplification technique is a "sandwich" assay, as is generally described in U.S. S. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays are used when the target sequence does not comprise a label; that is, when a secondary probe, comprising labels, is used to generate the signal.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay.

In a preferred embodiment, the reaction modules comprise a thermal module, although as will be recognized by those in the art, there may be embodiments that utilize thermal modules in the absence of reaction modules. Thermal modules can be either part of the reaction chamber or separate but can be brought into spatial proximity to the reaction module. The thermal module can include both heating and/or cooling capability. The thermal module may further comprise devices for monitoring the temperature of each well.

Suitable thermal modules are described in U.S. Pat. Nos. 5,498,392 and 5,587,128, and WO 97/16561, incorporated by reference, and may comprise electrical resistance heaters, pulsed lasers or other sources of electromagnetic energy directed to the reaction chamber. It should also be noted that when heating elements are used, it may be desirable to have the reaction chamber be relatively shallow, to facilitate heat transfer; see U.S. Pat. No. 5,587,128.

When the devices of the invention include thermal modules, preferred embodiments utilize microchip arrays fabricated to have low thermal conductivity in order to minimize thermal crosstalk between adjacent chambers on the microchip, which permits independent thermal control of each microchip component. In preferred embodiments, the microchip of the present invention is fabricated using ceramic multilayer technology (as disclosed herein, for example, as well as in co-owned and co-pending U.S. Ser. Nos. 09/235,081 and 09/337,086, incorporated by reference herein). In additional preferred embodiments, the microchip array comprises air channels for thermally isolating microchip components. In still further preferred embodiments, the microchip array comprises thermal conducting material in thermal contact with each well on the microchip for removing heat therefrom and reducing thermal crosstalk between wells thereby. In some embodiments of the present invention, the biocompatibility of the ceramic material comprising the well structures may be enhanced by coating the microchip with a conformal compound such as parylene that reduces inhibition of the thermal molecular reactions within the ceramic wells.

Particularly preferred embodiments utilize microchips of the invention comprise one or a plurality of wells. Preferably, the microchip possesses an array of wells in which parallel, independently controlled molecular reactions can be controlled by temperature cycling as required. For example, the microchip array of the present invention can be used to perform parallel, independently controlled PCR reactions, ligase chain reactions, or DNA ligations, and others outlined herein. Most preferably, the apparatus of the invention can be used to determine the optimal reaction conditions for the PCR amplification of a particular nucleic acid sequence. Alternatively, the invention can be used to perform multiple reactions under more than one set of amplification conditions.

In certain embodiments, the temperature of the wells is increased using a thermal module comprising an integrated heater. In preferred embodiments, the integrated heater is a resistive heater, and more preferably a thick film resistive heater plate. Alternatively, the wells can be heated through the use of metal lines integrated beneath the well or surrounding sides of the wells, more preferably in a coil having one or more loops, in vertical or horizontal orientation. Parallel, variable heating of individual wells in a microchip array may be accomplished through the use of addressing schemes, preferably a column-and-row or individual electrical addressing scheme, in order to independently control the heat output of the resistive heaters in the vicinity of each well.

In certain embodiments, the temperature of the wells is decreased using a thermal module comprising an integrated cooler. In preferred embodiments, the integrated cooler is a metal via at the bottom of each well. In further preferred embodiments, the integrated cooler is a thermoelectric cooler attached to or integrated into the microchip beneath each well. Optionally, the metal via is in thermal contact with a metal plate, an array of metal discs or a thermoelectric cooler, each of which functions as a heat sink or an active cooling means. Commercially-available thermoelectric coolers can also be incorporated into the inventive apparatus, because they can be obtained in a wide range of dimensions, including components of a size required for the fabrication of the microarrays of the present invention. In embodiments comprising metal heat sinks encompassing a metal plate or an array of metal discs, the plate or discs are composed of iron, aluminum, or other suitable metal. Parallel, variable cooling of individual wells in a microchip array may be accomplished through the use of addressing schemes, preferably a column-and-row or individual electrical addressing scheme, in order to independently control heat dissipation using cooling elements in the vicinity of each well.

In preferred embodiments of the microchip arrays of the invention, the thermal module includes temperature monitors, to monitor the temperature of the well using an integrated resistive thermal detector or a thermocouple. This can be incorporated into the substrate or added later, and is in thermal contact and proximity to the well structures of the microchips of the invention. The resistive thermal detector can be fabricated from a commercially available paste that can be processed in a customized manner for any given design. Such thermocouples are commercially available in sizes of at least 250 microns, including the sheath. In certain alternative embodiments, the temperature of the wells is monitored using an integrated optical system, for example, an infrared-based system.

In certain embodiments of the microchip arrays of the invention, reagents can be deposited in appropriate regions or components, or can be delivered to said components from other components on the microchip as outlined herein. In preferred embodiments, reagents can be delivered to the wells of a microchip array using a microfluidic reagent distribution system as outlined herein. In preferred embodiments, the microfluidic distribution system is controlled by pressure, using pumping means, or by electro-osmotic pumping means, and fluid flow is controlled by valving, using a system of microfluidic channels and chambers to advantageously direct fluid flow on the microchip.

Compared with available prior art devices, the microchip arrays of the present invention will allow for more efficient and inexpensive performance of molecular reactions. For example, the apparatus of the present invention can be used to perform PCR using reduced amounts of reagents in less time and with higher throughput than is possible using any commercially-available PCR machine. In addition, as a result of the fabrication techniques employed in the construction of the apparatus of the present invention, the microchip of the present invention is distinguished from prior art microchips in that an increased number of molecular reactions can be performed on a single microchip array. Finally, the addressable nature of the microchip array of the present invention allows for parallel optimization of molecular reaction conditions or the performance of simultaneous molecular reactions under variant reaction conditions.

In addition to the components outlined above for reaction chambers, as described in U.S. Pat. No. 5,587,128, the reaction chamber may comprise a composition, either in solution or adhered to the surface of the reaction chamber, that prevents the inhibition of an amplification reaction by the composition of the well. For example, the wall surfaces may be coated with a silane, for example using a silanization reagent such as dimethylchlorosilane, or coated with a siliconizing reagent such as Aquasil™ or Surfacil™ (Pierce, Rockford, Ill.), which are organosilanes containing a hydrolyzable group. This hydrolyzable group can hydrolyze in solution to form a silanol that can polymerize and form a tightly bonded film over the surface of the chamber. The coating may also include a blocking agent that can react with the film to further reduce inhibition; suitable blocking agents include amino acid polymers and polymers such as polyvinylpyrrolidone, polyadenylic acid and polymaleimide. Alternatively, for silicon substrates, a silicon oxide film may be provided on the walls, or the reaction chamber can be coated with a relatively inert polymer such as a polyvinylchloride. In addition, it may be desirable to add blocking polynucleotides to occupy any binding sites on the surface of the chamber.

In a preferred embodiment, the biological reaction chamber allows enzymatic cleavage or alteration of the target analyte. For example, restriction endonucleases may be used to cleave target nucleic acids comprising target sequences, for example genomic DNA, into smaller fragments to facilitate either amplification or detection. Alternatively, when the target analyte is a protein, it may be cleaved by a protease. Other types of enzymatic hydrolysis may also be done, depending on the composition of the target analyte. In addition, as outlined herein, the target analyte may comprise an enzyme and the reaction chamber comprises a substrate that is then cleaved to form a detectable product.

In addition, in one embodiment the reaction module includes a chamber for the physical alteration of all or part of the sample, for example for shearing genomic or large nucleic acids, nuclear lysis, ultrasound, etc.

In a preferred embodiment, the devices of the invention include at least one fluid pump. Pumps generally fall into two categories: "on chip" and "off chip"; that is, the pumps (generally electrode based pumps) can be contained within the device itself, or they can be contained on an apparatus into which the device fits, such that alignment occurs of the required flow channels to allow pumping of fluids.

In a preferred embodiment, the pumps are contained on the device itself. These pumps are generally electrode based pumps; that is, the application of electric fields can be used to move both charged particles and bulk solvent, depending on the composition of the sample and of the device. Suitable on chip pumps include, but are not limited to, electroosmotic (EQ) pumps and electrohydrodynamic (EHD) pumps; these electrode based pumps have sometimes been referred to in the art as "electrokinetic (EK) pumps". All of these pumps rely on configurations of electrodes placed along a flow channel to result in the pumping of the fluids comprising the sample components. As is described in the art, the configurations for each of these electrode based pumps are slightly different; for example, the effectiveness of an EHD pump depends on the spacing between the two electrodes, with the closer together they are, the smaller the voltage required to be applied to effect fluid flow. Alternatively, for EQ pumps, the spacing between the electrodes should be larger, with up to one-half the length of the channel in which fluids are being moved, since the electrode are only involved in applying force, and not, as in EHD, in creating charges on which the force will act.

In a preferred embodiment, an electroosmotic pump is used. Electroosmosis (EQ) is based on the fact that the surface of many solids, including quartz, glass and others, become variously charged, negatively or positively, in the presence of ionic materials. The charged surfaces will attract oppositely charged counterions in aqueous solutions. Applying a voltage results in a migration of the counterions to the oppositely charged electrode, and moves the bulk of the fluid as well. The volume flow rate is proportional to the current, and the volume flow generated in the fluid is also proportional to the applied voltage. Electroosmostic flow is useful for liquids having some conductivity is and generally not applicable for non-polar solvents. EQ pumps are described in U.S. Pat. Nos. 4,908,112 and 5,632,876, PCT US95/14586 and WO97/43629, incorporated by reference.

In a preferred embodiment, an electrohydrodynamic (EHD) pump is used. In EHD, electrodes in contact with the fluid transfer charge when a voltage is applied. This charge transfer occurs either by transfer or removal of an electron to or from the fluid, such that liquid flow occurs in the direction from the charging electrode to the oppositely charged electrode. EHD pumps can be used to pump resistive fluids such as non-polar solvents. EHD pumps are described in U.S. Pat. No. 5,632,876, hereby incorporated by reference.

The electrodes of the pumps preferably have a diameter from about 25 microns to about 100 microns, more preferably from about 50 microns to about 75 microns. Preferably, the electrodes protrude from the top of a flow channel to a depth of from about 5% to about 95% of the depth of the channel, with from about 25% to about 50% being preferred. In addition, as described in PCT US95/14586, an electrode-based internal pumping system can be be integrated into the liquid distribution system of the devices of the invention with flow-rate control at multiple pump sites and with fewer complex electronics if the pumps are operated by applying pulsed voltages across the electrodes; this gives the additional advantage of ease of integration into high density systems, reductions in the amount of electrolysis that occurs at electrodes, reductions in thermal convenction near the electrodes, and the ability to use simpler drivers, and the ability to use both simple and complex pulse wave geometries.

The voltages required to be applied to the electrodes cause fluid flow depends on the geometry of the electrodes and the properties of the fluids to be moved. The flow rate of the fluids is a function of the amplitude of the applied voltage between electrode, the electrode geometry and the fluid properties, which can be easily determined for each fluid. Test voltages used may be up to about 1500 volts, but an operating voltage of about 40 to 300 volts is desirable. An analog driver is generally used to vary the voltage applied to the pump from a DC power source. A transfer function for each fluid is determined experimentally as that applied voltage that produces the desired flow or fluid pressue to the fluid being moved in the channel. However, an analog driver is generally required for each pump along the channel and is suitable an operational amplifier.

In a preferred embodiment, a micromechanical pump is used, either on- or off-chip, as is known in the art.

In a preferred embodiment, an "off-chip" pump is used. For example, the devices of the invention may fit into an apparatus or appliance that has a nesting site for holding the device, that can register the ports (i.e. sample inlet ports, fluid inlet ports, and waste outlet ports) and electrode leads. The apparatus can including pumps that can apply the sample to the device; for example, can force cell-containing samples into cell lysis modules containing protrusions, to cause cell lysis upon application of sufficient flow pressure. Such pumps are well known in the art.

In a preferred embodiment, one or more pumps are used to recirculate the sample within the biochannels comprising the arrays, to allow for increased binding of the target analyte to the capture binding ligand. As outlined herein, this can be accomplished in a variety of ways.

In a preferred embodiment, the devices of the invention include at least one fluid valve that can control the flow of fluid into or out of a module of the device, or divert the flow into one or more channels. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediated before the opening into a larger space such a chamber. In addition, as described in U.S. Pat. No. 5,858,195, incorporated herein by reference, a type of "virtual valve" can be used.

In a preferred embodiment, the devices of the invention include sealing ports, to allow the introduction of fluids, including samples, into any of the modules of the invention, with subsequent closure of the port to avoid the loss of the sample.

In a preferred embodiment, the devices of the invention include at least one storage module for assay reagents. These are connected to other modules of the system using flow channels and may comprise wells or chambers, or extended flow channels. They may contain any number of reagents, buffers, enzymes, electronic mediators, salts, etc., including freeze dried reagents.

In a preferred embodiment, the devices of the invention include a mixing module; again, as for storage modules, these may be extended flow channels (particularly useful for timed mixing), wells or chambers. Particularly in the case of extended flow channels, there may be protrusions on the side of the channel to cause mixing.

In addition, as is more fully outlined herein, the modules of the devices of the invention can be formed from the substrate, a spacing surface such as an adhesive layer or gasket (e.g. rubber, silicone, other polymers, etc.), and a flexible cover. In some embodiments, a single flexible layer is used with either single or multiple biochannels; in others, multiple layers are used with multiple biochannels. Again, inlet and outlet ports can be through the substrate or through the flexible layer.

In addition, the systems of the invention that include the devices of the invention can include any number of microfluidic reagent or fluid handling and distribution systems. Thus, in a preferred embodiment, the systems of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well (or higher) loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems such as Peltier systems are used for stabilizing the temperature of the heat exchangers such as controlled blocks or platforms to provide accurate temperature control of incubating samples from 40° C. to 100° C.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the presence or absence of labels and the assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluroescence resonance energy transfer (FRET), luminescence, quenching, two-photon excitation, and intensity redistribution; electronic detection systems; CCD cameras to capture and transform data and images into quantifiable formats; a computer workstation; and one or more barcode readers.

These instruments can fit in a sterile laminar flow or fume hood, or are enclosed, self-contained systems, for cell culture growth and transformation in multi-well plates or tubes and for hazardous operations. Similarly, operations can be performed under controlled environments such as inert gas (for example to prevent lipid oxidation). The living cells will be grown under controlled growth conditions, with controls for temperature, humidity, and gas for time series of the live cell assays. Automated transformation of cells and automated colony pickers will facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. As discussed herein, this may be in addition to or in place of the CPU for the FTMS data analysis. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, supercritical fluids and gases (particularly for extraction), samples, washes, assay components, etc. Similarly, when the sample is limited, all components (capillaries, connections, etc.) can be minimized to avoid large dead volumes or dilution effects.

In a preferred embodiment, the devices of the invention include a detection module. The present invention is directed to methods and compositions useful in the detection of biological target analyte species such as nucleic acids and proteins as outlined herein. Suitable detection methods are described in U.S. Ser. Nos. 09/458,553; 09/458,501; 09/572,187; 09/495,992; 09/344,217; WO00/31148; 09/439,889; 09/438,209; 09/344,620; PCTUS00/17422; 09/478,727, all of which are expressly incorporated by reference in their entirety.

In a preferred embodiment, the devices of the invention further comprise a reusable reaction apparatus that has one or more biologically inert reaction chambers into which biologically reactive sample fluid mixtures are introduced. The sample can thus be introduced to one or more biochips.

In this embodiment, the invention broadly comprises a base plate having a first surface and a cavity disposed in the first surface, wherein the cavity comprises one or more well structures and a biochip comprising one or more microarrays of biologically reactive sites disposed on a first surface can be inserted into the apparatus such that the first surface of the biochip is in direct communication with the well structures and is removably clamped to the base plate using a compression plate. A sealing member is disposed between the first surface of the substrate and the first surface of the base plate in each well structure, thereby defining one or more reaction chambers. Each well structure has at least two fluid ports for introducing fluid samples into and removing fluid samples from the reaction chambers. The invention further comprises a seal for the fluid ports.

A preferred embodiment of the invention is configured to accommodate a biochip comprising a standard microscope slide having a plurality of hydrogel-based microarrays attached thereto. A further preferred embodiment of the apparatus includes the biochip. By "biochip" herein is meant one or more microarrays of capture binding ligands or biologically reactive sites immobilized on the surface of a substrate such as those outlined herein. By "binding ligand" or grammatical equivalents herein is meant a compound that is used to probe for the presence of the target analyte, and that will bind to the analyte. "Capture binding ligands" are generally bound (preferably covalently) to a surface of the substrate, or to a hydrogel on the surface. Preferred microarrays include those outlined in U.S. Ser. Nos. 09/458,553; 09/458,501; 09/572,187; 09/495,992; 09/344,217; WO00/31148; 09/439,889; 09/438,209; 09/344,620; PCTUS00/17422; 09/478,727, all of which are expressly incorporated by reference in their entirety.

In preferred embodiments of the present invention, the sealing member around the perimeter of each well structure comprises an O-ring or sheet of gasket material.

In further preferred embodiments, the fluid ports allow introduction of fluid sample via a standard pipet tip or tubing. In still further preferred embodiments, the fluid ports allow interface to an external pumping system that provides mixing and pressurization of the fluid in each reaction chamber to provide uniform target molecule concentration and dissolve gas bubbles, respectively.

In preferred embodiments, the fluid port seal comprises a layer of flexible, thermally conductive material on which is disposed a layer of pressure-sensitive adhesive.

In other preferred embodiments of the invention, the biological compatibility of the base plate material is enhanced by the addition of a biologically compatible surface coating to the first surface of the base plate. The adhesion of the surface coating to the first surface of the base plate may be further enhanced by application of a layer of primer on the first surface of the base plate prior to application of the surface coating.

In further preferred embodiments of the invention, the compression plate is removably affixed to the base plate by a plurality of retaining pins disposed along the perimeter of the base plate which fit into corresponding locking apertures disposed along the perimeter of the retaining plate. In yet further preferred embodiments, the compression plate comprises a cavity wherein a compliance layer is seated.

In preferred embodiments of the microfluidic reaction apparatus, the retaining plate, compression plate and compliance layer further comprise one or more viewing ports corresponding in position to the reaction chambers for observation or detection of the biological reactions taking place inside the reaction chambers.

The invention is advantageously used for performing thermally controlled biological reactions, and in preferred embodiments comprises a heating element and a thermal cycling device.

In a preferred embodiment, the devices comprise microchips comprising one or a plurality of well structures, a cover or substance to seal the wells, a thermal module including a temperature monitor for each well, as well as the other components outlined herein, particular reagent storage modules.

Regarding the flexible array embodiments, a number of preferred embodiments follow and are depicted in the Figures.

A preferred embodiment includes a PCR microchip. The microchip is built on a layer of thermal insulating material that is most preferably made of glass, silicon, plastic, or ceramic. In a preferred embodiment, this layer is made of ceramic. As ceramic materials are intrinsically good thermal insulators, a thermal insulating layer made of ceramic provides good well-to-well thermal insulation that is a requirement for performing parallel, independent PCR amplifications on a single microchip. As the thermal conductivity of silicon is about eleven times greater than that of ceramics, the multilayer ceramic microarray of the present invention has an advantage over prior art devices constructed of silicon in that an increased number of well structures for performing molecular reactions may be placed onto an array of significantly reduced size. In addition, the multilayer ceramic microarrays of the present invention have an advantage over prior art devices constructed of silicon in that electrical cross-talk is lower in the ceramic microarrays. Furthermore, the ceramic microarrays of the present invention are more biocompatible than the silicon microarrays of prior art devices.

The microchip of the present invention contains one or more well structures, in which nucleic acid amplifications such as PCR can be performed. In some embodiments well structures are formed from a thermal conducting material such as undoped silicon, metals, or modified plastics. In preferred embodiments, the well structures are formed from metals. In more preferred embodiments the metal is silver or silver palladium (containing up to 30% palladium). In other preferred embodiments, the well structures are formed from copper, Ni-Molybdenum, platinum, or gold. Typical formulations of such materials for the fabrication of the well structures of the apparatus of the present invention can be obtained from thick film manufacturers such as DuPont (Research Triangle Park, N.C.) or Hereaus (West Conshohocken, Pa.).

Well structures comprised of a thermal conducting material are separated on the microchip by channels comprising thermal insulating material such as glass, silicon, plastic, ceramic, or air contained in air channel components of the microchip. As used herein, channels and microchannels can contain fluids or gasses, and can be used to move fluids or gasses between components on the microchip.

In a preferred embodiment, the thermal insulating material used to separate the well structures comprises air contained in the air channels. In one preferred embodiment, the air channels have a width of at least 75 microns. Since air has a poor thermal conductivity, air channels of this dimension are useful in reducing the thermal cross-talk between the plurality of well structures of the microchip array of the present invention. Furthermore, the multilayer ceramic microarrays of the present invention have an advantage over prior art devices constructed of silicon in that the fabrication of air channels produces a channel of more uniform dimensions.

Where air channels are used for thermal insulation in the multilayer microfluidics devices of the present invention, the channels can be, for example, cylinders, rectangles, or squares, or any other convenient or useful cross-sectional shape, and the channels are limited by the requirement that at least one vertex is attached to the green-sheet layer from which the channel has been formed. As a result of this limitation, air structures in the microchip array of the present invention are not fabricated to completely surround any well structure without permitting at least one vertex between the well structure and the green-sheet layer to be maintained.

An integrated temperature sensor or thermosensor monitors the temperature of each of the well structures on the microchips of the invention. In preferred embodiments, the integrated thermosensor is a thermoelectric, optical or electrochemical sensor. Alternatively, the temperature of the well is monitored using an integrated resistive thermal detector or a thermocouple, advantageously molded into the microchip substrate in thermal contact and proximity to the well structures of the microchips of the invention.

In a preferred embodiment, a cover seals the PCR microchip of the present invention. In some embodiments, certain components of the heating, cooling, or temperature monitoring systems are integrated into the cover. In still other embodiments of the present invention, a separate heating system to prevent condensation of the reaction mixture onto the cover is incorporated into the cover itself. Alternatively, a covering of mineral oil in individual wells can be used in place of the cover of the preferred embodiment.

A preferred embodiment of the microchips of the present invention is a PCR microchip array comprising a plurality of well structures in which parallel, independent amplification reactions can be performed. In certain and preferred embodiments, heating of the microchip array is accomplished through column-and-row electrical addressing of individual well structures. In alternative preferred embodiments, the well structures are each individually addressed. FIG. 15 illustrates a schematic representation of a microchip array with column-and-row electrical addressing. FIG. 16 illustrates a schematic representation of a microchip array with individual cell electrical addressing. In contrast to column-and-row addressing, an individual addressing configuration allows for the independent heating of each individual well structure.

To fabricate glass or silicon microchips for use in parallel, independently controlled molecular reactions a complex arrangement of heating elements would be required. However, in a preferred embodiment, multilayer ceramics technology permits electrical connections to individual well structures to be distributed three-dimensionally in the microchip.

FIG. 17 is a schematic representation of a cross-sectional view of one embodiment of the well structure and integrated heating and cooling elements associated therewith of the microchip array of the present invention. In this embodiment of the present invention, the heating elements are wrapped around the perimeter of the well and form a spiral from top to bottom.

The integrated heaters of the well structures can be fabricated from metallic pastes containing metal particles, such as silver, platinum, gold, copper, tungsten, nickel, tin, or alloys thereof. Preferably the integrated heaters are fabricated from a metallic paste that is silver. In preferred embodiments, the integrated heaters comprise a lead that is about 30 wide mil, connected to a resistive heater that is about 5 mil wide.

Also provided are resistive thermal devices, for monitoring the thermal energy and temperature produced by the resistive heaters. The RTD, that senses the heat produced by the heater, has a lead that is 10–20 mil wide, a body of the RTD is 5 mil wide and is about 8–15 microns thick.

In a preferred embodiment of the present invention, the supporting substrate has a surface area of between 1 and 100 $cm^2$ containing between 1 and 500 well structures having the shape and dimensions as disclosed herein. In the most preferred embodiments, the well structures are arranged on the substrate so as to be separated by a distance of between 0.1 to 10 mm. In more preferred embodiments, the well structures are separated by channels of insulated material having the shape and dimensions as disclosed herein and the channels and well structures are separated by a distance of between 0.1 and 10 mm. Most preferably, the well structures are regularly spaced on the solid substrate with a uniform spacing there between.

Another preferred embodiment is described in the FIG. 8 with a microfluidic DNA analysis system 10, in accordance with a preferred embodiment of the present invention. A sample inlet port 12 is in fluid communication with a cell lysis chamber 14, and cell lysis chamber 14 is in fluid communication with a DNA separation chamber 16. A buffer injection port 18 and a waste outlet port 20 are preferably provided in fluid communication with DNA separation chamber 16. A DNA amplification chamber 22 is in fluid communication with DNA separation chamber 16. A reagent injection port 24 and a waste outlet port 26 are preferably provided in fluid communication with DNA amplification chamber 22. Finally, a DNA detection system 28 is in fluid communication with DNA amplification chamber 22.

Preferably, a first fluid flow control system 30 is provided between cell lysis chamber 14 and DNA separation chamber 16 and a second fluid flow control system 32 is provided between DNA separation chamber 16 and DNA amplification chamber 22. A third fluid control system 34 may also be provided between DNA amplification chamber 22 and DNA detection system 28. Fluid flow control systems 30–34 serve to control the flow of fluid there through, thereby facilitating control over the flow of fluid through system 10, such as the flow of fluid from one chamber to another. Fluid flow control systems 30–34 can comprise microfluidic pumping systems, such as electroosmotic pumping systems. In particular, when an electroosmotic pumping system is provided as a pair of electrodes disposed in a microfluidic channel, little or no fluid flow occurs in the channel until the electroosmotic pumping system is turned on. Alternatively, fluid flow control systems 30–34 can comprise capillary stop valves. In the capillary stop valve approach, a discontinuity in the channel, such as an abrupt decrease in channel cross-section or the presence of a hydrophobic region, substantially prevents the passage of fluid until a sufficiently high pressure is applied.

In operation, DNA analysis system 10 extracts DNA from a small sample of cells, amplifies the extracted DNA, and then characterizes the amplified DNA, such as by detecting the presence of particular nucleotide sequences. Specifically, a fluidic sample containing the cells to be analyzed is introduced into system 10 through sample inlet port 12. From port 12, the sample enters cell lysis chamber 14. In chamber 14, the cells in the sample are lysed to release their cell contents, most notably the DNA contained in the cells. The cell lysis is preferably performed by subjecting the cells in chamber 14 to pulses of a high electric field strength, typically in the range of about 1 kV/cm to 10 kV/cm. However, other methods could also be used for cell lysis, such as chemical or thermal cell lysis.

After cell lysis, fluid flow control system 30 allows the fluid containing the cell contents to pass to DNA separation chamber 16. In chamber 16, the DNA from the cells is separated from the other cell contents. Preferably, the DNA separation is accomplished by manipulating paramagnetic micro-beads. Paramagnetic beads can be manipulated using magnetic fields, as the beads preferentially collect in areas of high magnetic field strength. Thus, the paramagnetic beads can be entrained in chamber 16 by the application of a magnetic field. However, when the magnetic field is turned off, the beads are able to move though the fluid in chamber 16.

The preferred paramagnetic beads have typical diameters in the range of 2.8 to 5 microns and preferentially adsorb duplex DNA under high salt (e.g., 3 to 4 molar $Na^+$) conditions. Suitable commercially available paramagnetic beads include Dynabeads DNA DIRECT™ from Dynal, Inc., Oslo, Norway and MPG borosilicate glass micro-beads, product number MCPG0502, from CPG, Inc., Lincoln Park, N.J.

The paramagnetic beads are used to separate the DNA from the unwanted cell contents in the following way. First, fluid containing the paramagnetic beads is introduced into chamber 16, such as through buffer injection port 18. The amount of paramagnetic beads to be added will depend on the amount of DNA that is anticipated will be recovered from the sample and on the rated DNA loading capacity for the particular beads used. The beads are allowed to mix with the cell contents in chamber 16 for a few minutes. A magnetic field is then applied to chamber 16 to immobilize the paramagnetic beads. With the beads immobilized, the material in chamber 16 is exposed to a flow of a high salt buffer solution, typically about 3 to 4 molar $Na^+$, that is introduced through buffer injection port 18. In this flow, the buffer and unwanted cell contents are flushed out of chamber 16 through waste outlet port 20. However, under these high salt conditions, the DNA from the cells remains adsorbed on the surfaces of the paramagnetic beads. Moreover, during this high salt wash step, the paramagnetic beads are entrained in chamber 16 by the magnetic field.

After the high salt wash step, a low salt buffer, typically about 10 millimolar $Na^+$, is introduced into chamber 16 through buffer injection port 18. Under these low salt condition, the DNA elutes from the paramagnetic beads. With the paramagnetic beads entrained in chamber 16 by the use of the magnetic field, fluid flow control system 32 allows the low salt buffer containing the eluted DNA to pass to amplification chamber 22.

The DNA in chamber 22 is amplified, preferably by using the polymerase chain reaction (PCR). PCR is a well-known process whereby the amount of DNA can be amplified by factors in the range of $10^6$ to $10^8$. In the PCR process, the DNA is subjected to many cycles (typically about 20 to 40 cycles) of a specific temperature regimen, during which the DNA is exposed to a thermostable polymerase, such as AmpliTaq™ DNA polymerase from Perkin-Elmer, Inc., a mixture of deoxynucleoside triphosphates, and single-stranded oligonucleotide primers (typically about 15 to 25 bases in length). Each cycle comprises a thermal denaturation step, a primer annealing step, and a primer extension step. During the thermal denaturation step, double-stranded DNA is thermally converted to single-stranded DNA. The thermal denaturation step is typically performed at a temperature of 92 to 95° C. for 30 to 60 seconds. During the annealing step, the primers specifically anneal to portions of the single-stranded DNA. The annealing is typically performed at a temperature of 50 to 60° C. for about 30 seconds. During the primer extension step, the mononucleotides are incorporated into the annealed DNA in the 5' to 3' direction. The primer extension step is typically performed at 72° C. for 30 seconds to several minutes, depending on the characteristics of the nucleotide sequences that are involved. The result of each complete cycle is the generation of two exact copies of each original duplex DNA molecule.

The PCR process is conducted in chamber 22 to amplify the DNA introduced from chamber 16. Specifically, the polymerase and other reagents needed to perform PCR are added to chamber 22 through reagent injection port 24. The temperature of chamber 22 is adjusted to perform the various steps in the PCR process, as described above, for a desired number of cycles. Heating and cooling elements may be provided in thermal contact with chamber 22 for adjusting its temperature as required.

After PCR, fluid flow control system 34 allows the amplified DNA to pass to DNA detection system 28. DNA detection system 28 can include a capillary electrophoresis device, in which case the amplified products would be characterized by their electrophoretic mobility. The DNA in the capillary electrophoresis device could be detected electrically at one or more locations along the electrophoresis channel. Preferably, however, the DNA is detected optically, such as by laser-induced fluorescence. For this approach, a fluorophore is added to chamber 22, such as through reagent injection port 24, and allowed to conjugate with the amplified DNA before the amplified DNA is introduced into the capillary electrophoresis device.

Alternatively, DNA detection system 28 may include a molecular probe array, such as in DNA detection system 50 shown schematically in FIG. 9. System 50 includes a molecular probe array 52 comprising a plurality of test sites 54 formed into a substrate 56. Each one of test sites 54 contains known probe molecules, such as oligonucleotides, that are able to hybridize with a specific nucleotide sequence that may be present in the amplified DNA to which it is exposed. Preferably, the probe molecules are immobilized in a gel, such as a polyacrylamide gel, in each of test sites 54. By detecting in which one of test sites 54 hybridization occurs, the nucleotide sequences present in the amplified DNA can be determined. Detecting such hybridization can be accomplished by detecting changes in the optical or electrical properties of the test site in which hybridization occurs.

Preferably, hybridization is detected optically. To allow for optical detection, the amplified DNA is preferably conjugated to a fluorophore, such as YOYO-1 before being introduced to the molecular probe array, as described above. Then, a source 58 produces electromagnetic radiation at an excitation wavelength, i.e., a wavelength that induces fluorescence in the fluorophore, and a source optical system 60 focuses this electromagnetic radiation onto test sites 54. The fluorescence radiation from test sites 54 is then focused onto a detector 62 by means of a detector optical system 64. A filter 66 may be used to filter out the excitation wavelength. Further details regarding preferred optical detection systems is provided in co-pending U.S. patent application No. 09/440,031, entitled "System and Method for Detecting Molecules Using an Active Pixel Sensor," which was filed on Nov. 12, 1999. The disclosure of this co-pending patent application is fully incorporated herein by reference. Other types of molecular probe arrays could also be used, such as those described in U.S. Pat. No. 5,653,939, which is fully incorporated herein by reference.

DNA analysis system 10 is preferably provided as a substantially monolithic microfluidic device that is formed by laminating and sintering together multiple layers of green-sheet, as described in more detail below, though not all of system 10 may be provided on the same monolithic device. For example, DNA detection system 28 may be provided in whole, or in part, as a separate device. However, at least DNA amplification chamber 16 of system 10 is provided as a substantially monolithic microfluidic device.

In particular, shown in FIGS. 10 and 10A is a substantially monolithic microfluidic DNA amplification device 100, in accordance with a first preferred embodiment of the present invention. Shown in FIGS. 11 and 11A is a substantially monolithic microfluidic DNA amplification device 300, in accordance with a second preferred embodiment of the present invention. As described below in more detail, device 100 is provided with a capillary electrophoresis channel for DNA detection, and device 300 is intended to be coupled to a molecular probe array for DNA detection.

Shown in FIGS. 10 and 10A is a DNA amplification device 100, in accordance with a first preferred embodiment of the present invention. Device 100 is made from green-sheet layers 102–148 that have been laminated and sintered together to form a substantially monolithic structure, as described above. Green-sheet layers 102–148 are each preferably about 100 microns thick. A cell lysis chamber 150 is formed into layers 104 and 106, a DNA separation chamber 152 is formed into layers 104 and 106, and a DNA amplification chamber 154 is formed into layers 104–142.

A sample inlet port 156 is defined by a via 158 formed into layer 102. Cell lysis chamber 150 is connected to via 158 through a channel 160 formed in layer 104. A channel 162 interconnecting chamber 150 with chamber 152 is formed in layer 104, and a channel 164 interconnects chamber 152 with chamber 154. An outlet port 166 is defined by a via 168 formed into layer 102, and a capillary electrophoresis channel 170 interconnects chamber 154 with via 168.

Cell lysis chamber 150 is typically about 50 microns wide, about 1 millimeter long, and extends about 100 microns below the channels that connect to it. DNA separation chamber 152 typically extends about 100 dimensions below the channels that connect to it, with a cross-section of 100 microns by 100 microns. DNA amplification chamber typically extends about 2 millimeters below the channels that connect to it, with a cross-section of roughly 1 millimeter by 1 millimeter. Channels 160, 162, and 164 are typically about 50 microns wide, 100 microns deep, and from about 500 microns to one centimeter long. Capillary electrophoresis channel 170 is typically about 45 microns wide, 20 microns wide, and from about 2 to 5 centimeters long.

As shown in FIG. 10A, a buffer injection port 172 is provided as a via formed into layer 102, and a waste outlet port 174 is provided as a via formed into layer 102. Ports 172 and 174 are connected to chamber 152 via channels 176 and 178, respectively, formed into layer 104. Similarly, a reagent injection port 180 is provided as a via formed into layer 102, and a waste outlet port 182 is provided as a via formed into layer 102. Channels 184 and 186, formed into layer 104, connect chamber 154 to ports 180 and 182, respectively.

As shown in FIG. 10, cell lysis chamber 150 is provided with opposing electrodes 188 and 190, which are sintered to layers 102 and 108, respectively. Electrode 188 is preferably formed by depositing, such as by screen printing, a conductive material in the form of a thick-film paste onto the lower surface of green-sheet layer 102. Similarly, electrode 190 is formed by depositing a conductive thick-film paste onto the upper surface of green-sheet layer 108. Electrodes 188 and 190 are preferably provided with a pointed surface for electric field enhancement. The pointed surfaces of electrodes 158 and 160 may be made by applying successive layers of conductive thick-film paste in a predetermined pattern.

Device 100 is provided with conductive leads to apply voltages to electrodes 188 and 190 from a voltage source (not shown) external to device 100. For example a conductor-filled via 191 may be provided in layer 102 to electrically connect electrode 188 to the outer surface of device 100. Similarly, a conductive lead defined by conductor-filled vias 192–196, formed into layers 102–106, and a conductive trace 198 formed on the surface of layer 108, electrically connects electrode 190 to the outer surface of device 100. To perform cell lysis, a voltage is applied between electrodes 158 and 160 sufficient to develop an electric field strength of about 10 to 50 kV/cm in cell lysis chamber 150.

The voltage is preferably provided in the form of pulses at a frequency of about 10–100 Hz and a duty cycle of about 50%.

Channel 162 is preferably provided with electroosmotic pumping to transport fluid from chamber 150 to chamber 152. In fact, due to the small dimensions of channel 162, as compared to chamber 150, capillary forces prevent fluid in chamber 150 from flowing through channel 162 unless pressure or pumping is applied to the fluid. To enable electroosmotic pumping, electrodes 200 and 202 are disposed at opposite ends of channel 162. Electrodes 200 and 202 may be conveniently provided as conductor-filled vias formed into layer 102. To enable electroosmotic pumping, a voltage is applied between electrodes 200 and 202, sufficient to develop an electric field strength of about 100 to 500 V/cm in channel 162.

Similarly, fluid is transported from chamber 152 to chamber 154 by electroosmotic pumping through channel 164. To allow for electroosmotic pumping, electrodes 204 and 206 are disposed at opposite ends of channel 164. A voltage is applied between electrodes 204 and 206, sufficient to develop an electric field strength of about 100 to 500 V/cm in channel 164. Electrodes 204 and 206 are preferably provided as conductor-filled vias in layer 102.

In order to use paramagnetic beads to separate the DNA from the lysed cell contents, as described above, device 100 is preferably provided with means for generating a magnetic field extending into DNA separation chamber 152. The magnetic field is preferably created by an electromagnet 210 that is integral to device 100. Electromagnet 210 preferably comprises a coil 212, with the axis of coil 212 extending into chamber 152, and a core 214 coaxial with coil 212. Coil 212 is preferably defined by loops 216–222 of conductive material sintered to layers 108–114, respectively, and a series of conductor-filled vias (not shown) formed into layers 108–112 that electrically connect loops 216–222. Loops 216–222 are preferably formed by depositing conductive material in the form of a thick-film paste onto green-sheet layers 108–114, respectively. To allow current to be applied to coil 212 from a current source (not shown) external to device 100, conductive leads 224 and 226 are provided. Conductive leads 224 and 226 may be disposed in device 100 in any convenient manner. For example, in the embodiment shown in Figure 10, conductive lead 224 is defined by a trace of conductive material on the surface of layer 108 and a series of conductor-filled vias formed into layers 108–148, so as to provide an electrical connection from loop 216 to the exterior of device 100. Conductive lead 226 is defined by a trace of conductive material on the surface of layer 114 and a series of conductor-filled vias in layers 114–148, so as to provide and electrical connection from loop 222 to the exterior of device 100. Other configurations for leads 224 and 226 could be used, however.

Core 214 is made of a high magnetic permeability material, such as ferrite. Core 214 is preferably provided by forming aligned vias 228–234 in green-sheet layers 108–114 and filling vias 228–234 with a thick-film paste containing a ferrite material so that the ferrite material becomes sintered into layers 108–114. An example of a suitable ferrite-containing thick-film paste is SEI ferrite paste MPS #220, sold by Scrantom Engineering, Inc., Costa Mesa, Calif.

To bring the fluids in DNA amplification chamber 154 to the appropriate temperatures for performing PCR, device 100 is provided with a heater 240 and a cooling element 242 in thermal contact with chamber 154. Heater 240 is preferably configured as a coil surrounding chamber 154, the coil being defined by loops 244–252 of conductive material, preferably deposited in the form of a thick-film paste on the surface of and sintered to layers 110, 114, 118, 122, 126, 130, 132, 136, and 140, respectively. A series of conductor-filled vias (not shown) formed into layers 110–140 electrically connect loops 240–252.

To allow current to be applied to coil 240 from a current source (not shown) external to device 100, conductive leads 254 and 255 extend from loops 244 and 252, respectively, to the outer surface of device 100. To provide for efficient heating, loops 244–252 preferably have a high resistance compared to conductive leads 254 and 255. Conductive leads 254 and 255 may be disposed in device 100 in any convenient manner. For example, in the embodiment shown in FIG. 10, conductive lead 254 is defined by a trace of conductive material on the surface of layer 110 and a series of conductor-filled vias formed into layers 110–148. Conductive lead 255 is defined by a trace of conductive material on the surface of layer 142 and a series of conductor-filled vias in layers 142–148. Other configurations could be used for leads 254 and 255, however.

Cooling element 242 preferably cools chamber 154 thermoelectrically. Thermoelectric cooling element 242 may comprise alternating segments of n-type and p-type thermoelectric material, such as n-type segments 260–266 and p-type segments 268–274, that are connected in series by traces of conductive material, such as the conductive traces on the surfaces of layers 144 and 148, as shown in FIG. 10. In this way, when a voltage of the appropriate polarity is applied to thermoelectric element 242, it transfers heat from chamber 154 to layer 148. N-type segments 260–266 and p-type segments 268–274 may be provided by forming vias in green-sheet layers 144 and 146 and filling the vias with a thick-film paste containing either an n-type or p-type thermoelectric material, so that the thermoelectric material becomes sintered into layers 144 and 146. The thermoelectric material is preferably $Si_{0.8}Ge_{0.2}$ that has been doped, either with phosphorus to be n-type or with boron to be p-type. This material may be co-fired with the green-sheet layers at 850° C. in a reducing atmosphere.

To allow current to be applied to thermoelectric element 242 from a current source (not shown) external to device 100, conductive leads 276 and 277 extend from segments 260 and 274, respectively, to the outer surface of device 100. Conductive leads 276 and 277 may be disposed in device 100 in any convenient manner. For example, conductive leads 276 and 277 are each defined by a trace of conductive material on the surface of layer 148 and a conductor-filled via formed into layer 148.

An alternative approach for cooling DNA amplification chamber 154 is to reduce the thermal mass associated with chamber 154 and to rely on ambient cooling.

Device 100 also preferably includes at least one temperature sensor to measure the temperature of chamber 154. More particularly, because of the relatively large depth of chamber 154, the embodiment shown in Figure includes three temperature sensors 280, 281, and 282, disposed at three different vertical locations in thermal contact with chamber 154. In this way, an average measured temperature for chamber 154 can be calculated. Based on this average measured temperature, heater 240 and cooling element 242 can be controlled at each stage in the PCR process so that the chamber 154 is at the appropriate temperature.

Temperature sensors 280–282 each comprise a trace of a conductive material having a resistance that is substantially dependent on temperature. Platinum is the preferred conductive material. Temperature sensors 280–282 each comprise a platinum trace deposited as a thick-film paste on the surface of and sintered to green-sheet layers 112, 128, and 144, respectively. A pair of conductive leads 283–285 extend from each of temperature sensors 280–282 to the exterior of device 100, respectively. Conductive leads 283–285 may be disposed in device 100 in any convenient manner, such as by a series of conductive traces and conductor-filled vias.

Capillary electrophoresis channel 170 is used for electrophoretically separating the amplified DNA products from chamber 154. To be able to perform capillary electrophoresis, channel 170 is filled with an electrophoretic medium, such as a polyacrylamide gel, and electrodes 290 and 292 are disposed at opposite ends of channel 170. A voltage is applied between electrodes 260 and 262, sufficient to develop an electric field strength of about 100–500 V/cm. The applied electric field pumps fluid electroosmotically from chamber 154 into channel 170. Moreover, under the influence of this electric field, the amplified DNA products move through channel 170 toward outlet 166, and the different components in the amplified DNA products become separated based on their differing electrophoretic mobilities. Ports 182 and 166 maybe used for flushing out chamber 154 and channel 170.

Preferably the amplified DNA products are conjugated with a fluorophore, as described above, before entering channel 170, so that their location within channel 170 can be determined using laser-induced fluorescence. To perform laser-induced fluorescence, a window 294, made of an optically transmissive material, is provided in layer 102 over channel 170. Window 294 may be formed by punching out a portion of green-sheet layer 102 and then filling the punched-out portion with a thick-film paste containing glass particles. During the firing process, the glass in the thick-film paste becomes sintered to layer 102 so as to provide glass window 294 therein. Alternatively, green-sheet layer 102 may already contain glass particles so as to be optically transmissive when fired. Using either approach, optical access is provided to channel 170.

A light source (not shown), such as a laser, of a wavelength appropriate to induce fluorescence in the fluorophore-conjugated DNA products is focused through window 294 into channel 170. The fluorescence emitted from the fluorophore-conjugated DNA products is then imaged through window 294 onto a detector (not shown), such as a charge-coupled device.

As the fluids flowing through device 100 will contain DNA, it is important that all of the surfaces with which the fluid comes into contact be biocompatible. Layers 102–148 will themselves have varying degrees of biocompatibility, depending on the materials present in the green-sheet layers. However, it has been found that adequate biocompatibility can be achieved by coating the surfaces inside device 100 with poly-p-xylene.

Shown in FIGS. 11 and 11A is a DNA amplification device 300, in accordance with a second preferred embodiment of the present invention. Device 300 is similar to device 200 in most respects. In particular, device 300 is formed from green-sheet layers 302–348 that have been laminated and sintered together to form a substantially monolithic structure. Device 300 includes an inlet port 350 in fluid communication with a cell lysis chamber 352 via a channel 354. Cell lysis chamber 352 is provided with a pair of electrodes 356 and 358, with corresponding conductive leads 360 and 362, for performing electrostatic cell lysis. Cell lysis chamber 352 is connected to a DNA separation chamber 364 via a channel 366. A buffer injection port 368 and a waste outlet port are connected to DNA separation chamber 364 via channels 372 and 374, respectively. An electromagnet 380, having a coil of conductive material 382 and a core of high magnetic permeability material 384, is provided in device 300 to direct a magnetic field into DNA separation chamber 364. Channel 366 is provided with electrodes 386 and 388 for electroosmotic pumping. A DNA amplification chamber 390 is connected to DNA separation chamber 364 via a channel 392. A reagent injection port 394 and a waste outlet port 396 are connected to chamber 390 via channels 398 and 400, respectively. Device 300 is provided with a heater 402 for heating chamber 390 and a thermo-electric cooling element 404 for cooling chamber 390. Additionally, three temperature sensors 406, 408, and 410 are provided for measuring the temperature of chamber 390.

Unlike device 200, however, device 300 does not use capillary electrophoresis for DNA detection. Instead, device 300 is intended to be used with a molecular probe array, such as shown in FIG. 41 and described above. Specifically, device 300 is provided with an outlet port 412, to allow transfer of the amplified DNA products from device 300 to the molecular probe array. Outlet port 412 is defined by a via 414 formed into layer 348. A channel 416, formed into layer 442, and vias 418 and 420, formed into layers 344 and 346, along with via 414, define a fluid passageway from chamber 390 to outlet port 412.

Preferably, a capillary stop 422 is provided in the fluid passageway between chamber 390 and outlet port 412. In this way, during the PCR process conducted in chamber 390, fluid does not flow past capillary stop 422. However, if a sufficient pressure is applied to the fluid, it is able to flow through capillary stop 422 and exit device 300 through outlet port 412.

Capillary stop 422 may comprise a region of hydrophobic material formed into layer 344 surrounding via 418. The hydrophobic material can be a glass-ceramic material, preferably containing the humite mineral norbergite ($Mg_2SiO_4.MgF_2$) as a major crystal phase. This material is described in U.S. Pat. No. 4,118,237, which is incorporated herein by reference. Thick-film pastes containing particles of these hydrophobic glass-ceramic materials may be added to define capillary stop 422.

In an additional preferred embodiment, the invention provides methods and apparatus for performing biological reactions on a substrate layer having a multiplicity of biologically reactive sites disposed thereon. The invention comprises a microfluidic reaction apparatus having one or more individual reaction chambers in direct communication with a biochip, preferably comprising one microarray of oligonucleotide probes, corresponding to each reaction chamber, disposed on the surface of the substrate, wherein each probe is anchored to the substrate by a polyacrylamide gel pad. The apparatus is advantageously used for performing multiple, parallel, thermally controlled biological reactions, most preferably hybridization reactions. Use of the reaction apparatus of the present invention, however, is not limited to DNA hybridization or thermally-controlled biological reactions. Those skilled in the art will recognize various additional uses for the apparatus. For example, the amplification of nucleic acids or the addition of labels to nucleic acids generally results in the presence of various unwanted components in the sample fluid, e.g., unincorporated nucleotides, enzymes, or DNA molecules that are of no interest. With this apparatus, probes can be used to capture nucleic acids of interest and allow the reaction by-products to be washed out of the reactor.

These embodiments are illustrated in FIGS. 20–24. FIG. 20 is an exploded perspective view from the upper side of a preferred embodiment of the present invention, illustrating the relationships between the various components. In this embodiment, the apparatus comprises a base plate 1532 having a first surface, a second surface, a first cavity 1540 comprising four well structures 1534 disposed in the first surface, and a second cavity 1541 disposed in the first surface. A biochip 1520 having a first surface containing a plurality of biologically reactive sites is inserted in the apparatus such that the biochip is removably seated in the second cavity 1541 and the first surface of the biochip is in direct communication with the first cavity 1540. Each well structure 1534 includes a groove 1536 for seating an O-ring 1548 between the biochip 1520 and the base plate 1532, wherein the O-ring 1548 defines a reaction chamber 1530 between the biochip 1520 and the base plate 1532. As will be appreciated by those in the art, other sealing structures can be used, for example gaskets of rubber and silicon, etc. A first fluid port 1538 and a second fluid port 1539 extend through base plate 1532 into each well structure 1534. A port seal 1546 can be removably applied to the second surface of base plate 1532 to temporarily close fluid ports 1538 and 1539, thereby isolating the contents of reaction chamber 1530 from the environment.

Biochip 1520 comprises one or more microarrays 1524 of biologically reactive sites 1526 disposed on a first surface of the substrate 1522 facing a first surface of the base plate 1532. A compliance layer 1550 is permanently affixed in a cavity 1560 in compression plate 1554, and the compression plate 1554 is then removably seated on base plate 1532, thereby removably locking substrate 1522 into base plate cavity 1540.

The assembly is locked together with retaining plate 1562 and retaining pins 1572, having a body 1574, a neck 1576, and a head 1578. The body 1574 of each retaining pin 1572 is press fit into a pin aperture 1544 disposed along the perimeter of base plate 1532. Retaining pin body 1574 extends through a corresponding pin aperture 1556 in compression plate 1554. The neck 1576 and head 1578 of retaining pin 1572 extend through a corresponding pin aperture 1566 in retaining plate 1562. The retaining pin aperture 1566 in retaining plate 1562 comprises a substantially circular main section 1568 configured to accept the diameter of pin head 1578, and a notch 1570 extending from the main section 1568 configured to accept the diameter of pin neck 1576, but smaller than the diameter of pin head 1578.

FIG. 21 is an exploded perspective view from the lower side of reaction apparatus 1528, illustrating the orientation of biochip 1520 in relation to base plate 1532. FIG. 22 is a perspective view from the upper side of apparatus 1528, illustrating apparatus 1528 as assembled. FIG. 23 is a perspective view from the lower side of apparatus 1528, illustrating the relationship of sealing member 1546 to base plate 1532.

FIGS. 23 and 24 are an enlarged partial view of apparatus 1528, illustrating details of base plate 1532 and the relationship of retaining pins 1572 to base plate 1532. Base plate 1532 is most preferably 5 millimeters thick, 44 millimeters wide, and 82 millimeters long, and comprises two notches 1542, six pin apertures 1544, first cavity 1540, second cavity 1541, and well structures 1534, each having an O-ring groove 1536, and first and second fluid ports 1538 and 1539. The base plate material is preferably thermally conductive in order to conduct heat from heating element 1582 to the fluid inside each reaction chamber 1530. The conductivity of the base plate material is most preferably selected to provide for alteration of the fluid temperature by at least 2 degrees centigrade per second over a range from zero degrees centigrade to 100 degrees centigrade. The base plate material is preferably titanium, copper, aluminum, ceramic, or any other material having similar mechanical and thermal properties that will not introduce gas bubbles into the reaction chamber by outgassing, and most preferably is grade 2 commercially pure titanium.

Optional base plate notch 1542 is located on either end of base plate 1532 as shown in FIG. 20, 21, 22, and 23. Notch 1542 is configured to allow laboratory technicians to easily remove a biochip 1520 with their fingers, and is most preferably 20 millimeters wide and extends laterally most preferably 4 millimeters into base plate 1532.

Base plate second cavity 1541 is most preferably 25 millimeters wide, 75 millimeters long, and 1 millimeter deep. Each dimension of cavity 1541 is slightly larger than the corresponding size of biochip 1520 to ensure minimum play of biochip 1520.

In an alternative configuration, biochip 1520 is permanently affixed to the base plate 1532, thus forming a single integrated component.

Each pin aperture 1544 is disposed along the perimeter of base plate 1532 as shown in FIG. 26 and extends entirely through base plate 1532. The pin aperture 1544 is preferably circular, having a diameter of most preferably 5 millimeters, and allows heavy press-fit around body 1574 of retaining pin 1572.

The depth of each well structure 1534 is preferably between 25 micrometers and 150 micrometers, more preferably between 75 micrometers and 150 micrometers, and most preferably between 100 micrometers and 150 micrometers. The depth selected is critical for developing the capillary action required to avoid gas bubble formation upon introduction of fluid into each reaction chamber 1530. It is also critical to minimize the depth of well structure 1534 in order to correspondingly reduce the volume of fluid required to fill reaction chamber 1530. The volume of reaction chamber 1530 is most preferably 33 microliters when well structure 1534 is 125 micrometers deep and ports 1538 and 1539 are each 1.4 millimeters in diameter.

As shown in FIG. 24, each O-ring groove 1536 is configured so that a seated O-ring 1548 completely surrounds one microarray 1524 of biologically reactive sites 1526 on biochip 1520. As shown in the Figure, each O-ring groove 1536 preferably comprises an oblong channel that extends most preferably 1.6 millimeters into base plate 1532 relative to the first surface of base plate 1532. Groove 1536 has circular end portions most preferably 11.5 millimeters in diameter, measured from the center of groove 1536 to the inner perimeter of the groove, and most preferably 9.5 millimeters apart from center-to-center. The width of the groove is chosen such that it makes a slight interference fit with an O-ring 1548, and is most preferably 1.6 millimeters in the embodiment illustrated. This condition reduces the opportunity for trapped gas bubbles to form at the interface surface between each O-ring 1548 and O-ring groove 1536. Such trapped gas bubbles could expand during heating and cause seal breach. The dimensions of groove 1536 are limited only by the size and shape of microarray 1524. As shown in FIG. 32, the boundary of each well structure 1534 extends slightly outward from the outermost perimeter of O-ring groove 1536, allowing room for O-ring 1548 to deform during compression of biochip 1520 into the surface of second cavity 1541, thereby forming a tighter seal between biochip 1520 and base plate 1532.

A first fluid port 1538 is located in the well structure 1534 immediately adjacent to the circular end portion of the inner perimeter of O-ring groove 1536. A second fluid port 1539 is located in the well structure 1534 immediately adjacent to the opposite circular end portion of the inner perimeter of O-ring groove 1536. The circular end portions of each O-ring groove 1536 provide a gradual change in flow geometry which considerably reduces the potential for bubble formation during introduction of a fluid though fluid port 1538 and removal through fluid port 1539. End portions that are parabolic or triangular in profile, or any shape that provides a gradual change in flow geometry, could also be used to create the same effect.

Each fluid port 1538 and 1539 is intended for interfacing to pipet tip 1580 and has a diameter preferably between 0.25 millimeters and 1.5 millimeters, more preferably between 0.75 millimeters and 1.5 millimeters, and most preferably between 1.25 millimeters and 1.5 millimeters. Pipet tip 1582 is preferably disposable and made of polypropylene, and can interface with a standard pipettor for manual loading of the reaction chambers. Many other similar types of pipet tips are commonly available and would be useful in the present invention.

A biologically compatible outer surface coating is optionally applied to base plate 1532 and retaining pins 1572 after all retaining pins 1572 are press-fitted into each pin aperture 1544 of base plate 1532. To enhance adhesion performance of the outer surface layer to base plate 1532, a layer of biologically compatible primer is optionally first applied to base plate 1532. Preferably the surface coating is selected from fluorinated ethylene propylene (commonly known under the trademark Teflon®), gold, platinum, polypropylene, an inert metal oxide, or any material having similar biological compatibility and mechanical properties. Most preferably, the surface coating is Teflon®. The primer material is preferably Xylan®, Teflon®, polypropylene, an inert metal oxide, or any material having similar biological compatibility and mechanical properties.

Each O-ring 1548 preferably has a circular cross-section of most preferably 1.8 millimeters in diameter, and a circular profile the inside diameter of which is most preferably 14 millimeters. Preferably the O-ring material is selected from nitrile, silicone, Kalrez®, or any biologically inert material having similar size and mechanical properties, that will not introduce gas bubbles into the reaction chamber due to outgassing. Most preferably, the O-ring is made of nitrile. Each O-ring 1548 fits into a corresponding O-ring groove 1536 in base plate 1532 such that no air gaps form between O-ring 1548 and O-ring groove 1536. When reaction chamber apparatus 1528 is assembled correctly, each well structure 1534 allows deformation of a corresponding O-ring 1548.

Biochip 1520 broadly comprises substrate 1522 and one or a plurality of microarrays 1524 disposed on a first surface thereof. In a preferred embodiment, biochip 1520 includes four microarrays 1524. The dimensions of substrate 1522 are preferably between 25 millimeters wide by 75 millimeters long by 1 millimeter thick and 325 millimeters long by 325 millimeters wide by 2 millimeters thick. Most preferably, substrate 1522 is a standard soda lime glass microscope slide 25 millimeters wide by 75 millimeters long by 1 millimeter thick. Alternative substrate materials include silicon, fused silica, borosilicate, or any rigid and biologically inert glass, plastic, or metal. As shown, biochip 1520 must be oriented with the microarray 1524 bearing surface facing toward base plate 1532. When assembled as shown, four reaction chambers 1530 are formed, each defined by a volume bounded by biochip 1520, each O-ring 1548, and each corresponding well structure 1534.

As shown in FIG. 32, in a preferred embodiment, each microarray 1524 has twenty seven biologically reactive sites 1526 in one direction and twenty seven in a direction normal to the first direction. As shown in FIG. 25, each site 1526 contains a biologically reactive three-dimensional polymerized polyacrylamide gel structure 1527 affixed to substrate 1522. Each gel structure 1527 is preferably cylindrical, most preferably having a 113 micron diameter and a 25 micron thickness. The distance between each site 1526 within each microarray 1524 is most preferably 300 micrometers, and the distance between each microarray 1524 is most preferably 15 millimeters. Each microarray 1524 is also preferably isolated by a polyacrylamide gel boundary 1525. Each site 1526 could alternatively comprise biologically reactive reagents attached directly to substrate 1522.

Optional compliance member 1550 is intended to provide a uniform distribution of clamping pressure over biochip 1520 without cracking substrate 1522. The general size of compliance member is intended to substantially match the overall size of substrate 1522. Compliance member 1550 is most preferably 65 millimeters long, 26 millimeter wide, and 3 millimeter thick, and is formed of a layer of pressure-sensitive adhesive disposed on a layer of low-compression material, preferably selected from silicone sponge rubber, natural sponge rubber, neoprene sponge rubber, or any material having similar mechanical properties. Compliance member 1550 further preferably includes four viewing ports 1552, each of which allows visual inspection of a corresponding reaction chamber 1530 and corresponds in size and shape to the inner perimeter of each O-ring groove 1536 in base plate 1532. The adhesive layer permanently attaches compliance member 1550 to cavity 1560 of compression plate 1554.

Compression plate 1554 is most preferably 44 millimeters wide, 69 millimeters long, and 4 millimeters thick. Compression plate 1554 is preferably formed of fluorinated ethylene propylene, acetal resin, polyurethane, polypropylene, acrylonitrile-butadiene-styrene (ABS), or any material having similar mechanical properties, and is most preferably formed of Teflon. Compression plate 1554 further preferably includes six retaining pin apertures 1556, four viewing ports 1558, and cavity 1560. Retaining pin apertures 1556 corresponding to the six retaining pins 1572 in base plate 1532 are located around the periphery of compression plate 1554 and pass entirely through compression plate 1554. The pin apertures 1556 are most preferably 5.5 millimeters in diameter. Each viewing port 1558 allows visual inspection of a corresponding reaction chamber 1530 and corresponds in size, shape, and location to each corresponding viewing port 1552 in compliance member 1550 as shown in FIG. 20. Compression plate cavity 1560 is most preferably 2.2 millimeters deep, 26 millimeters wide, and 65 millimeters long, and is configured to contain compliance member 1550 with minimum play.

Retaining plate 1562 is most preferably 44 millimeters wide, 69 millimeters long, 1.5 millimeters thick. The retaining plate 1562 is preferably stainless steel, copper, aluminum, titanium, or any material having similar mechanical properties, more preferably is stainless steel, and most preferably is 300 series stainless steel. Retaining plate 1562 further preferably comprises four viewing ports 1564 located around the periphery of retaining plate 1562 and six retaining pin apertures 1566, all of which pass entirely through the thickness of retaining plate 1562. Each viewing port 1564 allows visual inspection of a corresponding reaction chamber 1530 and corresponds in size, shape, and location to each corresponding viewing port 1558 in compression plate 1554. Each retaining aperture 1566 further includes a main section 1568 that is substantially circular and a notch 1570 extending from the main section 1568. Each main section 1568 is most preferably 5.5 millimeters in diameter, allowing a pin head 1578 to pass through. Each notch 1570 is most preferably 2.2 millimeters in diameter, having a center 4 millimeters from the center of the corresponding main section 1568.

As shown in FIG. 24, each retaining pin 1572 is generally cylindrical and is formed of stainless steel, aluminum, titanium, ceramic, or any material having similar mechanical properties. More preferably, retaining pin 1572 is stainless steel, and most preferably is 300 series stainless steel. Retaining pin 1572 preferably comprises body 1574, neck 1576, and head 1578. Body 1574 has a circular cross section most preferably 5 millimeters in diameter and is most preferably 7.5 millimeters long. Body 1574 is designed specifically to be press-fitted into a pin aperture 1544 such that the end of body 1574 is flush to the outer surface of base plate 1532. Alternatively, retaining pins 1572 could be an integral molded portion of base plate 1532. Substrate 1522 could also be clamped to base plate 1532 using standard fasteners including screws in place of retaining pins 1572. In large throughput embodiments, an automated clamping mechanism could be used to simultaneously clamp one or more substrates 1522 to a base plate 1532.

Pin neck 1576 has a circular cross-section most preferably 2 millimeters in diameter and 3 millimeters long and is designed specifically to engage notch 1570 in the retaining pin aperture 1566 of retaining plate 1562. Head 1578 has a circular cross-section most preferably 5 millimeters in diameter and is most preferably 2 millimeters long.

Port seal 1546 is most preferably 52 millimeters long, 24 millimeters wide, 0.1 millimeters thick, and comprises a layer of thermally conductive material having a biologically inert pressure-sensitive adhesive backing attached thereto. The conductivity of port seal 1546 is preferably selected to allow alteration of the fluid temperature by heating element 1582 at a rate of at least 2 degrees centigrade per second over a range from zero degrees centigrade to 100 degrees centigrade. Most preferably, the thermally conductive material is aluminum foil. After reaction chamber apparatus 1528 is assembled and loaded with fluid, port sealing member 1546 is temporarily affixed to base plate 1532 such that it completely seals off all ports 1538 and 1539.

Heating element 1582 heats reaction chamber apparatus 1528 by conduction directly through port sealing member 1546 and base plate 1532, and preferably is capable of altering the temperature of fluid inside each reaction chamber 1530 by at least 2 degrees centigrade per second over a range from zero degrees centigrade to 100 degrees centigrade. The embodiment describe herein is intended to interface with a flat block style Alpha Module heating element and a corresponding PTC-220 DNA Engine Tetrad available through MJ Research, Inc. although many other types of thermal cycling systems that provide conductive or convective heating could be used.

The preferred embodiment of the reaction apparatus is assembled as follows. Retaining pins 1572 are press-fit into base plate pin apertures 1544. A layer of primer is then applied to base plate 1532 containing retaining pins 1572, followed by a layer of biologically compatible surface coating. The substrate is then positioned in base plate cavity 1540, with the surface containing the microarrays 1524 of biologically reactive sites 26 facing the first surface of the base plate 1532. Compliance layer 1550 is permanently affixed in compression plate cavity 1560 by application of the adhesive layer to the compression plate 1554. The pin apertures 1556 in compression plate 1554 are aligned with the retaining pins 1572, and compression plate 1554 is then seated on base plate 1532. The main sections 1568 of retaining pin apertures 1566 in retaining plate 1562 are aligned with retaining pin heads 1578, retaining plate 1562 is seated on compression plate 1554, and retaining plate 1562 is then compressed towards base plate 1532 such that pin head 1578 extends above retaining plate 1562. Retaining plate 1562 is shifted laterally such that notch 1570 engages each corresponding pin neck 1576. Other methods of temporarily locking the compression plate to the base plate, including the use of an external clamp around the base plate and the compression plate or a layer of adhesive between the base plate and the compression plate, could also be used.

The reaction chambers 1530 are loaded by inserting pipet tip 1582 into first fluid port 1538 as far as is necessary to create a seal between tip 1582 and port 1538, and then slowly introducing fluid into the corresponding reaction chamber 1530 using a standard pipettor. Second fluid port 1539 allows air to escape as fluid enters reaction chamber 1530 through first port 1538. Pipet tip 1582 is removed from first port 38 when reaction chamber 1530 and second fluid port 1539 are completely loaded with fluid. If substrate 1522 is visually transparent, each reaction chamber 1530 may be visually inspected through each compression plate viewing port 1558 and retaining plate viewing port 1564 immediately after loading for the presence of gas bubbles. If gas bubbles are present over any microarray 1524, the fluid loading process must be performed again, or the reaction chamber must be pressurized. Pressurization may be provided manually by inserting additional fluid through a pipet tip inserted into the first fluid port while the second fluid port is sealed, or may be provided automatically by use of a pump and tubing attached to the first fluid port. Preferably the chamber is pressurized to between 27 and 207 kPa (4 and 30 psi), more preferably between 55 ad 69 kPa (8 and 10 psi), and most preferably to about 55 kPa (8 psi). Any other gas bubbles including those away from the edges of any microarray 1524, especially those near ports 1538 and 1539, are harmless and can be ignored. After inspection, port seal 1546 is affixed to the lower surface of base plate 1532 by applying the pressure-sensitive adhesive side of the port seal port 1546.

Once assembled, the reaction chamber apparatus 1528 is placed onto heating element 1584 as shown in FIG. 31, and thermal cycling is commenced. Upon completion of the reaction, reaction chamber apparatus 1528 is removed from heating element 1584, port seal 1546 is removed, retaining plate 1562 and compression plate 1554 are removed by following the corresponding assembly steps in reverse, and finally biochip 1520 is removed.

Although the detailed description and operational description previously recited contain many specific details, these should not be construed as limitations on the scope of the invention, but rather as an exemplification of one preferred embodiment thereof. Those with skill in the art will recognize the generality of the exemplified chamber, and the capacity for the recited components as disclosed herein to be varied for any particular purpose or reaction. For example, reaction chamber apparatus 1528 could be configured to accommodate a multitude of different configurations of biochip 1520, or apparatus 1528 could be configured to accommodate a biochip 1520 comprising two microarrays each having forty biologically reactive sites in one direction and one hundred in a direction normal to the first direction. The size of reaction chamber apparatus 1528 could be scaled to accommodate a substrate up to 310 millimeters wide, 310 millimeters long, and 3 millimeters thick. A high-throughput embodiment of reaction chamber apparatus 1528 that can accommodate a plurality of biochips 1520 is also possible.

The apparatus could be configured for automatic loading of reaction chamber 1530 by integrating an automated fluid pumping system to interface to each fluid port 1538 and 1539. Such a pumping system would allow introduction of a plurality of fluids into each reaction chamber 1530, and agitation and pressurization of fluids in each reaction chamber 1530.

Alternative means for creating a sealed reaction chamber around each microarray 1524 on substrate surface 15 22 of biochip 1520 also exist. For example, well structures 1534, O-rings 1548, and O-ring grooves 1536 could be replaced with a single shaped gasket member made from a biologically compatible sealing material such as silicone rubber. The thickness of the gasket can easily be selected such that when the substrate is clamped against the base plate the resulting gap between the base plate and substrate is most preferably the same as the depth of a well structure. The disposable gasket reduces the complexity of the apparatus by reducing the number of required elements and alleviates the preventive maintenance required for O-rings.

With reference to the illustration provided in FIGS. 33, the invention provides a hybridization chamber 10 comprising a biochip, which comprises a substrate 11 having a first surface 12 and a second surface 13 opposite thereto, and a flexible layer 16 affixed to the first substrate surface 12 by an adhesive layer 15. On the first surface 12 is an area 14 bounded by adhesive layer 15 an completely covered by flexible layer 16. Flexible layer 16, adhesive layer 15, and first substrate surface 12 further define a reaction volume 25 (also sometimes referred to herein as a reaction chamber). The ratio of volume 25 to area 14 is preferably from about 0.025 mL/mm$^2$ to about 0.25 mL/mm$^2$, more preferably from about 0.1 mL/mm$^2$ to about 0.25 mL/mm$^2$, and most preferably from about 0.1 mL/mm$^2$ to about 0.2 mL/mm$^2$.

While the present invention includes reaction volumes defined by the substrate, the adhesive and the flexible layer, as will be appreciated by those in the art, there are a variety of ways that the reaction volume can be formed. For example, rather than have an adhesive (in form of a gasket, for example) serve to create the "walls" of the chamber, the substrate itself may be formed to form these walls. As will be appreciated by those in the art, a wide variety of other configurations are also possible.

As shown in FIG. 33, between flexible layer 16 and first substrate surface 12 in area 14 is positioned a multiplicity of biomolecules. In a preferred embodiment, the multiplicity of biomolecules comprises an array 17 of biomolecules, which is preferably affixed to first substrate surface 12. Array 17 preferably further comprises gel pads 22. In an alternate preferred embodiment, array 17 is deposited on a continuous layer of polyacrylamide. FIG. 34 provides an exploded cross-sectional view of a portion of array 17 illustrating the gel pads 22. Each gel structure 22 is preferably cylindrical, most preferably having about a 113 micron diameter and about a 25 micron thickness. The distance between each site within each array 17 is most preferably about 300 microns.

An optional layer of a water-soluble compound 28 is included that is either solid or highly viscous at a first temperature, e.g. room temperature or storage temperatures, and a liquid or more viscous at a second, higher temperature. Preferred embodiments utilize compounds having a melting point of about 30 to about 60° C., more preferably of about 35 to about 50° C., and most preferably of about 35 to about 45° C. is deposited in volume 25 bounded by first substrate surface 12, flexible layer 16, and adhesive layer 15. Preferably, the water-soluble compound is biocompatible, does not stick to flexible layer 16, and serves to prevent mechanical damage to gel pads 22. This compound can comprise any number of materials, with polymers such as glycol polymers, dextrans, sugars and other carbohydrates being preferred. In a preferred embodiment, the compound is polyethylene glycol, most preferably polyethylene glycol 600. The compound 28 is deposited so that the entire volume 25, with the exception of that portion of volume 25 occupied by array 17, comprises compound 28.

Array 17 can be positioned on surface 12 by providing markings, most preferably holes or pits in surface 12, that act as fiducials or reference points on surface 12 for accurate placement of array 17. The presence of said fiducials is particularly advantageous in embodiments comprising a multiplicity of arrays 17 in one or a multiplicity of areas 14 on surface 12, wherein accurate placement of said arrays is required for proper spacing and orientation of the arrays in the reaction chamber.

In preferred embodiments, a first and second port 19 and 20 extend through flexible layer 16, although in some embodiments there is only a single port that serves as both the inlet and outlet port. The first port 19 serves as an input port and is positioned in flexible layer 16 so that the first opening 29 is provided within the area 14 (reaction chamber) bounded by adhesive layer 15 on first surface 12. Second port serves as an outlet port and is positioned in flexible layer 16 so that the first opening 31 opens within area 14 bounded by the adhesive layer 15 on the first surface 12.

Input and output ports 19 and 20 are preferably shaped to accept a plastic pipette tip, most preferably a 10 μL pipette tip or a 200 μL pipette tip. In preferred embodiments, input and output ports 19 and 20 are generally in the shape of a truncated cone, as shown in FIG. 35, wherein the end of the cone having the smaller diameter forms the first opening of each port 29 and 31, respectively, and the end of the cone having the larger diameter forms the second opening of each port 30 and 32, respectively. This shape creates a seal between the pipette tip and the port, enhances visibility of the port for operator accuracy and prevents protrusion of the pipette tip into volume 25, thereby preventing potential damage to components therein, particularly the flexible, gas permeable layer 16. In these embodiments, each port preferably has a diameter on second substrate surface 13 of from about 1.0 mm to about 2.0 mm, and a diameter on first substrate surface 12 of from about 0.3 mm to about 0.6 mm. The conical walls of ports 19 and 20 form an angle 54 with the second substrate surface 13, which is preferably less than 90°. Most preferably, angle 54 is less than or equal to the contact angle 55 of the biological sample fluid 26. Most preferably, angle 54 is equal to contact angle 55 such that the surface of the fluid in the port is flat. For aqueous solutions, this angle is about 60°. This geometric arrangement provides a port that tends not to leak, but instead wicks fluid into volume 25 so that the second substrate surface 13 is dry when replaceable cover 21 is applied.

The openings of ports 19 and 20 may be covered with a removable and replaceable cover 21. In preferred embodiments, replaceable cover 21 is a stopper, a gasket, or tape, most preferably a foil tape.

In some of these embodiments, one or more first notches 70 are cut into the first adhesive layer 15 such that the first notches 70 are in direct communication with the area 14 on first substrate surface 12 bounded by the first adhesive layer 15. Second notches 72 are cut into the flexible layer 16 in positions corresponding to the size and position of first notches 70 in adhesive layer 15, thus forming one or more ports. In a particularly preferred embodiment, a ring of adhesive 74 is deposited around the perimeter of each second notch 72, such that the inner perimeter of adhesive ring 74 is coextensive with the outer perimeter of second notch 72. Preferably, first and second notches 70 and 72 are circular in shape, and have a diameter that is equal to the inner diameter of adhesive ring 74. Preferably the inner diameter and outer diameter of adhesive ring 74 are selected to form a tight seal with the tip end of a pipette. In an alternate preferred embodiment, a second layer of adhesive 76 is deposited on the portions of flexible layer 16 not covering the area 14 on first substrate surface 12 and not defining first and second ports 19 and 20. In this embodiment, the apparatus further comprises a label layer 57 that is die cut in the same manner as the first adhesive layer 15 to form windows 58 that correspond in location to areas 14 on first substrate surface 12, and which is applied to second adhesive layer 76. In this embodiment, one or more third notches 78 are cut into second adhesive layer 76, such that third notches 78 correspond in shape, size, and position to first and second notches 70 and 72. Fourth notches 80, having a shape and position corresponding to first, second and third notches 70, 72 and 78, are cut into label layer 57. The diameter of fourth notches 80 is preferably greater than the diameter of first, second and third notches 70, 72 and 78, such that after the apparatus is assembled a portion of second adhesive layer 76 is exposed by fourth notch 80. Preferably the exposed portion of second adhesive layer 76 corresponds to the shape and size of a pipette tip.

In alternative embodiments of the apparatus, first and second ports 19 and 20 extend through substrate 11, rather than through flexible layer 16. Illustrative embodiments are described in co-owned and co-pending U.S. application Ser. No. 09/464,490, incorporated by reference herein. In preferred embodiments of the apparatus, area 14 on first substrate surface 12 is square or rectangular with two rounded edges at diagonally opposite corners of are 14 and two 90 degree angles at the remaining two diagonally opposite corners of area 14. Preferably, when first and second ports 19 and 20 extend through flexible layer 16, first notches 70 in first adhesive layer 15 are cut at the sharp edges of area 14, as shown in FIG. 7. These embodiments are particularly preferred as they comprise geometries that eliminate corners and therefore are useful in the prevention of bubble formation in area 14.

Substrate 11 is fabricated from any solid supporting substance, including but not limited to plastics, metals, ceramics, and glasses. Most preferably, substrate 11 is made from silicon or glass (for accuracy and stiffness), molded plastics (which reduce cost of manufacture and thermal inertia), or ceramics (for the incorporation of microfluidic elements including integrated heating elements). Most preferably, the substrate is glass.

Adhesive layer 15 is prepared using an adhesive suitable for forming a water-tight bond between substrate 11 and flexible layer 16, including, but not limited to, high temperature acrylics, rubber-based adhesives, and silicone-based adhesives. The shape of adhesive layer 15 is configured to contain 15 array 17. Adhesive layer 15 can be deposited on first substrate surface 12 in a pattern to produce area 14 in any desired shape, and is most preferably deposited to define an ellipsoid area 14. Adhesive layer 15 can be deposited using inkjet printing or offset printing methods, or by die cutting the desired shapes from a sheet of adhesive material. In addition, a substantial portion of first surface 12 can be covered with adhesive and portions of the substrate that are not desired to retain adhesive properties can be hardened preferentially, for example, by ultraviolet curing. In these embodiments, portions retaining adhesive properties can be defined using a mask and thereby retain adhesive properties necessary to affix flexible layer 16 to surface 12. In embodiments using the die cut adhesive material, the adhesive material is preferably a doublesided adhesive tape, and more preferably a double sided adhesive tape having no carrier. Adhesive layer 15 is most preferably set down in a layer between 1 and 100 $\mu$m thick, more preferably between 25 and 50 $\mu$m thick, and most preferably about 50 $\mu$m thick.

Flexible layer 16 is made of any flexible solid substance, including but not limited to plastics, including polypropylene, polyethylene, and polyvinylidene chloride (sold commercially as Saran® wrap) plastics, rubbers, including silicone rubbers, high temperature polyesters, and porous Teflon®. Flexible layer 16 is preferably both deformable and biocompatible and preferably has low permeability to liquids in order to prevent evaporation of water from the volume contained between the flexible layer and the substrate. That is, preferred embodiments utilized flexible layers that are selectively permeable to gas but impermeable or substantially impermeable to liquid. Flexible layer 16 also preferably is optically clear and should be able to withstand temperatures of between 50 and 95° C. for a period of between 8 and 12 hours without shrinkage. Flexible layer 16 preferably covers an area of from about 5 mm$^2$ to about 1400 mm$^2$, more preferably from about 5 mm$^2$ to about 600 mm$^2$, and most preferably from about 100 mm$^2$ to about 600 mm$^2$.

In a preferred embodiment, the flexible layer is a gas permeable membrane. Most preferably, flexible, gas permeable layer 16 is selected to have physical, chemical and mechanical properties such that the surface tension of sample fluid 26 prevents passage of the sample fluid through the pores of the membrane, while allowing passage of gas molecules across the flexible, gas permeable layer. Preferably, the pore size of flexible, gas permeable layer 16 is between 0.2 and 3.0 $\mu$m, more preferably between 0.2 and 1 $\mu$m, and most preferably about 0.2 $\mu$m. Flexible, gas permeable layer 16 also preferably is translucent and should be able to withstand temperatures of between 50° C. and 95° C. for a period of between 8 and 12 hours without shrinkage. In a preferred embodiment, the flexible, gas permeable layer is porous Teflon®. Membranes having these characteristics are available from Pall Specialty Materials.

In preferred embodiments, the invention further comprises a label layer 57 that is die cut in the same manner as the adhesive to form windows 58 that correspond in location to areas 14 on first substrate surface 12. The label layer is preferably a thick film having a layer of adhesive, and most preferably is an Avery laser label. The label layer is applied to the outer surface of the flexible layer, preferably by vacuum lamination. Areas 14 are preferably visible through windows 58 in label layer 57.

In a preferred embodiment, the invention further provides a means for facilitating diffusion across the flexible, gas permeable layer; this is referred to herein as a "gas diffusion accelerator". The gas diffusion accelerator is used to increase the rate of diffusion of gas bubbles from the reaction chamber across the flexible layer, as compared to the diffusion rate in the absence of the accelerator. The gas diffusion accelerator can take on a variety of configurations, but is preferably removably affixed to the flexible, gas permeable layer, or the label layer when present, in order to remove gas bubbles from the reaction chambers. The gas diffusion accelerator creates a pressure gradient or concentration gradient across flexible, gas permeable layer 16, thereby increasing the rate of diffusion of gas molecules from the sample fluid 26 contained in volume 25 across flexible, gas permeable layer 26. A preferred embodiment of the gas diffusion accelerator, wherein the gas diffusion accelerator creates a pressure gradient across flexible, gas permeable layer 16, is shown in FIG. 14. In this embodiment, a vacuum source 70 is removably affixed to flexible, gas permeable layer 16. In preferred embodiments, vacuum source 70 comprises a vacuum pump 71, a chamber seal 72 that completely surrounds area 14 and is removably affixed to flexible, gas permeable layer 16, and a length of plastic tubing 73 connecting vacuum pump 71 to reducer 72. The chamber seal may be a suction cup, a reducer, or any other structure having similar chemical and mechanical properties. Most preferably, the plastic tubing is polyurethane tubing. Most preferably the chamber seal is made of polyvinylidene fluoride (sold under the name Kynar® by Elf Atochem North America). Diffusion-facilitating means that create a concentration gradient across the membrane are also preferred. Concentration gradients are created, for example, by providing a flow of inert gas across flexible, gas permeable layer 16, wherein the molecules of the inert gas are too large to pass through flexible, gas permeable layer 16, while the gas contained in volume 25 passes freely through flexible, gas permeable layer 16. Those skilled in the art will be able to select the characteristics of flexible, gas permeable layer 16 and gas diffusion accelerators that are appropriate for their selected sample fluid 26.

Array 17 contained in area 14 on first substrate surface 12 is optionally covered with a water-soluble compound 28, which protects and seals the biochip prior to use and prevents degradation or other damage to the array. Any water-soluble compound 28 having a melting point of about 30° C. to about 60° C, more preferably of about 35° C. to about 50° C, and most preferably of about 35° C. to about is advantageously used in filling volume 25 between array 17 and flexible layer 16. Preferably, the compound is polyethylene glycol, most preferably polyethylene glycol 600. It is a particularly preferred feature of hybridization chamber 10 of the invention that water-soluble compound 28 fills the entirety of the volume 25 and more preferably also fills at least a portion of input port 19. This prevents formation of air bubbles in volume 25 because compound 28 is first melted, then carefully mixed with the sample fluid 26 within volume 25 using a roller 40 without producing air bubbles in hybridization fluid 26. The lack of air bubbles in reaction volume 25 enhances efficiency of the biological binding reaction by ensuring that interactions, such as hybridization, between the target analytes and the probes are capable of proceeding without interference from such air bubbles. In addition, it minimizes artifactual signals detected by a scanner 36 or a light pipe 37.

Ports and holes can be produced in substrate 11 by diamond drilling in glass embodiments of substrate 11 or by stamping or molding in plastic embodiments thereof, or using ceramics formulation technology outlined herein. This facilitates standardization of the hybridization chamber dimensions, for example, by producing substrates where the first and second ports 19 and 20 are produced in a single operation. Both the substrate 11 and the removable cover 21 can be set down as strips or large sheets, and can be rolled to avoid trapping air bubbles. Flexible layer 16 can be applied by vacuum lamination to avoid trapping air, or can be deposited by spinning or flowing liquid plastic over substrate 11 after treatment with adhesive 15 and water-soluble compound 28, followed by curing the flexible layer in place. Individual hybridization chambers 10 can be produced in stacks using, for example, a diamond saw as shown in FIG. 6.

FIG. 39 illustrates a preferred arrangement for manufacturing hybridization chamber 10, wherein alternating layers of flexible layer 16, adhesive layer 15, uncut substrate 11, and removable cover 21 are laid down, and hybridization chambers are produced by cutting the stacked layers, for example, with a diamond saw or any appropriate manufacturing tool. The sealed volumes 25 protect the arrays 17 from debris produced during the cutting process.

Alternative embodiments of the hybridization chamber 10 of the invention encompass a multiplicity of arrays 17 confined in a multiplicity of areas 14 underneath flexible layer 16, each area comprising an array 17 and being supplied with first port 19 and, optionally, second port 20. In these embodiments, adhesive layer 15 is deposited on first substrate surface 12 in a pattern that defines each of areas 14, and flexible layer 16 is applied to adhesive layer 15 to encompass areas 14 on said surface.

In certain embodiments of the invention, hybridization chamber 10 is produced containing array 17 or a multiplicity of arrays 17 as disclosed herein, wherein the chamber is provided ready-to-use by the addition of hybridization fluid 26 comprising one or a multiplicity of target molecules. In alternative embodiments, hybridization chamber 10 is provided without array 17, and allows for insertion thereof by a user. In these embodiments, at least one edge of flexible layer 16 is not adhered to first substrate surface 12 until array gas diffusion accelerator 17 is inserted.

In the use of the hybridization or reaction chamber 10 of the invention, an amount of a sample fluid 26, most preferably comprising a biological sample containing a target nucleic acid, is added to the reaction chamber through first port 19. Before application of the hybridization fluid 26 to the chamber, volume 25 is most preferably heated to a temperature greater than or equal to the melting temperature of water-soluble compound 28. When melted, hybridization fluid 26 can be added to the chamber and mixed with the water-soluble compound. Preferably, water-soluble compound 28 does not affect hybridization in the chamber. More preferably, the amount of compound 28 is chosen such that hybridization efficiency is improved when compound 28 is mixed with sample fluid 26.

In embodiments of the chamber comprising first port 19 but not second port 20, the hybridization fluid is preferably introduced into the chamber after compound 28 is melted, and then the fluid is cycled into and out of the chamber using, most preferably, a pipette, until fluid 26 and compound 28 are fully mixed, and the hybridization fluid evenly distributed over the surface of array 17, or mixed into gel pads 22 comprising certain embodiments of said arrays. Alternatively, hybridization fluid 26 is evenly distributed over the surface of array 17, or mixed into gel pads 22 by physically manipulating flexible layer 16, as more fully described below. In these embodiments, hybridization fluid 26 is removed after hybridization is completed, as shown in FIG. 9, and array 17 is washed by the cycling a sufficient volume of a wash solution 27 into and out of the chamber, most preferably using a pipette.

In embodiments of the chamber comprising both first port 19 and second port 20, the hybridization fluid is preferably introduced into the chamber after compound 28 is melted, and then the fluid is cycled into and out of the chamber using, most preferably, at least one pipette, until fluid 26 and compound 28 are fully mixed, and the hybridization fluid evenly distributed over the surface of array 17, or mixed into gel pads 22 comprising certain embodiments of said biochips. Hybridization is then performed by incubating the chamber for a time and at a temperature sufficient for hybridization to be accomplished. Hybridization fluid 26 is removed after hybridization has been completed using outlet port 20, and the biochip washed by the addition and cycling of a sufficient volume of a wash solution 27 into and out of the chamber, most preferably using a pipette. In these embodiments, the wash solution can also be continuously provided by addition through the input port and removal through the output port. In certain embodiments, the biochip containing the hybridized array is removed from the chamber for development or further manipulations as required. In preferred embodiments, the biochip containing the hybridized array is analyzed in situ as described below.

Prior to commencing the reaction, the reaction apparatus 10 is degassed using vacuum source 70. Preferably a vacuum of between 13 and 27 kPa (100 to 200 torr), more preferably a vacuum of between 13 and 20 kPa (100 to 150 torr), and most preferably a vacuum of about 13 kPa (100 torr) is applied. Preferably the vacuum is applied for between 10 seconds and 2 minutes, more preferably between 10 seconds and 1 minute, most preferably between 10 seconds and 30 seconds. Vacuum source 70 is then detached from flexible, gas permeable layer 16, and volume 25 is visually inspected for the presence of gas bubbles.

An advantageous embodiment of hybridization chamber 10 of the invention, further comprising a heating element 33. Most advantageously, heating element 33 has a heating surface 34 adapted to the shape of hybridization chamber 10 to substantially cover the area 14 under flexible layer 16. Heating element 33 is any suitable heating means, including but not limited to resistance heaters, thermoelectric heaters, or microwave absorbing heaters.

The hybridization chamber 10 of the invention also advantageously comprises a thermocouple 35 or other temperature-sensing or measuring element to measure the temperature of hybridization fluid 26 or chamber 10. These temperature-sensing elements advantageously are coupled with heating element 33 to control hybridization fluid 26 and wash solution 27 temperature, and can be used to calibrate other elements, such as scanning devices 36 as described below that may be sensitive to temperature.

In certain embodiments of the invention, positive hybridization is detected visually, i.e., by the production of a dye or other material that reflects visible light at sites on biochip 18 where hybridization has occurred. In these embodiments, the dye or other material is most preferably produced enzymatically, for example, using a hybridization-specific immunological reagent such as an antibody linked to an enzyme that catalyzes the production of the dye. Visual inspection can be used to detect sites of positive hybridization. More preferably, the biochip containing the hybridized array is scanned using scanner 36 as disclosed more fully below.

Positive hybridization on biochip 18 most preferably is detected by fluorescence using labeled target molecules in a biological sample, or by including intercalating dyes in the hybridization fluid 26 that fluoresce when bound by a hybridized DNA duplex and illuminated by light at a particular wavelength. Suitable intercalating dyes include, but are not limited to, ethidium bromide, Hoechst DAPI, and Alexa Fluor dyes. Suitable fluorescence labels include, but are not limited to, fluorescein, rhodamine, propidium iodide, and Cy3 and Cy5 (Amersham), that can be incorporated into target molecules, for example, in vitro amplified fragments using labeled oligonucleotide primers.

FIGS. 10A–10C illustrate an embodiment of the invention comprising a scanner 36, which is advantageously positioned over (or beneath) flexible layer 16 and moves from one end of area 14 to the opposite end, sequentially illuminating area 14 and array 17 positioned thereupon. Prior to analysis of the hybridized array, all fluid is removed from volume 25 such that flexible layer 16 is in contact with array 17. Scanner 36 then excites the fluorescent dye, preferably with short wavelength light, most preferably light with a wavelength between 250 nm and 600 nm. Scanner 36 then collects the emitted light from a specific area. The amount of light emitted is then used to determine the amount of fluorescent dye present in the area, and hence the amount of labeled target.

Particular embodiments of scanners and scanning devices 36 are shown in FIGS. 11A through 11E. It is a particularly advantageous feature of hybridization chamber 10 that flexible layer 16 is translucent to suitable wavelengths of light, including light in the ultraviolet and visible portion of the spectrum. An additional advantageous feature of hybridization chamber 10 is that flexible layer 16, which is very thin, is immediately adjacent to and in contact with biochip 18 after hybridization fluid 26 or wash fluid 27 is removed from the chamber. This combination of features reduces or eliminates free surface reflections, internal reflection of illumination from the scanner, and dispersion or scattering of illuminating light, thereby optimizing the amount of incident light that illuminates array 17. This arrangement is also more economical than in existing apparatus as it minimizes the need for highly polished, low scattering surfaces or complex or expensive lenses, and eliminates problems associated with focus and depth-of-field in more complex optical detectors.

In other embodiments, a light pipe 37 contacts the surface of flexible layer 16 that is immediately adjacent to and in contact with the surface of array 17, as shown in FIG. 11B. In these embodiments, both illuminating and emitted light are conveyed and collected by light pipe 37. The pipe is designed to be slightly flexible so as to adapt to the contoured surface of flexible layer 16. Light pipe 37 contacts flexible layer 16 that contacts array 17, thereby permitting contacts free of surface reflections even under circumstances where array 17 or light pipe 37 has localized variations in height. Advantageously, light pipe 37 has a larger surface area than array 17, so that the maximum amount of illuminating light is delivered to array 17, and the maximum amount of emitted light from array 17 is collected by light pipe 37. A further advantage of light pipe 37 is that it enables detection of bubbles formed in hybridization fluid 26 or wash buffer 27, which detection can be used as a signal for roller 40 to address flexible layer 16 to remove such bubbles. Removing bubbles in hybridization fluid 26 or wash buffer 27 reduces the frequency of non-specific binding and artifactual signals detected by scanner 36.

In additional embodiments of the invention, the area 14 defined by adhesive layer 15 further comprises a reflective layer 38 that substantially covers the entirety of the area 14 and is positioned between array 17 and the first substrate surface 12. In preferred embodiments, reflective layer 38 comprises aluminum, gold, silver, or platinum. In these embodiments, the amount of the light signal reflected or transmitted to the light-detecting portion of scanner 36 is increased up to four-fold. In further advantageous embodiments of the invention, reflective layer 38 is a metal film resistor or an RF induction heater. In these embodiments, reflective 38 layer can heat the slide without requiring additional heating elements 33. This is a particularly desirable feature in hand-held embodiments of the hybridization chamber 10 of the invention.

If required, a passivation later 39 can be applied on top of reflective layer 38. Preferably, passivation layer 39 is a layer of parylene a few microns thick that is applied by evaporation. The amount of illumination required, and hence the amount of power needed to operate scanner 36 is reduced in these embodiments, which are particularly suited to battery-operated embodiments such as hand-held devices to improve useful battery life. Furthermore, passivation layer 39 reduces artifactual signals in the light emission data by obscuring objects that it covers.

Hybridization chamber 10 is preferably supplied with a roller 40 in removable contact with flexible layer 16 and that can be moved longitudinally across areas 14 on first substrate surface 12. In preferred embodiments, the surface of roller 40 comprises a textured pattern 41, most preferably a spiral pattern, that permits the roller to efficiently mix hybridization fluid and wash solution across area 14 and array 17. The roller can move longitudinally across the surface of the chamber for mixing sample fluid and wash solutions as required. One advantageous arrangement of roller 40 (again, preferably a patterned roller) and hybridization chamber 10 is shown in FIG. 11E. As shown in the Figure, roller 40 can be advantageously connected to a movable arm 42 that can be positioned to place roller 40 in contact with flexible layer 16 when in a first position, and can be moved to a second position in which roller 40 is not in contact with flexible layer 16. Most preferably, movable arm 42 has a pivot point 44 and movement about said pivot point is preferably controlled by a solenoid. In addition to movement of roller 40 in contact with and away from hybridization chamber 10, either roller 40 or hybridization chamber 10, or both, are movable in a longitudinal direction to enable roller 40 to mix hybridization fluid 26 or wash solution 27 inside volume 25 bounded by flexible layer 16, adhesive layer 15, and first substrate surface 12 in area 14 containing array 17. In embodiments comprising a multiplicity of areas 14 containing a multiplicity of arrays 17, roller 40 is positioned to move longitudinally across each of the multiplicity of areas 14 to mix hybridization fluid 26 or wash solution 27 in each of the volumes 25 containing arrays 17.

In additional embodiments, a sample preparation chip 45, comprising a port 46, as shown in FIGS. 12A through 12C, can be attached to hybridization chamber 10. Most preferably, port 46 in sample preparation chip 45 is aligned with first port 19 in hybridization chamber 10 to permit efficient transfer of sample to volume 25. Additional fiducial references can be used to accurately align hybridization chamber 10 and sample preparation chip 45. Since access to first port 19 is through second substrate surface 13, the array can be scanned without interference from the attached sample preparation chip. In alternative embodiments of the invention, sample preparation chip 45 may be bound to second substrate surface 13 (FIG. 12B) or formed as an integral part of substrate 11 (FIG. 12C).

A preferred embodiment of hybridization chamber 10 of the invention is a hand-held embodiment as shown in FIGS. 10A–10C, further comprising a scanner 36. In these embodiments, hand-held device 47 comprises a base 48, a lid 49 and a carriage 50 embodying roller 40, scanner 36, heating element 33 and thermocouple 35. Carriage 50 is illustrated in FIG. 11A. Device 47 comprises a compartment 51 for positioning hybridization chamber 10 in proximity to carriage 50. Carriage 50 is provided with moving means for moving roller 40, scanner 36 and heating element 33 relative to hybridization chamber 10 as required for operation as described above. Carriage 50 and lid 49 are arranged to permit a user to introduce and remove hybridization fluid 26 and wash solution 27 into the chamber through first port 19 and second port 20 as required. Alternatively, device 47 further comprises fluidic connections 52 to each of the first and second ports to provide for sample introduction and array washing after hybridization of the sample thereto. Device 47 is most preferably operated by battery, although AC adapters are also advantageously encompassed by the description of the device herein. In further preferred embodiments, lid 49 further comprises a display 56 for displaying the results of the analysis.

With respect to the methods of using the devices, there are a wide variety of methods that can be used. If required, the target sequence is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, antimicrobial agents, etc., may be used, depending on the sample preparation methods and purity of the target.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

As outlined herein, the invention provides a number of capture probes that will hybridize to some portion, i.e. a domain, of the target sequence. Probes of the present invention are designed to be complementary to a target sequence (either the target sequence of the sample or to other probe sequences, for example for use in sandwich assays known in the art) such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

As described herein, there are a number of possible detection techniques that can be utilized in the present invention. In a preferred embodiment, as outlined herein, optical label techniques are used. In these embodiments, a label such as an optical dye (e.g. a fluorochrome) is added to the assay complex comprising the target analyte and the capture binding ligand. In some embodiments, for example in the case of nucleic acids, the label can be added to the target, for example by incorporation during an amplification reaction such as PCR. For example, the fluorochromes or other labels such as biotin can be added to the PCR primers or to the dNTPs for enzymatic incorporation. Alternatively, intercalators can be used as described above.

Alternatively, preferred embodiments allow the use of electrical detection methods such as those outlined in U.S. Ser. Nos. 09/458,553; 09/458,501; 09/572,187; 09/495,992; 09/344,217; WO00/31148; 09/439,889; 09/438,209; 09/344,620; 09/478,727; PCTUS00/17422; WO 98/20162; WO 98/12430; WO 98/57158; WO 99/57317; WO 99/67425; PCT 00/19889; and WO 99/57319, all of which are expressly incorporated by reference in their entirety. These embodiments utilize arrays of microelectrodes on the substrate.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Thermal Cycling Capability of Ceramic Microchip Device

The thermal cycling capability of the microchip device of the invention was examined as follows. A ceramic microchip device was constructed as described herein. The temperature of the device was regulated using a controller and computer as described below or by clamping the device onto a commercially available thermal cycler (MJ Research, Inc., Waltham, Mass.). The temperature of the device was monitored using a resistive temperature device paste (RTD; DuPont part number 5092D) having a coefficient of 3000±200 ppm/C. The microchip device was fabricated by printing the RTD paste onto the device twice in order to achieve a lower resistance value. The typical resistance of the printed RTD element on the microchip device was 300 ohm.

A multi-loop controller (MOD30ML) from Asea Brown Boveri Ltd. (ABB; Norwalk, Conn.; http://www.abb.com/global/usabb/usabb045.nsf?OpenDatabase&db=/Global/USABB/u) was used to perform the temperature control process. Temperature and time control was performed using a proportional integral differentiate (PID) algorithm available within the ABB controller. The software for time step and temperature setpoint control was written using "Application Builder" software purchased from ABB. This software allowed the time and temperature setpoint to be specified, modified and controlled using a personal computer. The computer graphical user interface that allowed setup and modification of PCR thermal procedures in real time (allowing flexible automation of the entire reaction) was Fix32, purchased from Intellution, Inc. This software is a general purpose automation control software that allows users to customize the graphical display. Data acquisition was done using the computer serial port, and thus needed no additional computer hardware components.

The thermal cycling capability of the microchip device was analyzed over the course of a 25-cycle experiment in which each cycle consisted of a "denaturation" step of 45 sec. at 94° C. and an "annealing/extension" step of 60 sec. at 72° C. For each experiment, the well structure of the microchip device contained 1 mL of PCR mix (see Example 2) and 0.5 mL of chill-out liquid wax (MJ Research). FIGS. 18A–18C. illustrate the thermal cycling capability of the microchip device of the invention during a 25-cycle experiment (FIG. 18A), over the course of 2 cycles in a 25-cycle experiment (FIG. 18B), and over the course of 2 cycles in a 25-cycle experiment in which the microchip device was attached to a commercially available thermal cycler (FIG. 18C).

The microchip device was attached to the thermal cycler as follows. A sufficient amount of mineral oil was placed on the temperature block of a thermal cycler (M J Research) to create a thermal connection between the microchip device and the temperature block. Mineral oil was first placed on the flat temperature block, and the array containing all required samples and reagents was then placed on top of the mineral oil layer. The lid of the thermal cycler was then closed. The thermal cycler controlled time and temperature variations on the microchip array; the thermal detector of the microchip array was engaged to monitor temperature changes and rates of temperature changes on the array. The temperature data was collected from the array as described above, and is shown in FIG. 18C.

The results of the performance of a PCR reaction as describe above are shown over 25 cycles (FIG. 18A) and 2 cycles (FIG. 18B). As shown in these Figures, the temperature set by the controller and computer compared favorably with that measured by the RTD, thus indicating that the microchip device of the present invention could be applied in for PCR amplification of nucleic acids. These results illustrate the rapid rates of temperature change that can be effected using the microchip arrays of the invention. As a consequence, the amount of time the reaction is maintained at the appropriate denaturation and annealing/extension temperatures is maximized, thus minimizing overall cycle times and reaction times.

In contrast, the data in FIG. 18C demonstrated that rates of temperature change are much slower using the thermal cycler than the rates obtained using the microchip itself. Due to this intrinsic inefficiency, the thermal cycler requires more cycle time and overall reaction time to achieve the same degree of fragment amplification.

Example 2

Polymerase Chain Reaction Amplification of bla on Ceramic Microchip Device

The application of the microchip device of the invention as a device for performing the polymerase chain reaction was examined as follows. A ceramic microchip device was constructed as described herein, and thermal cycling was controlled as described in Example 1.

A two-step PCR protocol was performed to amplify a 627 bp fragment of the plasmid marker β-lactamase (bla) encoding the gene responsible for ampicillin resistance (AmpR) carried by the $E.\ coli$ K12 strain, DH5α on plasmid pBluescript KS+ using a kit obtained from Perkin Elmer (Norwalk, Conn.). PCR was performed for a total of twenty-five cycles, where each cycle consisted of a "denaturation" step of 45 sec. at 94° C. and an "annealing" step of 60 sec. at 72° C. (wherein primer annealing and extension were performed at the same temperature). A 50 µL PCR reaction mixture containing bla-specific primers (BLA-f1+BLA-r1, contained in the Perkin Elmer kit) was prepared according to manufacturer's instructions, and 1 µL of this mixture was introduced into one of the wells of a ceramic microarray of the invention. The reaction mix in the microchip was covered with 0.5 mL of chill-out liquid and then was amplified as described in Example 1. The remaining portion of the mixture was placed in a standard PCR tube and PCR performed in a conventional thermal cycler (MJ Research). After the amplification reaction was completed, the reaction products from the microarray and the thermal cycler were analyzed by 4–20% polyacrylamide gel/Tris-borate EDTA gradient gel electrophoresis and visualized with an intercalating dye (SyBr-Green) using a Molecular Dynamics FluorImager set at 488 nm and appropriate calibration filters. FIG. 19 illustrates the results obtained for the PCR amplification of bla using the microchip device of the present invention (FIG. 19, lane 4) and the conventional thermal cycler (FIG. 19, lanes 2 and 3; lane 2 contains 10 µL of the reaction mixture and lane 3 contains 1 µL of the reaction mixture). The expected bla PCR product (627 bp) was obtained using the microchip device, thus indicating that the microchip device of the present invention can be used for PCR amplification of nucleic acids.

Example 3

Preparation, Assembly and Loading of a Microfluidic Reaction Chamber

Six retaining pins of 300 series stainless steel were press-fitted into apertures on a grade 2 commercially pure titanium base plate containing four well structures. A layer of Xylan 8840 black primer (Whitford Worldwide) was applied to the base plate, followed by a layer of Dupont 856–200 Teflon-FEP clear. The base plate and O-rings were soaked in a 1% Alconox Solution for at least 30 minutes, then thoroughly rinsed in distilled, de-ionized water, and dried with compressed nitrogen or air to ensure proper cleaning.

A clean O-ring (Parker Seal Group, O-Ring Division, Part No. 2-015) was pressed completely down into each O-ring groove on the base plate. A soda glass microscope slide containing four 27×27 microarrays of polyacrylamide gel pads was then inserted into the base plate cavity such that the microarrays faced the base plate.

A low-compression silicone sponge rubber compliance layer (McMaster-Carr Supply Co., Part No. 8623K82) was affixed in the cavity of a Teflon® compression plate by application of the adhesive side of the compliance member to the cavity. The retaining pin apertures in the compression plate were then aligned with the retaining pin heads, and the plate was seated on the base plate with the compliance member seated on the microscope slide.

The pin apertures in a 300 series stainless steel retaining plate were aligned with the retaining pin heads, and the retaining plate was compressed towards the base plate such that the heads extended through and above the retaining plate. The retaining plate was then shifted laterally so that the pin necks engaged the notch of the pin aperture, thereby locking the various components of the apparatus together.

The reaction chambers were loaded by inserting a pipet tip 82 (VWR Scientific Products Corporation, Prod. No. 53510-084) into a fluid port until a seal was created between the tip the port. The reaction fluid was slowly introduced into the reaction chamber using a pipettor (Rainin Instrument Company, P-200). When the reaction chamber and the second fluid port were completely filled with fluid, loading was halted. Each reaction chamber was visually inspected for the presence of gas bubbles immediately after loading. If gas bubbles were present over any microarray, the fluid loading process was restarted. The fluid ports were then sealed by applying the pressure-sensitive adhesive side of a piece of aluminum foil tape (Beckman Instruments, Inc., Part No. 270-538620-A) to lower side of the base plate such that all fluid ports were covered.

Example 4

DNA Hybridization and Labeling

Nucleic acid probe molecules immobilized to each site 26 are single-stranded; therefore, nucleic acid target molecules present within the sample fluid introduced to each site must also be single-stranded and contain a region complementary to the oligonucleotide probe molecules for hybridization to occur. Nucleic acids, however, naturally occur as double-stranded molecules. Directly introducing single-stranded target molecules to the single-stranded oligonucleotide probes immobilized to each site can involve several time consuming steps that require costly reagents and reduce the yield of the starting material. An additional complication arises because single-stranded target molecules are typically longer than the immobilized probe molecules, and often have regions complementary to each other along the same target molecule in addition to the region complementary to the immobilized probe molecule, which may result in hybridization of the target molecule to itself. This anomaly is commonly referred to as a hairpin, and may preclude hybridization of the target molecule with a complementary immobilized probe molecule.

Rapid thermal cycling in reaction chamber device alleviates the problem of hairpin formation. During the thermal cycling process, the heating element first increases the temperature of reaction chamber contents to a level just below that required to cause denaturing of any properly hybridized, double-stranded target/probe molecules in the microarray. Improperly hybridized target/probe molecules in the microarray, however, are denatured at this temperature, as are any long double-stranded molecules.

The apparatus described in Example 1 is used to perform nucleic acid amplification assays as follows. As an example, oligonucleotide probe molecules are used having a sequence length corresponding to a denaturing temperature of 60 degrees centigrade. As shown in Table 1, after the apparatus is assembled, loaded and sealed, the heating element first rapidly increases the temperature of the sample fluid within each reaction chamber to 85 degrees centigrade for 2 minutes and 30 seconds, creating conditions sufficient to denature double-stranded target molecules into single-stranded target molecules free from hairpin anomalies. The heating element then rapidly decreases the temperature of the sample fluid within each reaction chamber to 60 degrees centigrade—the calculated melting temperature of the immobilized probe molecules—for 10 minutes. The region of a single-stranded target molecule complementary to an immobilized probe molecule may then hybridize to that immobilized probe molecule before the target molecule has a chance to form a hairpin or hybridize with another complementary single-stranded target molecule.

In addition to target molecules, the sample fluid contains DNA polymerase and a specific type of free nucleotide, for example a fluorescently-labeled terminating nucleotide. After the target molecules have hybridized to the immobilized probe molecules, the DNA polymerase will covalently attach the free nucleotide to the three prime terminal ends of the five prime linked immobilized probe molecules. The polymerase can synthesize, depending on sequence complementarity, a sister molecule to the target molecule by using the immobilized probe molecule as a template. This allows identification of specific nucleotide bases within the nucleic acid sequence.

As shown in Table 1, the heating element again rapidly increases the temperature of the sample fluid within each reaction chamber again to 85 degrees centigrade for 30 seconds, again creating the conditions required for denaturing of all double-stranded target molecules in reaction chamber 30. Heating and cooling steps are repeated many times to repeat the process of covalently attaching free nucleotides to as many immobilized probe molecules as possible. As shown in Table 1, this may take up to 4 hours to complete.

TABLE 1

| Step | Temperature (Degrees centigrade) | Time (min:sec) |
|---|---|---|
| 1 | 85 | 2:30 |
| 2 | 85 | 0:30 |
| 3 | 60 | 10:00 |
| 4 | Go to step 2 and repeat 20 times | N/A |

This process can be used to query polymorphic nucleotides within a given region by using two oligonucleotide probes that are identical with the exception of a polymorphic base at the 3' terminal ends. The free nucleotides present in the sample fluid are fluorescently-labeled terminating nucleotides. When the target molecules hybridize completely with the oligonucleotide probes, the DNA polymerase is able to add exactly one fluorescent base to the probe molecule. The result can be interpreted as a digital "on/off" signal for each probe site.

An example is shown in the Figures. In this example, a blood sample from patient A and a blood sample from patient B are contained in the sample fluid. Two oligonucleotide probes having a polymorphic base at the 3' terminal end are used to hybridize with the samples. FIG. 31A illustrates complete hybridization of a region of patient A's sample with a probe having adenine as the 3' base. FIG. 31B illustrates complete hybridization of a region of patient B's sample with a probe having guanine as the 3' terminal base. In each of these cases, the complete hybridization of the target with the probe, allows the DNA polymerase in the sample fluid to attach one labeled base to the probe, and the site will be "on." FIG. 31C, however, illustrates an incomplete hybridization due to a base mismatch between the probe and target molecules at the 3' terminal position on the probe, where the probe contains an adenine and the target contains a guanine. In this case, the DNA polymerase will be unable to attach a labeled base to the probe, and the site will be "off."

Assembly of a Hybridization Chamber

The process of assembling a chamber according to the present invention is illustrated in FIG. 13.

A die cutter was used to cut four ellipsoidal holes in a layer of 502FL ultra-clean laminating adhesive film (3M). A similar pattern was punched into an Avery laser label 5663 for use as a frame and label layer. Meanwhile, a sheet of polyvinylidene chloride film was stretched over a stainless steel frame and annealed for 30 minutes at 100/C. The Avery label was applied to one side of the polyvinylidine chloride film by vacuum laminating the label in a vacuum lamination press. A vacuum of 15 psi was applied for 30 seconds, and mechanical pressure of 15 psi was maintained for 1 minute after release of the vacuum. The adhesive was then applied to the opposite side of the polyvinylidene chloride film using the same process as for the label.

The adhesive coated film was then applied to a glass slide that had previously been prepared. The arrays of oligonucleotide probes and gel pads were positioned on the glass slide using standard methods. Ports were drilled into the slide using a diamond drill. A vacuum lamination press was used to affix the polyvinylidene chloride film to the slide. A vacuum of 15 psi was maintained for 1 minute, and then mechanical pressure of 15 psi was maintained for an additional minute.

The individual chambers were then filled with polyethylene glycol 600 using a 10 mL pipette tip. A layer of 3M 7350 polyester tape was then applied to the slide to seal off the ports.

Example 5

Assembly of Top-Loading Hybridization Chamber

A die cutter was used to cut four ellipsoidal holes in a layer of 502FL ultra-clean laminating adhesive film (3M). A similar pattern was punched into an Avery laser label 5663 for use as a frame and label layer. Meanwhile, a sheet of polyvinylidene chloride film was stretched over a stainless steel frame and annealed for 30 minutes at 100° C. The Avery label was applied to one side of the polyvinylidine chloride film by vacuum laminating the label in a vacuum lamination press. A vacuum of 15 psi was applied for 30 seconds, and mechanical pressure of 15 psi was maintained for 1 minute after release of the vacuum. The adhesive was then applied to the opposite side of the polyvinylidene chloride film using the same process as for the label.

The adhesive coated film was then applied to a glass slide that had previously been prepared. The arrays of oligonucleotide probes and gel pads were positioned on the glass slide using standard methods. A vacuum lamination press was used to affix the polyvinylidene chloride film to the slide. A vacuum of 15 psi was maintained for 1 minute, and then mechanical pressure of 15 psi was maintained for an additional minute.

The individual chambers were then filled with polyethylene glycol 600 using a 10 mL pipette tip. A layer of 3M 7350 polyester tape was then applied to the slide to seal off the ports.

Example 6

Removing Gas Bubbles from a Reaction Chamber

The process of assembling a chamber according to the present invention is illustrated in FIG. 46.

A four reaction-chamber apparatus is manufactured using a layer of 0.2 μm porous Teflon unsupported membrane as the flexible, gas permeable layer, following the procedure provided in U.S. application Ser. No. 09/464,490, incorporated by reference herein. Each reaction chamber is filled with 75 μL of a sample fluid containing biological target molecules by injection through a 300 μL pipette tip (VWR Part No. 53510-084) using a 200 μL pipettor (Rainin P-200). Bubbles are visually detectable in the chambers after injection.

A reaction chamber is isolated by applying a Cole-Parmer Kynar ¼"×⅝" barbed reducer (Part No. 31513-31) directly to the frame layer and forming a seal around the chamber. A "house" vacuum source is connected to the reducer by a length of polyurethane tubing. A vacuum of 200 torr is applied for two minutes. Visual inspection of the chamber following application of the vacuum shows no gas bubbles remaining in the chamber.

The reaction apparatus is maintained at 25° C. and atmospheric pressure for 8 hours until the reaction proceeds to completion. No appreciable evaporation of water from the chamber is observed.

We claim:

1. A method of detecting a target analyte in a plurality of samples, said method comprising:
   introducing at least a first sample to a first microchannel;
   introducing at least a second sample to a second microchannel; wherein said first and second microchannel each comprise a plurality of spatially distinct regions upon which capture binding ligands are immobilized;
   flowing said first and second sample through said first and second microchannels to form at least one assay complex comprising the target analyte;
   recirculating the flow of at least one sample in at least one microchannel and detecting said target analyte.

2. A method according to claim 1, wherein said capture binding ligands are nucleic acids.

3. A method according to claim 1, wherein said capture binding ligands are proteins.

4. A method according to claim 1, wherein said spatially distinct regions comprise porous polymer with said capture binding ligands bound to the porous polymer.

5. A method according to claim 1, wherein said spatially distinct regions comprise beads with said capture binding ligands bound to the bead.

6. A method according to claim 1, further comprising forming said spatially distinct regions by introducing hydrogels into at least said first or second microchannel.

7. A method according to claim 1, further comprising: selectively dispensing said capture binding ligands on spatially distinct portions of hydrogel.

8. A method according to claim 1, further comprising: selectively dispensing said capture binding ligands on spatially distinct portions of polyacrylamide.

9. A method according to claim 1, wherein said method further comprises:
   generating an optical signal indicative of the assay complex; and wherein said detecting comprises detecting the optical signal.

10. A method according to claim 1, wherein said method further comprises:
    generatin a fluorescent signal indicative of the assay complex, and wherein said detecting comprises detecting the fluorescenet signale.

11. A method according to claim 1, wherein said method further comprises
    generating an electronic signal indicative of the assay complex; and wherein said detecting comprises detecting the electronic signal.

12. A method according to claim 1, wherein said first or second microchannel is at least partially formed from a substrate comprising glass.

13. A method according to claim 1, wherein said first or second microchannel is at least partially formed from a substrate comprising plastic.

14. A method according to claim 1, wherein said first or second microchannel is at least partially formed from a substrate comprising polymer.

15. A method of detecting a target analyte in a plurality of samples, said method comprising:
    introducing at least a first sample to a first microchannel;
    introducing at least a second sample to a second microchannel; wherein said first and second microchannel each comprise a plurality of spatially distinct regions comprising electrodes upon which capture binding ligands are immobilized;
    flowing said first and second sample through said first and second microchannels to form at least one assay complex comprising the target analyte; recirculating the flow of at least one sample in least one microchannel; and detecting said target analyte.

16. A method according to claim 15, wherein said capture binding ligands are nucleic acids.

17. A method according to claim 15, wherein said capture binding ligands are proteins.

18. A method according to claim 15, wherein said method further comprises:
    generating an optical signal indicative of the assay complex; and wherein said detecting comprises detecting the optical signal.

19. A method according to claim 15, wherein said method further comprises:
    generating a fluorescent signal indicative of the assay complex, and wherein said detecting comprises detecting the fluorescent signal.

20. A method according to claim 15, wherein said method further comprises
    generating an electronic signal indicative of the assay complex; and wherein said detecting comprises detecting the electronic signal.

21. A method according to claim 15, wherein said first or second microchannel is at least partially formed from a substrate comprising glass.

22. A method according to claim 15, wherein said first or second microchannel is at least partially formed from a substrate comprising plastic.

23. A method according to claim 15, wherein said first or second microchannel is at least partially formed from a substrate comprising polymer.

24. A method according to claim 15, wherein said detecting occurs on at least one of said electrodes.

25. A method according to claim 15, further comprising pumping said first or second sample.

* * * * *